US011098283B2

(12) United States Patent
Gautam et al.

(10) Patent No.: US 11,098,283 B2
(45) Date of Patent: Aug. 24, 2021

(54) T CELLS MODIFIED TO OVEREXPRESS C-MYB

(71) Applicant: The United States of America, as represented by the Secretary, Department of Health and Human Services, Bethesda, MD (US)

(72) Inventors: Sanjivan Gautam, Rockville, MD (US); Yun Ji, Germantown, MD (US); Luca Gattinoni, Washington, DC (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 114 days.

(21) Appl. No.: 15/754,078

(22) PCT Filed: Aug. 24, 2016

(86) PCT No.: PCT/US2016/048435
§ 371 (c)(1),
(2) Date: Feb. 21, 2018

(87) PCT Pub. No.: WO2017/035251
PCT Pub. Date: Mar. 2, 2017

(65) Prior Publication Data
US 2018/0258394 A1    Sep. 13, 2018

Related U.S. Application Data

(60) Provisional application No. 62/209,497, filed on Aug. 25, 2015.

(51) Int. Cl.
| C12N 5/0783 | (2010.01) |
| C07K 14/82 | (2006.01) |
| C07K 14/725 | (2006.01) |
| A61K 35/17 | (2015.01) |
| A61K 35/12 | (2015.01) |
| A61P 31/12 | (2006.01) |
| A61P 35/00 | (2006.01) |

(52) U.S. Cl.
CPC ............ *C12N 5/0638* (2013.01); *A61K 35/17* (2013.01); *C07K 14/7051* (2013.01); *C07K 14/82* (2013.01); *A61K 2035/124* (2013.01); *A61P 31/12* (2018.01); *A61P 35/00* (2018.01)

(58) Field of Classification Search
None
See application file for complete search history.

(56) References Cited

U.S. PATENT DOCUMENTS

| 7,820,174 | B2 | 10/2010 | Wang et al. |
| 8,034,334 | B2 | 10/2011 | Dudley et al. |
| 8,216,565 | B2 | 7/2012 | Restifo et al. |
| 8,383,099 | B2 | 2/2013 | Dudley et al. |
| 8,465,743 | B2 | 6/2013 | Rosenberg et al. |
| 8,785,601 | B2 | 7/2014 | Rosenberg et al. |
| 2012/0101148 | A1 | 4/2012 | Aking et al. |
| 2012/0244133 | A1 | 9/2012 | Rosenberg et al. |
| 2013/0274203 | A1 | 10/2013 | Morgan et al. |
| 2014/0037628 | A1 | 2/2014 | Morgan et al. |
| 2014/0274909 | A1 | 9/2014 | Orentas et al. |

OTHER PUBLICATIONS

Salomoni et al., Proc. Natl. Acad. Sci., vol. 94, pp. 3296-3301 (1997) (Year: 1997).*
Zhou et al. (Front Biosci;16: 1109-1131 (2014). (Year: 2014).*
Sala et al. ((1995) Blood 86, 3404-3412). (Year: 1995).*
Clarke et al. (Mol Cell Biol 8:884, 1988). (Year: 1988).*
Majello et al. (Proc. Natl. Acad. Sci. USA 83:9636-9640 (1986)). (Year: 1986).*
Genbank M15024.1 (pp. 1-2, 1994). (Year: 1994).*
Gillis et al., (Nature. Jul. 14, 1977;268(5616):154-6). (Year: 1977).*
Inge et al., J Immunol 1992; 148:3847-3856. (Year: 1992).*
Cho et al., J Investig Allergol Clin Immunol. 2003;13(4):259-265 (abstract only). (Year: 2003).*
Allen et al., "c-Myb is essential for early T cell development," *Genes and Development*, 13(9): 1073-1078 (1999).
Badiani et al., "Dominant Interfering Alleles Define a Role for C-Myb in T-Cell Development," *Genes and Development*, 8(7): 770-782 (1994).
Bender et al., "Critical functions for c-Myb at three checkpoints during thymocyte development," *Nat. Immunology*, 5(7): 721-729 (2004).
Cheng et al., "Multiplexed activation of endogenous genes by CRISPR-on, an RNA-guided transcriptional activator system," *Cell Res.*, 23: 1163-71 (2013).
Emambokus et al., "Progression through key stages of haematopoiesis is dependent on distinct thresholds levels of c-Myb," *EMBO J.*, 22(17): 4478-4488 (2003).
Gattinoni et al., "A human memory T-cell subset with stem cell-like properties," *Nature Med.*, 17(10): 1290-1298 (2011).
Gattinoni et al., "Paths to stemness: building the ultimate antitumor T cell," *Nature Rev.*, 12: 671-684 (2012).
Gattinoni et al., "Removal of homeostatic cytokine sinks by lymphodepletion enhances the efficacy of adoptively transferred tumor-specific CD8+ T cells," *J. Exp. Med.*, 202: 907-912 (2005).

(Continued)

*Primary Examiner* — Zachary S Skelding
(74) *Attorney, Agent, or Firm* — Leydig, Voit & Mayer, Ltd.

(57) ABSTRACT

Provided is an isolated or purified T cell comprising an antigen-specific receptor, wherein the antigen-specific receptor is a T cell receptor (TCR) or a chimeric antigen receptor (CAR), wherein the T cell has been modified to express a transcription factor at a level that is higher than the level of the transcription factor expressed by a T cell that has not been modified to express the transcription factor, wherein the transcription factor is V-Myb Avian Myeloblastosis Viral Oncogene Homolog (c-Myb), a functional variant of c-Myb, or a functional fragment of c-Myb. Related populations of cells, pharmaceutical compositions, methods of treating a disease, and methods of inhibiting the differentiation of T cells are also provided.

23 Claims, 8 Drawing Sheets
Specification includes a Sequence Listing.

(56) References Cited

OTHER PUBLICATIONS

GenBank Accession No. AA170760.1 "ms86f10.r1 Soares mouse 3NbMS Mus musculus cDNA clone IMAGE:618475 5—similar to gb:M12848_rna8 Mouse myb proto-oncogene mRNA encoding 71 kd myb protein, (MOUSE);, mRNA sequence" (1996).
GenBank Accession No. AAA37505.1 "c-myb protein, partial [Mus musculus]" (1993).
GenBank Accession No. AAA39782.1 "myb protein, partial [*Mus musculus domesticus*]" (1993).
GenBank Accession No. AAA39783.1 "myb protein, partial [Mus musculus]" (1993).
GenBank Accession No. AAA39786.1 "myb protein, partial [Mus musculus]" (1993).
GenBank Accession No. AAA39787.1 "truncated c-myb, partial [Mus musculus]" (2016).
GenBank Accession No. AAA72118.1 "unnamed protein product, partial [*Homo sapiens*]" (2016).
GenBank Accession No. AAB49034.1 "c-MYB [*Homo sapiens*]" (2010).
GenBank Accession No. AAB49035.1 "c-MYB [*Homo sapiens*]" (2010).
GenBank Accession No. AAC96326.1 "MYB proto-oncogene protein [*Homo sapiens*]" (1998).
GenBank Accession No. AC_000032.1 "Mus musculus strain mixed chromosome 10, alternate assembly Mm_Celera, whole genome shotgun sequence" (2015).
GenBank Accession No. ADL14499.1 "v-myb myeloblastosis viral oncogene homolog (avian) [*Homo sapiens*]" (2010).
GenBank Accession No. AJ606317.1 "*Homo sapiens* mRNA for v-myb myeloblastosis viral oncogene homologue (avian), (c-myb gene), splice variant 8A" (2008).
GenBank Accession No. AJ606318.1 "*Homo sapiens* mRNA for v-myb myeloblastosis viral oncogene homologue (avian), (c-myb gene), splice variant 9Ai" (2008).
GenBank Accession No. AJ606319.1 "*Homo sapiens* mRNA for v-myb myeloblastosis viral oncogene homologue (avian), (c-myb gene), splice variant 9Aii" (2008).
GenBank Accession No. AJ606320.1 "*Homo sapiens* mRNA for v-myb myeloblastosis viral oncogene homologue (avian), (c-myb gene), splice variant 8" (2008).
GenBank Accession No. AJ606321.1 "*Homo sapiens* mRNA for v-myb myeloblastosis viral oncogene homologue (avian), (c-myb gene), splice variant 8B" (2008).
GenBank Accession No. AJ606322.1 "*Homo sapiens* mRNA for v-myb myeloblastosis viral oncogene homologue (avian), (c-myb gene), splice variant 10A" (2008).
GenBank Accession No. AJ606323.1 "*Homo sapiens* mRNA for v-myb myeloblastosis viral oncogene homologue (avian), (c-myb gene), splice variant 13A" (2008).
GenBank Accession No. AJ606324.1 "*Homo sapiens* mRNA for v-myb myeloblastosis viral oncogene homologue (avian), (c-myb gene), splice variant 14A" (2008).
GenBank Accession No. AJ616235.1 "*Homo sapiens* mRNA for v-myb myeloblastosis viral oncogene homologue (avian), (c-myb gene)" (2016).
GenBank Accession No. AJ616791.1 "*Homo sapiens* c-myb gene for v-myb myeloblastosis viral oncogene homologue (avian), exon 1 and joined CDS" (2006).
GenBank Accession No. AK036518.1 "Mus musculus adult male bone cDNA, RIKEN full-length enriched library, clone:9830125P17 product:myeloblastosis oncogene, full insert sequence" (2010).
GenBank Accession No. AK038118.1 "Mus musculus 16 days neonate thymus cDNA, RIKEN full-length enriched library, clone:A130080E24 product:unclassifiable, full insert sequence" (2010).
GenBank Accession No. AK084390.1 "Mus musculus 12 days embryo eyeball cDNA, RIKEN full-length enriched library, clone:D230035O09 product:myeloblastosis oncogene, full insert sequence" (2010).
GenBank Accession No. AK088020.1 "Mus musculus 2 days neonate thymus thymic cells cDNA, RIKEN full-length enriched library, clone:E430002G18 product:myeloblastosis oncogene, full insert sequence" (2016).
GenBank Accession No. CAA27724.1 "myb proto-oncogene, partial [Mus musculus]" (2016).
GenBank Accession No. CAA34425.1 "unnamed protein product, partial [Mus musculus]" (2016).
GenBank Accession No. CAA34426.1 "unnamed protein product [Mus musculus]" (1991).
GenBank Accession No. CAE55168.1 "v-myb myeloblastosis viral oncogene homologue (avian) [*Homo sapiens*]" (2008).
GenBank Accession No. CAE55169.1 "v-myb myeloblastosis viral oncogene homologue (avian) [*Homo sapiens*]" (2008).
GenBank Accession No. CAE55170.1 "v-myb myeloblastosis viral oncogene homologue (avian) [*Homo sapiens*]" (2008).
GenBank Accession No. CAE55171.1 "v-myb myeloblastosis viral oncogene homologue (avian) [*Homo sapiens*]" (2008).
GenBank Accession No. CAE55172.1 "v-myb myeloblastosis viral oncogene homologue (avian) [*Homo sapiens*]" (2008).
GenBank Accession No. CAE55173.1 "v-myb myeloblastosis viral oncogene homologue (avian) [*Homo sapiens*]" (2008).
GenBank Accession No. CAE55174.1 "v-myb myeloblastosis viral oncogene homologue (avian) [*Homo sapiens*]" (2008).
GenBank Accession No. CAE55175.1 "v-myb myeloblastosis viral oncogene homologue (avian) [*Homo sapiens*]" (2008).
GenBank Accession No. CAE82649.1 "v-myb myeloblastosis viral oncogene homologue (avian), partial [*Homo sapiens*]" (2016).
GenBank Accession No. CAF04477.1 "unnamed protein product [*Homo sapiens*]" (2006).
GenBank Accession No. CAS01767.1 "unnamed protein product [*Homo sapiens*]" (2008).
GenBank Accession No. CBX51725.1 "unnamed protein product [*Homo sapiens*]" (2010).
GenBank Accession No. CH_466562.2 "Mus musculus 232000009742558 genomic scaffold, whole genome shotgun sequence" (2016).
GenBank Accession No. EAW47968.1 "v-myb myeloblastosis viral oncogene homolog (avian), isoform CRA_b, partial [*Homo sapiens*]" (2015).
GenBank Accession No. EDL03418.1 "myeloblastosis oncogene, isoform CRA_a, partial [Mus musculus]" (2016).
GenBank Accession No. EDL03419.1 "myeloblastosis oncogene, isoform CRA_b, partial [Mus musculus]" (2016).
GenBank Accession No. K03547.1 "Mouse c-myb gene, exon 6 and flanks" (1993).
GenBank Accession No. NC_000006.12 "*Homo sapiens* chromosome 6, GRCh38.p7 Primary Assembly" (2016).
GenBank Accession No. NC_000076.6 "Mus musculus strain C57BL/6J chromosome 10, GRCm38.p4 C57BL/6J" (2016).
GenBank Accession No. NC_018917.2 "*Homo sapiens* chromosome 6, alternate assembly CHM1_1.1, whole genome shotgun sequence" (2016).
GenBank Accession No. NG_012330.1 "*Homo sapiens* MYB proto-oncogene, transcription factor (MYB), RefSeqGene on chromosome 6" (2017).
GenBank Accession No. NM_001130172.1 "*Homo sapiens* MYB proto-oncogene, transcription factor (MYB), transcript variant 3, mRNA" (2017).
GenBank Accession No. NM_001130173.1 "*Homo sapiens* MYB proto-oncogene, transcription factor (MYB), transcript variant 1, mRNA" (2017).
GenBank Accession No. NM_001161656.1 "*Homo sapiens* MYB proto-oncogene, transcription factor (MYB), transcript variant 4, mRNA" (2017).
GenBank Accession No. NM_001161657.1 "*Homo sapiens* MYB proto-oncogene, transcription factor (MYB), transcript variant 5, mRNA" (2017).
GenBank Accession No. NM_001161658.1 "*Homo sapiens* MYB proto-oncogene, transcription factor (MYB), transcript variant 6, mRNA" (2017).

(56) References Cited

OTHER PUBLICATIONS

GenBank Accession No. NM_001161659.1 "*Homo sapiens* MYB proto-oncogene, transcription factor (MYB), transcript variant 7, mRNA" (2017).
GenBank Accession No. NM_001161660.1 "*Homo sapiens* MYB proto-oncogene, transcription factor (MYB), transcript variant 8, mRNA" (2017).
GenBank Accession No. NM_001198914.1 "Mus musculus myeloblastosis oncogene (Myb), transcript variant 1, mRNA" (2017).
GenBank Accession No. NM_005375.2 "*Homo sapiens* v-myb avian myeloblastosis viral oncogene homolog (MYB), transcript variant 2, mRNA" (2015).
GenBank Accession No. NM_010848.3 "Mus musculus myeloblastosis oncogene (Myb), transcript variant 2, mRNA" (2017).
GenBank Accession No. NP_001123644.1 "transcriptional activator Myb isoform 3 [*Homo sapiens*]" (2017).
GenBank Accession No. NP_001123645.1 "transcriptional activator Myb isoform 1 [*Homo sapiens*]" (2017).
GenBank Accession No. NP_001155128.1 "transcriptional activator Myb isoform 4 [*Homo sapiens*]" (2017).
GenBank Accession No. NP_001155129.1 "transcriptional activator Myb isoform 5 [*Homo sapiens*]" (2017).
GenBank Accession No. NP_001155130.1 "transcriptional activator Myb isoform 6 [*Homo sapiens*]" (2017).
GenBank Accession No. NP_001155131.1 "transcriptional activator Myb isoform 7 [*Homo sapiens*]" (2017).
GenBank Accession No. NP_001155132.1 "transcriptional activator Myb isoform 8 [*Homo sapiens*]" (2017).
GenBank Accession No. NP_001185843.1 "transcriptional activator Myb isoform 1 [Mus musculus]" (2017).
GenBank Accession No. NP_005366.2 "transcriptional activator Myb isoform 2 [*Homo sapiens*]" (2017).
GenBank Accession No. NP_034978.3 "transcriptional activator Myb isoform 2 [Mus musculus]" (2017).
Gommans et al.,"Engineering Zinc Finger Protein Transcription Factors: The Therapeutic Relevance of Switching Endogenous Gene Expression on or off at Command," *J. Mol. Biol.*, 354(3): 507-519 (2005).
Greig et al., "Critical roles for c-Myb in hematopoietic progenitor cells," *Seminars in Immunology*, 20(4): 247-256 (2008).
International Bureau, International Search Report and Written Opinion in International Application No. PCT/US2016/048435, dated Dec. 15, 2016.
Klebanoff et al., "IL-15 enhances the in vivo antitumor activity of tumor-reactive CD8$^+$ T Cells," *Proc. Natl. Acad. Sci. USA*, 101:1969-1974 (2004).
Lieu et al., "Requirement of c-myb in T cell development and in mature T cell function," *Proceedings of the National Academy of Sciences*, 101(41): 14853-14858 (2004).
Maurice et al., "c-Myb regulates lineage choice in developing thymocytes via its target gene Gata3," *EMBO Journal*, 26(15): 3629-3640 (2007).
Oh et al., "The myb gene family in cell growth, differentiation and apoptosis," *Oncogene*, 18: 3017-3033 (1999).
Overwijk et al., "Tumor regression and autoimmunity after reversal of a functionally tolerant state of self-reactive CD8+ T cells," *J. Exp. Med.*, 198(4): 569-80 (2003).
Phan et al., "Identification of an Inducible Regulator of c-myb Expression during T-Cell Activation," *Mol. & Cell. Biol.*, 16(5): 2387-93 (1996).
Riviere et al., "Variable correction of Artemis deficiency by I-Sce1-meganuclease-assisted homologous recombination in murine hematopoietic stem cells," *Gene Ther.*, 21(5): 529-32 (2014).
Salomoni et al., "Resistance to apoptosis in CTLL-2 cells constitutively expressing c-Myb is associated with induction of BCL-2 expression and Myb-dependent regulation of bcl-2 promoter activity," *PNAS*, 94: 3296-3301 (1997).
Sandberg et al., "c-Myb and p300 Regulate Hematopoietic Stem Cell Proliferation and Differentiation," *Developmental Cell* 8(2): 153-166 (2005).
Yuan et al., "c-Myb Promotes the Survival of CD4+CD8+ Double-Positive Thymocytes through Upregulation of Bcl-xL," *J. Immunology*, 184(6): 2793-2804 (2010).
Zeng et al., "Synergy of IL-21 and IL-15 in regulating CD8+ T cell expansion and function," *J. Exp. Med.*, 201: 139-148 (2005).
Zeng et al., "The role of c-Myb in the up-regulation of methionine adenosyltransferase 2A expression in activated Jurkat cells," *Biochem. J.*, 353: 163-168 (2001).
Zhang et al., "Efficient construction of sequence-specific TAL effectors for modulating mammalian transcription," *Nature Biotechnol.*, 29: 149-153 (2011).
Gautam et al., "The transcription factor c-Myb regulates CD8+ T cell stemness and antitumor immunity," *Nature Immunology* 20:337-349 (Mar. 2019).

* cited by examiner

SEQUENCE LISTING

```
<160> NUMBER OF SEQ ID NOS: 21

<210> SEQ ID NO 1
<211> LENGTH: 3777
<212> TYPE: DNA
<213> ORGANISM: Mus musculus

<400> SEQUENCE: 1
gggagtgtcc aaacctcttt gtttgatggc atctgtttac agagttacac tttaatatca      60
acctgtttcc tcctcctcct tctcctcctt ctcctcctcc tcctcggtga cctccttctc     120
ctcccctttc tccggagaaa cttcgccccg gcggtgcgga gcgccgctgc gcagccgggg     180
gaggacgcag gcaaggcgga gggcagcggg aggcggcaac cggtgcggtc cccggggctc     240
ttggcggagc cccggcccgc ctcgccatgg cccggagacc ccgacacagc atctacagta     300
gcgatgaaga tgatgaagac attgagatgt gtgaccatga ctacgatggg ctgctgccca     360
aatctggaaa gcgtcacttg gggaaaacta ggtggacaag ggaagaggat gagaagctga     420
agaagctggt ggaacagaac ggaacagacg actggaaagt cattgccaat tatctgccca     480
accggacaga tgtgcagtgc caacaccggt ggcagaaagt gctgaaccct gaactcatca     540
aaggtccctg gaccaaagaa gaagatcaga gagtcataga gcttgtccag aaatatggtc     600
cgaagcgttg gtctgttatt gccaagcact taaaagggag aattggaaag cagtgtcggg     660
agaggtggca caaccatttg aatccagaag ttaagaaaac ctcctggaca gaagaggagg     720
acagaatcat ttaccaggca cacaagcgtc tggggaacag atgggcagag atcgcaaagc     780
tgctgcccgg acggactgat aatgctatca agaaccactg gaattccacc atgcgtcgca     840
aggtggaaca ggaaggctac ctgcaggagc cttccaaagc cagccagacg ccagtggcca     900
cgagcttcca gaagaacaat catttgatgg ggtttgggca tgcctcacct ccatctcagc     960
tctctccaag tggccagtcc tccgtcaaca gcgaatatcc ctattaccac atcgccgaag    1020
cacaaaacat ctccagtcac gttccctatc ctgtcgcatt gcatgttaat atagtcaacg    1080
tccctcagcc ggctgcggca gccatccaga gacactataa cgacgaagac cctgagaagg    1140
aaaagcgaat aaaggagctg gagttgctcc tgatgtcaac agagaacgag ctgaagggac    1200
agcaggcatt accaacacag aaccacactt gcagctaccc cgggtggcac agcacctcca    1260
```

-continued

```
ttgtggacca gaccagacct catggggata gtgcacctgt ttcctgtttg ggagaacacc    1320
atgccacccc atctctgcct gcagatcccg gctccctacc tgaagaaagt gcctcaccag    1380
caaggtgcat gatcgtccac cagggcacca ttctggacaa tgttaagaac ctcttagaat    1440
ttgcagaaac actccagttt atagattctg attcttcgtg gtgtgatctc agcagttttg    1500
aattctctga agaagcggca gcttttcac ctagccagca gcccacaggc aaagccttcc     1560
agcttcagca aagagagggc catgggacta gatctgcagg agagcctagc ctgagggtga    1620
ccaggcgagt gctgagcgag gcatccctcg gcccagactc accccaagcg aggcacagca    1680
aggttccgct ggtcgtccta cgaaaaaggc ggggccaggc cagcccccta gccgctggag    1740
agcctagccc ctccctcttt gctgacgtca tcagctcaac tctcaagcgt tccctgtca     1800 aaagcctacc cttctctccc tcgcagttct gaacacttc cagcaaccat gaaagctcgg     1860
gcttagatgc acctacctta ccctccactc ctctcattgg tcacaaactg acaccatgtc    1920
gagaccagac tgtgaaaacc cagaaggaaa attccatctt tagaactcca gctatcaaaa    1980
ggtcaatcct cgaaagctct cctcgaactc ccacaccatt caaacatgcc cttgcagctc    2040
aagaaattaa atacggtccc ctgaagatgc tacctcagac ccctcccat gcagtggagg     2100 acctacaaga tgtgattaag caggaatcgg atgaatctgg aattgtggct gagtttcaag    2160
agagtggacc accgttactg aaaaaaatca gcaggaggt ggagtcgcca actgagaaat     2220
cgggaaactt cttctgctca aaccactggg cagagaacag cctgagcacc cagctgttct    2280
cgcaggcgtc tcctgtggca gatgccccaa atattcttac aagctctgtt ttaatgacac    2340
ctgtatcaga agatgaagac aatgtcctca agcctttac cgtacctaag aacaggcccc     2400
tggtgggtcc cttgcagcca tgcagtggtg cctgggagcc agcatcctgt gggaagacag    2460
aggaccagat gacggcctcc ggtccggctc ggaaatacgt gaacgcgttc tcagctcgaa    2520
ctctggtcat gtgagacatt tccagaaaag cattatggtt ttcagaacac ttaaaagttg    2580
actttcgaca catggctcct cagcgtggag cgctccatgg ctgagagaag agcctgattt    2640
tgttgtggta caacagttga gagcagcacc aagtgcattt ttagttgctt gagatctcac    2700
ttgatttcac acaactaaaa aggattttt tttttaaaaa taataataat gaataacagt     2760
cttacctaaa ttattaggta atgaattgtg accatttgtt aatatcataa tcagattttt    2820
taaaaaaaat aaaatgattt atttgtattt tagaggatac aacagatcag tattttgac     2880 tgtggtgaat ttaaaaaaaa aatttacaca agaaatatc ccagtattcc atgtatctca     2940
gtcactaaac atacacagag agattttaa aaaccaggag aagcattatt ttgaatgtta     3000
gctaaatccc aagtaatact taatgcaacc ctctaggagc tcatttgtgg ctaataatct    3060
tggaaatatc tttattatac taaaccattt catgaggaga atttgttgt cagcttgctt     3120 gaaaagttat tactgtatga aatagtttta ttgaaaaaat tatattttta ttcagtaatt    3180
taattttgta aatgccaaat ggagaaatgt gttcgctgct atggttttag cctgtagtca    3240
tgctgctagc tagtgtcagg gggcaataga gcttagatgg aaaaaagaga aagagactcg    3300
gtgttagata acggactatg cactagtatt ccagactttt ttatttttat atatatgtac    3360
cttttccttt tgtaattgga aaacttattt gggagaattt tgcatttgtt gtacattttt    3420
gttttttagg atttttttt tttgttgtta ttgtcgattt ataaaagcat tgcacttctt     3480 tttcttttt tgggagattt gtgttgttta tgtcatatgt tttgtttga gttcagcctg      3540 aatgttcatc cgtttgggcg ttttctgac ttggaagaac attctctgta ggtttctaag     3600
tgtacagagc cggaactgcc tcgtggttcc tgggcttcag ggaagacaaa tatggaagtc    3660
```

```
aacagccagt tctgccttg agagcatttg caagaatgct ggccttgaat tctgaaatga    3720
cagtgtatct actgccttgt agcaaaataa agctatcctc ttattttaca tacttcc       3777

<210> SEQ ID NO 2
<211> LENGTH: 3420
<212> TYPE: DNA
<213> ORGANISM: Mus musculus

<400> SEQUENCE: 2
gggagtgtcc aaacctcttt gtttgatggc atctgtttac agagttacac tttaatatca     60
acctgtttcc tcctcctcct tctcctcctt ctcctcctcc tcctcggtga cctccttctc    120
ctcccctttc tccggagaaa cttcgccccg gcggtgcgga gcgccgctgc gcagccgggg    180
gaggacgcag gcaaggcgga gggcagcggg aggcggcaac cggtgcggtc cccggggctc    240
ttggcggagc cccggcccgc ctcgccatgg cccggagacc ccgacacagc atctacagta    300
gcgatgaaga tgatgaagac attgagatgt gtgaccatga ctacgatggg ctgctgccca    360
aatctggaaa gcgtcacttg gggaaaacta ggtggacaag ggaagaggat gagaagctga    420
agaagctggt ggaacagaac ggaacagacg actggaaagt cattgccaat tatctgccca    480
accggacaga tgtgcagtgc aacaccggt ggcagaaagt gctgaaccct gaactcatca    540 aggtccctg accaaagaa aagatcaga gagtcataga gcttgtccag aaatatggtc    600
cgaagcgttg gtctgttatt gccaagcact aaaagggag aattggaaag cagtgtcggg    660
agaggtggca caaccatttg aatccagaag ttaagaaaac ctcctggaca gaagaggagg    720
acagaatcat ttaccaggca cacaagcgtc tggggaacag atgggcagag atcgcaaagc    780
tgctgcccgg acggactgat aatgctatca agaaccactg gaattccacc atgcgtcgca    840
aggtggaaca ggaaggctac ctgcaggagc cttccaaagc cagccagacg ccagtggcca    900
cgagcttcca gaagaacaat catttgatgg ggtttgggca tgcctcacct ccatctcagc    960
tctctccaag tggccagtcc tccgtcaaca gcgaatatcc ctattaccac atcgccgaag   1020
cacaaaacat ctccagtcac gttccctatc ctgtcgcatt gcatgttaat atagtcaacg   1080
tccctcagcc ggctgcggca gccatccaga gacactataa cgacgaagac cctgagaagg   1140
aaaagcgaat aaaggagctg gagttgctcc tgatgtcaac agagaacgag ctgaagggac   1200
agcaggcatt accaacacag aaccacactt gcagctaccc cgggtggcac agcacctcca   1260
ttgtggacca gaccagacct catggggata gtgcacctgt ttcctgtttg ggagaacacc   1320
atgccacccc atctctgcct gcagatcccg gctcctacc tgaagaaagt gcctcaccag   1380
caaggtgcat gatcgtccac cagggcacca ttctggacaa tgttaagaac ctcttagaat   1440
ttgcagaaac actccagttt atagattctt tcttgaacac ttccagcaac catgaaagct   1500
cgggcttaga tgcacctacc ttaccctcca ctcctctcat tggtcacaaa ctgacaccat   1560
gtcgagacca gactgtgaaa acccagaagg aaaattccat ctttagaact ccagctatca   1620
aaaggtcaat cctcgaaagc tctcctcgaa ctcccacacc attcaaacat gcccttgcag   1680
ctcaagaaat taaatacggt cccctgaaga tgctacctca gaccccctcc catgcagtgg   1740
aggacctaca agatgtgatt aagcaggaat cggatgaatc tggaattgtg ctgagtttc   1800 aagagagtgg accaccgtta ctgaaaaaaa tcaagcagga ggtggagtcg ccaactgaga   1860
aatcgggaaa cttcttctgc tcaaaccact gggcagagaa cagcctgagc acccagctgt   1920
tctcgcaggc gtcctgtgtg gcagatgccc caaatattct tacaagctct gtttaatga   1980
```

```
cacctgtatc agaagatgaa gacaatgtcc tcaaagcctt taccgtacct aagaacaggc   2040
ccctggtggg tcccttgcag ccatgcagtg gtgcctggga ccagcatcc  tgtgggaaga   2100 cagaggacca gatgacggcc tccggtccgg ctcggaaata cgtgaacgcg ttctcagctc   2160
gaactctggt catgtgagac atttccagaa aagcattatg gttttcagaa cacttaaaag   2220
ttgactttcg acacatggct cctcagcgtg gagcgctcca tggctgagag aagagcctga   2280
ttttgttgtg gtacaacagt tgagagcagc accaagtgca tttttagttg cttgagatct   2340
cacttgattt cacacaacta aaaggatttt tttttttaa  aataataat  aatgaataac   2400 agtcttacct aaattattag gtaatgaatt gtgaccattt gttaatatca taatcagatt   2460
ttttaaaaaa aataaaatga tttatttgta ttttagagga tacaacagat cagtattttt   2520
gactgtggtg aatttaaaaa aaaaatttac acaagaaat  atcccagtat tccatgtatc   2580
tcagtcacta aacatacaca gagagatttt taaaaaccag gagaagcatt attttgaatg   2640
ttagctaaat cccaagtaat acttaatgca accctctagg agctcatttg tggctaataa   2700
tcttggaaat atctttatta tactaaacca tttcatgagg agaattttgt tgtcagcttg   2760
cttgaaaagt tattactgta tgaaatagtt ttattgaaaa aattatattt ttattcagta   2820 atttaattt  gtaaatgcca aatggagaaa tgtgttcgct gctatggttt tagcctgtag   2880
tcatgctgct agctagtgtc aggggggcaat agagcttaga tggaaaaaag agaaagagac   2940
tcggtgttag ataacggact atgcactagt attccagact tttttatttt tatatatatg   3000
taccttttcc ttttgtaatt ggaaaactta tttgggagaa ttttgcatt  gttgtacatt   3060 tttgtttttt aggattttt  tttttgttg ttattgtcga tttataaaag cattgcactt   3120 cttttcttt tttgggaga  tttgtgttgt ttatgtcata tgttttgttt tgagttcagc   3180
ctgaatgttc atccgtttgg gcgttttctct gacttggaag aacattctct gtaggtttct   3240
aagtgtacag agccggaact gcctcgtggt tcctgggctt cagggaagac aaatatggaa   3300
gtcaacagcc agtttctgcc ttgagagcat ttgcaagaat gctggccttg aattctgaaa   3360
tgacagtgta tctactgcct tgtagcaaaa taaagctatc ctcttatttt acatacttcc   3420
```

<210> SEQ ID NO 3
<211> LENGTH: 755
<212> TYPE: PRT
<213> ORGANISM: Mus musculus

<400> SEQUENCE: 3

```
Met Ala Arg Arg Pro Arg His Ser Ile Tyr Ser Ser Asp Glu Asp Asp
1               5                   10                  15

Glu Asp Ile Glu Met Cys Asp His Asp Tyr Asp Gly Leu Leu Pro Lys
            20                  25                  30

Ser Gly Lys Arg His Leu Gly Lys Thr Arg Trp Thr Arg Glu Glu Asp
        35                  40                  45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
        115                 120                 125
```

```
Gln Cys Arg Glu Arg Trp His Asn His Leu Asn Pro Glu Val Lys Lys
    130                 135                 140

Thr Ser Trp Thr Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Glu Pro Ser Lys Ala Ser Gln Thr
        195                 200                 205

Pro Val Ala Thr Ser Phe Gln Lys Asn Asn His Leu Met Gly Phe Gly
210                 215                 220

His Ala Ser Pro Pro Ser Gln Leu Ser Pro Ser Gly Gln Ser Ser Val
225                 230                 235                 240

Asn Ser Glu Tyr Pro Tyr Tyr His Ile Ala Glu Ala Gln Asn Ile Ser
                245                 250                 255

Ser His Val Pro Tyr Pro Val Ala Leu His Val Asn Ile Val Asn Val
            260                 265                 270

Pro Gln Pro Ala Ala Ala Ile Gln Arg His Tyr Asn Asp Glu Asp
        275                 280                 285

Pro Glu Lys Glu Lys Arg Ile Lys Glu Leu Glu Leu Leu Leu Met Ser
290                 295                 300

Thr Glu Asn Glu Leu Lys Gly Gln Gln Ala Leu Pro Thr Gln Asn His
305                 310                 315                 320

Thr Cys Ser Tyr Pro Gly Trp His Ser Thr Ser Ile Val Asp Gln Thr
                325                 330                 335

Arg Pro His Gly Asp Ser Ala Pro Val Ser Cys Leu Gly Glu His His
            340                 345                 350

Ala Thr Pro Ser Leu Pro Ala Asp Pro Gly Ser Leu Pro Glu Glu Ser
        355                 360                 365

Ala Ser Pro Ala Arg Cys Met Ile Val His Gln Gly Thr Ile Leu Asp
370                 375                 380

Asn Val Lys Asn Leu Leu Glu Phe Ala Glu Thr Leu Gln Phe Ile Asp
385                 390                 395                 400

Ser Asp Ser Ser Trp Cys Asp Leu Ser Ser Phe Glu Phe Ser Glu Glu
                405                 410                 415

Ala Ala Ala Phe Ser Pro Ser Gln Gln Pro Thr Gly Lys Ala Phe Gln
            420                 425                 430

Leu Gln Gln Arg Glu Gly His Gly Thr Arg Ser Ala Gly Glu Pro Ser
        435                 440                 445

Leu Arg Val Thr Arg Arg Val Leu Ser Glu Ala Ser Leu Gly Pro Asp
450                 455                 460

Ser Pro Gln Ala Arg His Ser Lys Val Pro Leu Val Val Leu Arg Lys
465                 470                 475                 480

Arg Arg Gly Gln Ala Ser Pro Leu Ala Ala Gly Glu Pro Ser Pro Ser
                485                 490                 495

Leu Phe Ala Asp Val Ile Ser Ser Thr Leu Lys Arg Ser Pro Val Lys
            500                 505                 510

Ser Leu Pro Phe Ser Pro Ser Gln Phe Leu Asn Thr Ser Ser Asn His
        515                 520                 525

Glu Ser Ser Gly Leu Asp Ala Pro Thr Leu Pro Ser Thr Pro Leu Ile
530                 535                 540
```

Gly His Lys Leu Thr Pro Cys Arg Asp Gln Thr Val Lys Thr Gln Lys
545                 550                 555                 560

Glu Asn Ser Ile Phe Arg Thr Pro Ala Ile Lys Arg Ser Ile Leu Glu
                565                 570                 575

Ser Ser Pro Arg Thr Pro Thr Pro Phe Lys His Ala Leu Ala Ala Gln
            580                 585                 590

Glu Ile Lys Tyr Gly Pro Leu Lys Met Leu Pro Gln Thr Pro Ser His
        595                 600                 605

Ala Val Glu Asp Leu Gln Asp Val Ile Lys Gln Ser Asp Glu Ser
    610                 615                 620

Gly Ile Val Ala Glu Phe Gln Glu Ser Gly Pro Pro Leu Leu Lys Lys
625                 630                 635                 640

Ile Lys Gln Glu Val Glu Ser Pro Thr Glu Lys Ser Gly Asn Phe Phe
                645                 650                 655

Cys Ser Asn His Trp Ala Glu Asn Ser Leu Ser Thr Gln Leu Phe Ser
            660                 665                 670

Gln Ala Ser Pro Val Ala Asp Ala Pro Asn Ile Leu Thr Ser Ser Val
        675                 680                 685

Leu Met Thr Pro Val Ser Glu Asp Glu Asp Asn Val Leu Lys Ala Phe
690                 695                 700

Thr Val Pro Lys Asn Arg Pro Leu Val Gly Pro Leu Gln Pro Cys Ser
705                 710                 715                 720

Gly Ala Trp Glu Pro Ala Ser Cys Gly Lys Thr Glu Asp Gln Met Thr
                725                 730                 735

Ala Ser Gly Pro Ala Arg Lys Tyr Val Asn Ala Phe Ser Ala Arg Thr
            740                 745                 750

Leu Val Met
    755

<210> SEQ ID NO 4
<211> LENGTH: 636
<212> TYPE: PRT
<213> ORGANISM: Mus musculus

<400> SEQUENCE: 4

Met Ala Arg Arg Pro Arg His Ser Ile Tyr Ser Ser Asp Glu Asp Asp
1               5                   10                  15

Glu Asp Ile Glu Met Cys Asp His Asp Tyr Asp Gly Leu Leu Pro Lys
            20                  25                  30

Ser Gly Lys Arg His Leu Gly Lys Thr Arg Trp Thr Arg Glu Glu Asp
        35                  40                  45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
        115                 120                 125

Gln Cys Arg Glu Arg Trp His Asn His Leu Asn Pro Glu Val Lys Lys
    130                 135                 140

Thr Ser Trp Thr Glu Glu Glu Asp Arg Ile Ile Tyr Gln Ala His Lys
145                 150                 155                 160

```
Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Pro Ser Lys Ala Ser Gln Thr
        195                 200                 205

Pro Val Ala Thr Ser Phe Gln Lys Asn Asn His Leu Met Gly Phe Gly
    210                 215                 220

His Ala Ser Pro Pro Ser Gln Leu Ser Pro Ser Gly Gln Ser Ser Val
225                 230                 235                 240

Asn Ser Glu Tyr Pro Tyr His Ile Ala Glu Ala Gln Asn Ile Ser
                245                 250                 255

Ser His Val Pro Tyr Pro Val Ala Leu His Val Asn Ile Val Asn Val
            260                 265                 270

Pro Gln Pro Ala Ala Ala Ile Gln Arg His Tyr Asn Asp Glu Asp
        275                 280                 285

Pro Glu Lys Glu Lys Arg Ile Lys Glu Leu Glu Leu Leu Met Ser
    290                 295                 300

Thr Glu Asn Glu Leu Lys Gly Gln Gln Ala Leu Pro Thr Gln Asn His
305                 310                 315                 320

Thr Cys Ser Tyr Pro Gly Trp His Ser Thr Ser Ile Val Asp Gln Thr
                325                 330                 335

Arg Pro His Gly Asp Ser Ala Pro Val Ser Cys Leu Gly Glu His His
            340                 345                 350

Ala Thr Pro Ser Leu Pro Ala Asp Pro Gly Ser Leu Pro Glu Glu Ser
        355                 360                 365

Ala Ser Pro Ala Arg Cys Met Ile Val His Gln Gly Thr Ile Leu Asp
    370                 375                 380

Asn Val Lys Asn Leu Leu Glu Phe Ala Glu Thr Leu Gln Phe Ile Asp
385                 390                 395                 400

Ser Phe Leu Asn Thr Ser Ser Asn His Glu Ser Ser Gly Leu Asp Ala
                405                 410                 415

Pro Thr Leu Pro Ser Thr Pro Leu Ile Gly His Lys Leu Thr Pro Cys
            420                 425                 430

Arg Asp Gln Thr Val Lys Thr Gln Lys Glu Asn Ser Ile Phe Arg Thr
        435                 440                 445

Pro Ala Ile Lys Arg Ser Ile Leu Glu Ser Ser Pro Arg Thr Pro Thr
    450                 455                 460

Pro Phe Lys His Ala Leu Ala Ala Gln Glu Ile Lys Tyr Gly Pro Leu
465                 470                 475                 480

Lys Met Leu Pro Gln Thr Pro Ser His Ala Val Glu Asp Leu Gln Asp
                485                 490                 495

Val Ile Lys Gln Glu Ser Asp Glu Ser Gly Ile Val Ala Glu Phe Gln
            500                 505                 510

Glu Ser Gly Pro Pro Leu Leu Lys Ile Lys Gln Glu Val Glu Ser
        515                 520                 525

Pro Thr Glu Lys Ser Gly Asn Phe Phe Cys Ser Asn His Trp Ala Glu
    530                 535                 540

Asn Ser Leu Ser Thr Gln Leu Phe Ser Gln Ala Ser Pro Val Ala Asp
545                 550                 555                 560

Ala Pro Asn Ile Leu Thr Ser Ser Val Leu Met Thr Pro Val Ser Glu
                565                 570                 575
```

```
Asp Glu Asp Asn Val Leu Lys Ala Phe Thr Val Pro Lys Asn Arg Pro
            580                 585                 590

Leu Val Gly Pro Leu Gln Pro Cys Ser Gly Ala Trp Glu Pro Ala Ser
        595                 600                 605

Cys Gly Lys Thr Glu Asp Gln Met Thr Ala Ser Gly Pro Ala Arg Lys
    610                 615                 620

Tyr Val Asn Ala Phe Ser Ala Arg Thr Leu Val Met
625                 630                 635

<210> SEQ ID NO 5
<211> LENGTH: 3681
<212> TYPE: DNA
<213> ORGANISM: Homo sapiens

<400> SEQUENCE: 5
```

| | | | | | |
|---|---|---|---|---|---|
| aatatcaacc | tgtttcctcc | tcctccttct | cctcctcctc | cgtgacctcc | tcctcctctt | 60 |
| tctcctgaga | aacttcgccc | cagcggtgcg | gagcgccgct | cgcagccgg | ggagggacgc | 120 |
| aggcaggcgg | cgggcagcgg | gaggcggcag | cccggtgcgg | tccccgcggc | tctcggcgga | 180 |
| gccccgcgcc | cgccgcgcca | tggcccgaag | accccggcac | agcatatata | gcagtgacga | 240 |
| ggatgatgag | gactttgaga | tgtgtgacca | tgactatgat | gggctgcttc | ccaagtctgg | 300 |
| aaagcgtcac | ttggggaaaa | caaggtggac | ccgggaagag | gatgaaaaac | tgaagaagct | 360 |
| ggtggaacag | aatggaacag | atgactggaa | agttattgcc | aattatctcc | cgaatcgaac | 420 |
| agatgtgcag | tgccagcacc | gatggcagaa | agtactaaac | cctgagctca | tcaagggtcc | 480 |
| ttggaccaaa | gaagaagatc | agagagtgat | agagcttgta | cagaaatacg | gtccgaaacg | 540 |
| ttggtctgtt | attgccaagc | acttaaaggg | gagaattgga | aaacaatgta | gggagaggtg | 600 |
| gcataaccac | ttgaatccag | aagttaagaa | aacctcctgg | acagaagagg | aagacagaat | 660 |
| tatttaccag | gcacacaaga | gactggggaa | cagatgggca | gaaatcgcaa | agctactgcc | 720 |
| tggacgaact | gataatgcta | tcaagaacca | ctggaattct | acaatgcgtc | ggaaggtcga | 780 |
| acaggaaggt | tatctgcagg | agtcttcaaa | agccagccag | ccagcagtgg | ccacaagctt | 840 |
| ccagaagaac | agtcatttga | tgggttttgc | tcaggctccg | cctacagctc | aactccctgc | 900 |
| cactggccag | cccactgtta | caacgactac | ttcctattac | cacatttctg | aagcacaaaa | 960 |
| tgtctccagt | catgttccat | accctgtagc | gttacatgta | aatatagtca | atgtccctca | 1020 |
| gccagctgcc | gcagccattc | agagacacta | taatgatgaa | gaccctgaga | aggaaaagcg | 1080 |
| aataaaggaa | ttagaattgc | tcctaatgtc | aaccgagaat | gagctaaaag | gacagcaggt | 1140 |
| gctaccaaca | cagaaccaca | catgcagcta | ccccgggtgg | cacagcacca | ccattgccga | 1200 |
| ccacaccaga | cctcatggag | acagtgcacc | tgtttcctgt | ttgggagaac | accactccac | 1260 |
| tccatctctg | ccagcggatc | ctggctccct | acctgaagaa | agcgcctcgc | cagcaaggtg | 1320 |
| catgatcgtc | caccagggca | ccattctgga | taatgttaag | aacctcttag | aatttgcaga | 1380 |
| aacactccaa | tttatagatt | ctgattcttc | atcatggtgt | gatctcagca | gttttgaatt | 1440 |
| ctttgaagaa | gcagattttt | cacctagcca | acatcacaca | ggcaaagccc | tacagcttca | 1500 |
| gcaaagagag | ggcaatggga | ctaaacctgc | aggagaacct | agcccaaggg | tgaacaaacg | 1560 |
| tatgttgagt | gagagttcac | ttgacccacc | caaggtctta | cctcctgcaa | ggcacagcac | 1620 |
| aattccactg | gtcatccttc | gaaaaaaacg | gggccaggcc | agccccttag | ccactggaga | 1680 |
| ctgtagctcc | ttcatatttg | ctgacgtcag | cagttcaact | cccaagcgtt | ccctgtcaa | 1740 |
| aagcctaccc | ttctctcccct | cgcagttctt | aaacacttcc | agtaaccatg | aaaactcaga | 1800 |

-continued

```
cttggaaatg ccttctttaa cttccacccc cctcattggt cacaaattga ctgttacaac    1860
accatttcat agagaccaga ctgtgaaaac tcaaaaggaa atactgtttt ttagaacccc    1920
agctatcaaa aggtcaatct tagaaagctc tccaagaact cctacaccat tcaaacatgc    1980
acttgcagct caagaaatta aatacggtcc cctgaagatg ctacctcaga cccctctca    2040 tctagtagaa gatctgcagg atgtgatcaa acaggaatct gatgaatctg gaattgttgc    2100
tgagtttcaa gaaaatggac caccttact gaagaaaatc aaacaagagg tggaatctcc    2160
aactgataaa tcaggaaact tcttctgctc acaccactgg gaaggggaca gtctgaatac    2220
ccaactgttc acgcagacct cgcctgtggc agatgcaccg aatattctta caagctccgt    2280
tttaatggca ccagcatcag aagatgaaga caatgttctc aaagcattta cagtacctaa    2340
aaacaggtcc ctggcgagcc ccttgcagcc ttgtagcagt acctgggaac ctgcatcctg    2400
tggaaagatg gaggagcaga tgacatcttc cagtcaagct cgtaaatacg tgaatgcatt    2460
ctcagcccgg acgctggtca tgtgagacat ttccagaaaa gcattatggt tttcagaaca    2520
cttcaagttg acttgggata tcattcct caacatgaaa cttttcatga atgggagaag    2580
aacctatttt tgttgtggta caacagttga gagcagcacc aagtgcattt agttgaatga    2640
agtcttcttg gatttcaccc aactaaaagg attttaaaa ataataaca gtcttaccta    2700 aattattagg taatgaattg tagccagttg ttaatatctt aatgcagatt ttttaaaaa    2760 aaacataaaa tgatttatct gtattttaaa ggatccaaca gatcagtatt ttttcctgtg    2820
atgggttttt tgaaatttga cacattaaaa ggtactccag tatttcactt ttctcgatca    2880
ctaaacatat gcatatattt ttaaaaatca gtaaaagcat tactctaagt gtagacttaa    2940
taccatgtga catttaatcc agattgtaaa tgctcattta tggttaatga cattgaaggt    3000
acatttattg taccaaacca ttttatgagt tttctgttag cttgctttaa aaattattac    3060
tgtaagaaat agttttataa aaattatat ttttattcag taatttaatt ttgtaaatgc    3120
caaatgaaaa acgtttttg ctgctatggt cttagcctgt agacatgctg ctagtatcag    3180
aggggcagta gagcttggac agaaagaaaa gaaacttggt gttaggtaat tgactatgca    3240
ctagtatttc agactttta attttatata tatacatt tttttttcctt ctgcaataca    3300 tttgaaaact tgtttgggag actctgcatt ttttattgtg gttttttttgt tattgttggt    3360 ttatacaagc atgcgttgca cttctttttt gggagatgtg tgttgttgat gttctatgtt    3420
ttgttttgag tgtagcctga ctgttttata atttgggagt tctgcatttg atccgcatcc    3480
cctgtggttt ctaagtgtat ggtctcagaa ctgttgcatg gatcctgtgt ttgcaactgg    3540
ggagacagaa actgtggttg atagccagtc actgccttaa gaacatttga tgcaagatgg    3600
ccagcactga acttttgaga tatgacggtg tacttactgc cttgtagcaa aataaagatg    3660
tgcccttatt ttacctacaa a                                              3681
```

<210> SEQ ID NO 6
<211> LENGTH: 3342
<212> TYPE: DNA
<213> ORGANISM: Homo sapiens

<400> SEQUENCE: 6

```
aatatcaacc tgtttcctcc tcctccttct cctcctcctc cgtgacctcc tcctcctctt      60
tctcctgaga aacttcgccc cagcggtgcg gagcgccgct cgcagccgg ggagggacgc     120 aggcaggcgg cgggcagcgg gaggcggcag cccggtgcgg tccccgcggc tctcggcgga    180
```

-continued

```
gccccgcgcc cgccgcgcca tggcccgaag accccggcac agcatatata gcagtgacga    240
ggatgatgag gactttgaga tgtgtgacca tgactatgat gggctgcttc ccaagtctgg    300
aaagcgtcac ttggggaaaa caaggtggac ccgggaagag gatgaaaaac tgaagaagct    360
ggtggaacaa aatggaacag atgactggaa agttattgcc aattatctcc cgaatcgaac    420
agatgtgcag tgccagcacc gatggcagaa agtactaaac cctgagctca tcaagggtcc    480
ttggaccaaa gaagaagatc agagagtgat agagcttgta cagaaatacg gtccgaaacg    540
ttggtctgtt attgccaagc acttaaaggg gagaattgga aaacaatgta gggagaggtg    600
gcataaccac ttgaatccag aagttaagaa aacctcctgg acagaagagg aagacagaat    660
tatttaccag gcacacaaga gactggggaa cagatgggca gaaatcgcaa agctactgcc    720
tggacgaact gataatgcta tcaagaacca ctggaattct acaatgcgtc ggaaggtcga    780
acaggaaggt tatctgcagg agtcttcaaa agccagccag ccagcagtgg ccacaagctt    840
ccagaagaac agtcatttga tgggttttgc tcaggctccg cctacagctc aactccctgc    900
cactggccag cccactgtta acaacgacta ttcctattac acatttctg aagcacaaaa     960 tgtctccagt catgttccat accctgtagc gttacatgta aatatagtca atgtccctca   1020
gccagctgcc gcagccattc agagacacta taatgatgaa gaccctgaga aggaaaagcg   1080
aataaaggaa ttagaattgc tcctaatgtc aaccgagaat gagctaaaag gacagcaggt   1140
gctaccaaca cagaaccaca catgcagcta ccccgggtgg cacagcacca ccattgccga   1200
ccacaccaga cctcatggag acagtgcacc tgtttcctgt ttgggagaac accactccac   1260
tccatctctg ccagcggatc ctggctccct acctgaagaa agcgcctcgc cagcaaggtg   1320
catgatcgtc caccagggca ccattctgga taatgttaag aacctcttag aatttgcaga   1380
aacactccaa tttatagatt ctttcttaaa cacttccagt aaccatgaaa actcagactt   1440
ggaaatgcct tctttaactt ccacccccct cattggtcac aaattgactg ttacaacacc   1500
atttcataga gaccagactg tgaaaactca aaaggaaaat actgttttta gaaccccagc   1560
tatcaaaagg tcaatcttag aaagctctcc aagaactcct acaccattca aacatgcact   1620
tgcagctcaa gaaattaaat acggtcccct gaagatgcta cctcagacac cctctcatct   1680
agtagaagat ctgcaggatg tgatcaaaca ggaatctgat gaatctggaa ttgttgctga   1740
gtttcaagaa aatggaccac ccttactgaa gaaaatcaaa caagaggtgg aatctccaac   1800
tgataaatca ggaaacttct tctgctcaca ccactgggaa ggggacagtc tgaatacca    1860 actgttcacg cagacctcgc ctgtggcaga tgcaccgaat attcttacaa gctccgtttt   1920
aatggcacca gcatcagaag atgaagacaa tgttctcaaa gcatttacag tacctaaaaa   1980
caggtccctg gcgagcccct tgcagccttg tagcagtacc tgggaacctg catcctgtgg   2040
aaagatggag gagcagatga catcttccag tcaagctcgt aaatacgtga atgcattctc   2100
agcccggacg ctggtcatgt gagacatttc cagaaaagca ttatggtttt cagaacactt   2160
caagttgact tgggatatat cattcctcaa catgaaactt ttcatgaatg ggagaagaac   2220
ctatttttgt tgtggtacaa cagttgagag cagcaccaag tgcatttagt tgaatgaagt   2280
cttcttggat ttcacccaac taaaaggatt tttaaaaata aataacagtc ttacctaaat   2340
tattaggtaa tgaattgtag ccagttgtta atatcttaat gcagatttt ttaaaaaaaa    2400 cataaaatga tttatctgta ttttaaagga tccaacagat cagtattttt tcctgtgatg   2460 ggtttttga aatttgacac attaaaaggt actccagtat ttcactttc tcgatcacta    2520 aacatatgca tatatttta aaaatcagta aaagcattac tctaagtgta gacttaatac   2580
```

| | |
|---|---|
| catgtgacat ttaatccaga ttgtaaatgc tcatttatgg ttaatgacat tgaaggtaca | 2640 |
| tttattgtac caaaccattt tatgagtttt ctgttagctt gctttaaaaa ttattactgt | 2700 |
| aagaaatagt tttataaaaa attatatttt tattcagtaa tttaattttg taaatgccaa | 2760 |
| atgaaaaacg ttttttgctg ctatggtctt agcctgtaga catgctgcta gtatcagagg | 2820 |
| ggcagtagag cttggacaga aagaaaagaa acttggtgtt aggtaattga ctatgcacta | 2880 |
| gtatttcaga ctttttaatt ttatatatat atacattttt tttccttctg caatacattt | 2940 |
| gaaaacttgt ttgggagact ctgcattttt tattgtggtt ttttgttat tgttggttta | 3000 |
| tacaagcatg cgttgcactt cttttttggg agatgtgtgt tgttgatgtt ctatgttttg | 3060 |
| ttttgagtgt agcctgactg ttttataatt tgggagttct gcatttgatc cgcatccct | 3120 |
| gtggtttcta agtgtatggt ctcagaactg ttgcatggat cctgtgtttg caactgggga | 3180 |
| gacagaaact gtggttgata gccagtcact gccttaagaa catttgatgc aagatggcca | 3240 |
| gcactgaact tttgagatat gacggtgtac ttactgcctt gtagcaaaat aaagatgtgc | 3300 |
| ccttatttta cctaaaaaaa aaaaaaaaaa aaaaaaaaa aa | 3342 |

<210> SEQ ID NO 7
<211> LENGTH: 3309
<212> TYPE: DNA
<213> ORGANISM: Homo sapiens

<400> SEQUENCE: 7

| | |
|---|---|
| aatatcaacc tgtttcctcc tcctccttct cctcctcctc cgtgacctcc tcctcctctt | 60 |
| tctcctgaga aacttcgccc cagcggtgcg gagcgccgct gcgcagccgg ggagggacgc | 120 |
| aggcaggcgg cgggcagcgg gaggcggcag cccggtgcgg tccccgcggc tctcggcgga | 180 |
| gccccgcgcc cgccgcgcca tggcccgaag accccggcac agcatatata gcagtgacga | 240 |
| ggatgatgag gactttgaga tgtgtgacca tgactatgat gggctgcttc ccaagtctgg | 300 |
| aaagcgtcac ttggggaaaa caaggtggac ccgggaagag gatgaaaaac tgaagaagct | 360 |
| ggtggaacag aatggaacag atgactggaa agttattgcc aattatctcc cgaatcgaac | 420 |
| agatgtgcag tgccagcacc gatggcagaa agtactaaac cctgagctca tcaagggtcc | 480 |
| ttggaccaaa gaagaagatc agagagtgat agagcttgta cagaaatacg gtccgaaacg | 540 |
| ttggtctgtt attgccaagc acttaaaggg gagaattgga aaacaatgta gggagaggtg | 600 |
| gcataaccac ttgaatccag aagttaagaa aacctcctgg acagaagagg aagacagaat | 660 |
| tatttaccag gcacacaaga gactggggaa cagatgggca gaaatcgcaa agctactgcc | 720 |
| tggacgaact gataatgcta tcaagaacca ctggaattct acaatgcgtc ggaaggtcga | 780 |
| acaggaaggt tatctgcagg agtcttcaaa agccagccag ccagcagtgg ccacaagctt | 840 |
| ccagaagaac agtcatttga tgggttttgc tcaggctccg cctacagctc aactccctgc | 900 |
| cactggccag cccactgtta caacgacta ttcctattac cacatttctg aagcacaaaa | 960 |
| tgtctccagt catgttccat accctgtagc gttacatgta aatatagtca atgtccctca | 1020 |
| gccagctgcc gcagccattc agagacacta taatgatgaa gaccctgaga aggaaaagcg | 1080 |
| aataaaggaa ttagaattgc tcctaatgtc aaccgagaat gagctaaaag gacagcagac | 1140 |
| acagaaccac acatgcagct accccgggtg gcacagcacc accattgccg accacaccag | 1200 |
| acctcatgga gacagtgcac ctgtttcctg tttgggagaa caccactcca ctccatctct | 1260 |
| gccagcggat cctggctccc tacctgaaga aagcgcctcg ccagcaaggt gcatgatcgt | 1320 |

| | | |
|---|---|---|
| ccaccagggc accattctgg ataatgttaa gaacctctta gaatttgcag aaacactcca | 1380 | |
| atttatagat tctttcttaa acacttccag taaccatgaa aactcagact tggaaatgcc | 1440 | |
| ttctttaact tccaccccccc tcattggtca caaattgact gttacaacac catttcatag | 1500 | |
| agaccagact gtgaaaactc aaaaggaaaa tactgttttt agaacccccag ctatcaaaag | 1560 | |
| gtcaatctta gaaagctctc caagaactcc tacaccattc aaacatgcac ttgcagctca | 1620 | |
| agaaattaaa tacggtcccc tgaagatgct acctcagaca ccctctcatc tagtagaaga | 1680 | |
| tctgcaggat gtgatcaaac aggaatctga tgaatctgga attgttgctg agtttcaaga | 1740 | |
| aaatggacca cccttactga gaaaaatcaa acaagaggtg gaatctccaa ctgataaatc | 1800 | |
| aggaaacttc ttctgctcac accactggga aggggacagt ctgaataccc aactgttcac | 1860 | |
| gcagacctcg cctgtggcag atgcaccgaa tattcttaca agctccgttt taatggcacc | 1920 | |
| agcatcagaa gatgaagaca atgttctcaa agcatttaca gtacctaaaa acaggtccct | 1980 | |
| ggcgagcccc ttgcagcctt gtagcagtac ctgggaacct gcatcctgtg gaaagatgga | 2040 | |
| ggagcagatg acatcttcca gtcaagctcg taaatacgtg aatgcattct cagcccggac | 2100 | |
| gctggtcatg tgagacattt ccagaaaagc attatggttt tcagaacact tcaagttgac | 2160 | |
| ttgggatata tcattcctca acatgaaact tttcatgaat gggagaagaa cctatttttg | 2220 | |
| ttgtggtaca acagttgaga gcagcaccaa gtgcatttag ttgaatgaag tcttcttgga | 2280 | |
| tttcacccaa ctaaaaggat ttttaaaaat aaataacagt cttacctaaa ttattaggta | 2340 | |
| atgaattgta gccagttgtt aatatcttaa tgcagatttt tttaaaaaaa acataaaatg | 2400 | |
| atttatctgt attttaaagg atccaacaga tcagtatttt ttcctgtgat gggtttttttg | 2460 | |
| aaatttgaca cattaaaagg tactccagta tttcactttt ctcgatcact aaacatatgc | 2520 | |
| atatattttt aaaaatcagt aaaagcatta ctctaagtgt agacttaata ccatgtgaca | 2580 | |
| tttaatccag attgtaaatg ctcatttatg gttaatgaca ttgaaggtac atttattgta | 2640 | |
| ccaaaccatt ttatgagttt tctgttagct tgctttaaaa attattactg taagaaatag | 2700 | |
| ttttataaaa aattatattt ttattcagta atttaatttt gtaaatgcca aatgaaaaac | 2760 | |
| gttttttgct gctatggtct tagcctgtag acatgctgct agtatcagag gggcagtaga | 2820 | |
| gcttggacag aaagaaaaga aacttggtgt taggtaattg actatgcact agtatttcag | 2880 | |
| acttttttaat tttatatata tatacatttt ttttccttct gcaatacatt tgaaaacttg | 2940 | |
| tttgggagac tctgcatttt ttattgtggt tttttttgtta ttgttggttt atacaagcat | 3000 | |
| gcgttgcact tcttttttgg gagatgtgtg ttgttgatgt tctatgtttt gttttgagtg | 3060 | |
| tagcctgact gttttataat ttgggagttc tgcatttgat ccgcatcccc tgtggtttct | 3120 | |
| aagtgtatgg tctcagaact gttgcatgga tcctgtgttt gcaactgggg agacagaaac | 3180 | |
| tgtggttgat agccagtcac tgccttaaga acatttgatg caagatggcc agcactgaac | 3240 | |
| ttttgagata tgacggtgta cttactgcct tgtagcaaaa taaagatgtg cccttatttt | 3300 | |
| acctacaaa | 3309 | |

<210> SEQ ID NO 8
<211> LENGTH: 3669
<212> TYPE: DNA
<213> ORGANISM: Homo sapiens

<400> SEQUENCE: 8

| | | |
|---|---|---|
| aatatcaacc tgtttcctcc tcctccttct cctcctcctc cgtgacctcc tcctcctctt | 60 | |
| tctcctgaga aacttcgccc cagcggtgcg gagcgccgct gcgcagccgg ggagggacgc | 120 | |

```
aggcaggcgg cgggcagcgg gaggcggcag cccggtgcgg tccccgcggc tctcggcgga    180
gccccgcgcc cgccgcgcca tggcccgaag accccggcac agcatatata gcagtgacga    240
ggatgatgag gactttgaga tgtgtgacca tgactatgat gggctgcttc ccaagtctgg    300
aaagcgtcac ttggggaaaa caaggtggac ccgggaagag gatgaaaaac tgaagaagct    360
ggtggaacag aatggaacag atgactggaa agttattgcc aattatctcc cgaatcgaac    420
agatgtgcag tgccagcacc gatggcagaa agtactaaac cctgagctca tcaagggtcc    480
ttggaccaaa gaagaagatc agagagtgat agagcttgta cagaaatacg gtccgaaacg    540
ttggtctgtt attgccaagc acttaaaggg gagaattgga aaacaatgta gggagaggtg    600
gcataaccac ttgaatccag aagttaagaa aacctcctgg acagaagagg aagacagaat    660
tatttaccag gcacacaaga gactggggaa cagatgggca gaaatcgcaa agctactgcc    720
tggacgaact gataatgcta tcaagaacca ctggaattct acaatgcgtc ggaaggtcga    780
acaggaaggt tatctgcagg agtcttcaaa agccagccag ccagcagtgg ccacaagctt    840
ccagaagaac agtcatttga tgggttttgc tcaggctccg cctacagctc aactccctgc    900
cactggccag cccactgtta acaacgacta ttcctattac acatttctg  aagcacaaaa    960 tgtctccagt catgttccat accctgtagc gttacatgta aatatagtca atgtccctca   1020
gccagctgcc gcagccattc agagacacta taatgatgaa gaccctgaga aggaaaagcg   1080
aataaaggaa ttagaattgc tcctaatgtc aaccgagaat gagctaaaag gacagcagac   1140
acagaaccac acatgcagct accccgggtg gcacagcacc accattgccg accacaccag   1200
acctcatgga gacagtgcac ctgtttcctg tttgggagaa caccactcca ctccatctct   1260
gccagcggat cctggctccc tacctgaaga aagcgcctcg ccagcaaggt gcatgatcgt   1320
ccaccagggc accattctgg ataatgttaa gaacctctta gaatttgcag aaacactcca   1380
atttatagat tctgattctt catcatggtg tgatctcagc agttttgaat tctttgaaga   1440
agcagatttt tcacctagcc aacatcacac aggcaaagcc ctacagcttc agcaaagaga   1500
gggcaatggg actaaacctg caggagaacc tagcccaagg gtgaacaaac gtatgttgag   1560
tgagagttca cttgacccac ccaaggtctt acctcctgca aggcacagca caattccact   1620
ggtcatcctt cgaaaaaaac ggggccaggc cagcccctta gccactggag actgtagctc   1680
cttcatattt gctgacgtca gcagttcaac tcccaagcgt tcccctgtca aaagcctacc   1740
cttctctccc tcgcagttct taaacacttc cagtaaccat gaaaactcag acttggaaat   1800
gccttcttta acttccaccc ccctcattgg tcacaaattg actgttacaa caccatttca   1860
tagagaccag actgtgaaaa ctcaaaagga aaatactgtt tttagaaccc agctatcaa    1920 aaggtcaatc ttagaaagct ctccaagaac tcctacacca ttcaaacatg cacttgcagc   1980
tcaagaaatt aaatacggtc ccctgaagat gctacctcag acaccctctc atctagtaga   2040
agatctgcag gatgtgatca acaggaatc  tgatgaatct ggaattgttg ctgagtttca   2100
agaaaatgga ccacccttac tgaagaaaat caaacaagag gtggaatctc caactgataa   2160
atcaggaaac ttcttctgct cacaccactg gaaggggac  agtctgaata cccaactgtt   2220
cacgcagacc tcgcctgtgg cagatgcacc gaatattctt acaagctccg ttttaatggc   2280
accagcatca gaagatgaag acaatgttct caaagcattt acagtaccta aaaacaggtc   2340
cctggcgagc cccttgcagc cttgtagcag tacctgggaa cctgcatcct gtggaaagat   2400
ggaggagcag atgacatctt ccagtcaagc tcgtaaatac gtgaatgcat tctcagcccg   2460
```

```
gacgctggtc atgtgagaca tttccagaaa agcattatgg ttttcagaac acttcaagtt      2520
gacttgggat atatcattcc tcaacatgaa acttttcatg aatgggagaa gaacctattt      2580
ttgttgtggt acaacagttg agagcagcac caagtgcatt tagttgaatg aagtcttctt      2640
ggatttcacc caactaaaag gattttttaaa aataaataac agtcttacct aaattattag     2700
gtaatgaatt gtagccagtt gttaatatct taatgcagat ttttttaaaa aaaacataaa      2760
atgatttatc tgtattttaa aggatccaac agatcagtat ttttttcctgt gatgggtttt     2820 ttgaaatttg acacattaaa aggtactcca gtatttcact tttctcgatc actaaacata     2880
tgcatatatt tttaaaaatc agtaaaagca ttactctaag tgtagactta ataccatgtg     2940
acatttaatc cagattgtaa atgctcattt atggttaatg acattgaagg tacatttatt     3000
gtaccaaacc atttatgag ttttctgtta gcttgcttta aaattatta ctgtaagaaa      3060 tagttttata aaaattata ttttattca gtaatttaat tttgtaaatg ccaaatgaaa      3120
aacgtttttt gctgctatgg tcttagcctg tagacatgct gctagtatca gagggggcagt    3180 agagcttgga cagaaagaaa agaaacttgg tgttaggtaa ttgactatgc actagtattt    3240 cagactttt aatttatat atatatacat ttttttttcct tctgcaatac atttgaaaac     3300
ttgtttggga gactctgcat ttttttattgt ggttttttttg ttattgttgg tttatacaag   3360
catgcgttgc acttctttt tgggagatgt gtgttgttga tgttctatgt tttgttttga    3420
gtgtagcctg actgttttat aatttgggag ttctgcattt gatccgcatc ccctgtggtt    3480
tctaagtgta tggtctcaga actgttgcat ggatcctgtg tttgcaactg gggagacaga    3540
aactgtggtt gatagccagt cactgcctta agaacatttg atgcaagatg gccagcactg    3600
aacttttgag atatgacggt gtacttactg ccttgtagca aaataaagat gtgcccttat    3660
tttacctac                                                              3669
```

<210> SEQ ID NO 9
<211> LENGTH: 3060
<212> TYPE: DNA
<213> ORGANISM: Homo sapiens

<400> SEQUENCE: 9

```
aatatcaacc tgtttcctcc tcctccttct cctcctcctc cgtgacctcc tcctcctctt     60
tctcctgaga aacttcgccc cagcggtgcg gagcgccgct cgcagccgg ggagggacgc      120 aggcaggcgg cgggcagcgg gaggcggcag cccggtgcgg tccccgcggc tctcggcgga     180
gccccgcgcc cgccgcgcca tggcccgaag accccggcac agcatatata gcagtgacga    240
ggatgatgag gactttgaga tgtgtgacca tgactatgat gggctgcttc ccaagtctgg     300
aaagcgtcac ttggggaaaa caaggtggac ccgggaagag gatgaaaaac tgaagaagct     360
ggtggaacag aatggaacag atgactggaa agttattgcc aattatctcc cgaatcgaac     420
agatgtgcag tgccagcacc gatggcagaa agtactaaac cctgagctca tcaagggtcc     480
ttggaccaaa gaagaagatc agagagtgat agagcttgta cagaaatacg gtccgaaacg     540
ttggtctgtt attgccaagc acttaaaggg gagaattgga aaacaatgta gggagaggtg     600
gcataaccac ttgaatccag aagttaagaa aacctcctgg acagaagagg aagacagaat     660
tatttaccag gcacacaaga gactggggaa cagatgggca gaaatcgcaa agctactgcc     720
tggacgaact gataatgcta tcaagaacca ctggaattct acaatgcgtc ggaaggtcga     780
acaggaaggt tatctgcagg agtcttcaaa agccagccag ccagcagtgg ccacaagctt     840
ccagaagaac agtcatttga tgggttttgc tcaggctccg cctacagctc aactccctgc     900
```

```
cactggccag cccactgtta acaacgacta ttcctattac cacatttctg aagcacaaaa    960
tgtctccagt catgttccat accctgtagc gttacatgta aatatagtca atgtccctca   1020
gccagctgcc gcagccattc agagacacta taatgatgaa gaccctgaga aggaaaagcg   1080
aataaaggaa ttagaattgc tcctaatgtc aaccgagaat gagctaaaag acagcaggt   1140
gctaccattc ttaaacactt ccagtaacca tgaaaactca gacttggaaa tgccttcttt   1200
aacttccacc ccctcattg gtcacaaatt gactgttaca acaccatttc atagagacca   1260
gactgtgaaa actcaaaagg aaaatactgt ttttagaacc ccagctatca aaggtcaat   1320
cttagaaagc tctccaagaa ctcctacacc attcaaacat gcacttgcag ctcaagaaat   1380
taaatacggt cccctgaaga tgctacctca gacaccctct catctagtag aagatctgca   1440
ggatgtgatc aaacaggaat ctgatgaatc tggaattgtt gctgagtttc aagaaaatgg   1500
accacccta ctgaagaaaa tcaaacaaga ggtggaatct ccaactgata aatcaggaaa   1560
cttcttctgc tcacaccact gggaagggga cagtctgaat acccaactgt tcacgcagac   1620
ctcgcctgtg gcagatgcac cgaatattct tacaagctcc gttttaatgg caccagcatc   1680
agaagatgaa gacaatgttc tcaaagcatt tacagtacct aaaaacaggt ccctggcgag   1740
cccttgcag ccttgtagca gtacctggga acctgcatcc tgtggaaaga tggaggagca   1800
gatgacatct tccagtcaag ctcgtaaata cgtgaatgca ttctcagccc ggacgctggt   1860
catgtgagac atttccagaa aagcattatg gttttcagaa cacttcaagt tgacttggga   1920
tatatcattc ctcaacatga aacttttcat gaatgggaga agaacctatt tttgttgtgg   1980
tacaacagtt gagagcagca ccaagtgcat ttagttgaat gaagtcttct tggatttcac   2040
ccaactaaaa ggatttttaa aaataaataa cagtcttacc taaattatta ggtaatgaat   2100
tgtagccagt tgttaatatc ttaatgcaga ttttttaaa aaaacataa aatgatttat   2160
ctgtatttta aaggatccaa cagatcagta tttttttcctg tgatgggttt tttgaaattt   2220
gacacattaa aaggtactcc agtatttcac ttttctcgat cactaaacat atgcatatat   2280
ttttaaaaat cagtaaaagc attactctaa gtgtagactt aataccatgt gacatttaat   2340
ccagattgta aatgctcatt tatggttaat gacattgaag gtacatttat tgtaccaaac   2400
catttttatga gttttctgtt agcttgcttt aaaaattatt actgtaagaa atagttttat   2460
aaaaaattat attttttatc agtaatttaa ttttgtaaat gccaaatgaa aaacgttttt   2520
tgctgctatg gtcttagcct gtagacatgc tgctagtatc agaggggcag tagagcttgg   2580
acagaaagaa aagaaacttg gtgttaggta attgactatg cactagtatt tcagactttt   2640
taatttata tatatataca tttttttcc ttctgcaata catttgaaaa cttgtttggg   2700
agactctgca ttttttattg tggtttttt gttattgttg gttatacaa gcatgcgttg   2760
cacttctttt ttgggagatg tgtgttgttg atgttctatg ttttgttttg agtgtagcct   2820
gactgtttta taatttggga gttctgcatt tgatccgcat cccctgtggt ttctaagtgt   2880
atggtctcag aactgttgca tggatcctgt gtttgcaact ggggagacag aaactgtggt   2940
tgatagccag tcactgcctt aagaacattt gatgcaagat ggccagcact gaacttttga   3000
gatatgacgg tgtacttact gccttgtagc aaaataaaga tgtgccctta ttttacctac   3060
```

<210> SEQ ID NO 10
<211> LENGTH: 3630
<212> TYPE: DNA
<213> ORGANISM: Homo sapiens

<400> SEQUENCE: 10

```
aatatcaacc tgtttcctcc tcctccttct cctcctcctc cgtgacctcc tcctcctctt      60
tctcctgaga aacttcgccc cagcggtgcg gagcgccgct gcgcagccgg ggagggacgc     120
aggcaggcgg cgggcagcgg gaggcggcag cccggtgcgg tccccgcggc tctcggcgga     180
gccccgcgcc cgccgcgcca tggcccgaag accccggcac agcatatata gcagtgacga     240
ggatgatgag gactttgaga tgtgtgacca tgactatgat gggctgcttc ccaagtctgg     300
aaagcgtcac ttggggaaaa caaggtggac ccgggaagag gatgaaaaac tgaagaagct     360
ggtggaacag aatggaacag atgactggaa agttattgcc aattatctcc cgaatcgaac     420
agatgtgcag tgccagcacc gatggcagaa agtactaaac cctgagctca tcaagggtcc     480
ttggaccaaa gaagaagatc agagagtgat agagcttgta cagaaatacg gtccgaaacg     540
ttggtctgtt attgccaagc acttaaaggg gagaattgga aaacaatgta gggagaggtg     600
gcataaccac ttgaatccag aagttaagaa aacctcctgg acagaagagg aagacagaat     660
tatttaccag gcacacaaga gactggggaa cagatgggca gaaatcgcaa agctactgcc     720
tggacgaact gataatgcta tcaagaacca ctggaattct acaatgcgtc ggaaggtcga     780
acaggaaggt tatctgcagg agtcttcaaa agccagccag ccagcagtgg ccacaagctt     840
ccagaagaac agtcatttga tgggttttgc tcaggctccg cctacagctc aactccctgc     900
cactggccag cccactgtta acaacgacta ttcctattac cacatttctg aagcacaaaa     960
tgtctccagt catgttccat accctgtagc gttacatgta aatatagtca atgtccctca    1020
gccagctgcc gcagccattc agagacacta taatgatgaa gaccctgaga aggaaaagcg    1080
aataaaggaa ttagaattgc tcctaatgtc aaccgagaat gagctaaaag gacagcaggt    1140
gctaccaaca cagaaccaca catgcagcta ccccgggtgg cacagcacca ccattgccga    1200
ccacaccaga cctcatggag acagtgcacc tgtttcctgt ttgggagaac accactccac    1260
tccatctctg ccagcggatc ctggctccct acctgaagaa agcgcctcgc cagcaaggtg    1320
catgatcgtc caccagggca ccattctgga taatgattct tcatcatggt gtgatctcag    1380
cagttttgaa ttctttgaag aagcagattt ttcacctagc caacatcaca caggcaaagc    1440
cctacagctt cagcaaagag agggcaatgg gactaaacct gcaggagaac ctagcccaag    1500
ggtgaacaaa cgtatgttga gtgagagttc acttgaccca cccaaggtct acctcctgc     1560
aaggcacagc acaattccac tggtcatcct tcgaaaaaaa cggggccagg ccagcccctt    1620
agccactgga gactgtagct ccttcatatt tgctgacgtc agcagttcaa ctcccaagcg    1680
ttcccctgtc aaaagcctac ccttctctcc ctcgcagttc ttaaacactt ccagtaacca    1740
tgaaaactca gacttggaaa tgccttcttt aacttccacc cccctcattg gtcacaaatt    1800
gactgttaca acaccatttc atagagacca gactgtgaaa actcaaaagg aaaatactgt    1860
ttttagaacc ccagctatca aaaggtcaat cttagaaagc tctccaagaa ctcctacacc    1920
attcaaacat gcacttgcag ctcaagaaat taaatacggt cccctgaaga tgctacctca    1980
gacaccctct catctagtag aagatctgca ggatgtgatc aaacaggaat ctgatgaatc    2040
tggaattgtt gctgagtttc aagaaaatgg accacccta ctgaagaaaa tcaaacaaga     2100
ggtggaatct ccaactgata aatcaggaaa cttcttctgc tcacaccact gggaagggga    2160
cagtctgaat acccaactgt tcacgcagac ctcgcctgtg gcagatgcac cgaatattct    2220
tacaagctcc gttttaatgg caccagcatc agaaagtgaa gacaatgttc tcaaagcatt    2280
tacagtacct aaaaacaggt ccctggcgag cccccttgcag ccttgtagca gtacctggga   2340
```

| | | | |
|---|---|---|---|
| acctgcatcc | tgtggaaaga | tggaggagca gatgacatct tccagtcaag ctcgtaaata | 2400 |
| cgtgaatgca | ttctcagccc | ggacgctggt catgtgagac atttccagaa aagcattatg | 2460 |
| gttttcagaa | cacttcaagt | tgacttggga tatatcattc ctcaacatga aactttttcat | 2520 |
| gaatgggaga | agaacctatt | tttgttgtgg tacaacagtt gagagcagca ccaagtgcat | 2580 |
| ttagttgaat | gaagtcttct | tggatttcac ccaactaaaa ggattttttaa aaataaataa | 2640 |
| cagtcttacc | taaattatta | ggtaatgaat tgtagccagt tgttaatatc ttaatgcaga | 2700 |
| ttttttttaaa | aaaaacataa | aatgattttat ctgtattttta aaggatccaa cagatcagta | 2760 |
| tttttttcctg | tgatgggttt | tttgaaattt gacacattaa aaggtactcc agtatttcac | 2820 |
| ttttctcgat | cactaaacat | atgcatatat ttttaaaaat cagtaaaagc attactctaa | 2880 |
| gtgtagactt | ataccatgt | gacatttaat ccagattgta aatgctcatt tatggttaat | 2940 |
| gacattgaag | gtacatttat | tgtaccaaac catttttatga gttttctgtt agcttgcttt | 3000 |
| aaaaattatt | actgtaagaa | atagtttttat aaaaaattat atttttattc agtaatttaa | 3060 |
| ttttgtaaat | gccaaatgaa | aaacgttttt tgctgctatg gtcttagcct gtagacatgc | 3120 |
| tgctagtatc | agaggggcag | tagagcttgg acagaaagaa aagaaacttg gtgttaggta | 3180 |
| attgactatg | cactagtatt | tcagacttttt taatttttata tatatataca ttttttttttcc | 3240 |
| ttctgcaata | catttgaaaa | cttgtttggg agactctgca ttttttattg tggtttttttt | 3300 |
| gttattgttg | gtttatacaa | gcatgcgttg cacttctttt ttgggagatg tgtgttgttg | 3360 |
| atgttctatg | ttttgttttg | agtgtagcct gactgtttta taatttggga gttctgcatt | 3420 |
| tgatccgcat | cccctgtggt | ttctaagtgt atggtctcag aactgttgca tggatcctgt | 3480 |
| gtttgcaact | ggggagacag | aaactgtggt tgatagccag tcactgcctt aagaacattt | 3540 |
| gatgcaagat | ggccagcact | gaactttttga gatatgacgg tgtacttact gccttgtagc | 3600 |
| aaaataaaga | tgtgccctta | ttttacctac | 3630 |

<210> SEQ ID NO 11
<211> LENGTH: 3204
<212> TYPE: DNA
<213> ORGANISM: Homo sapiens

<400> SEQUENCE: 11

| | | | |
|---|---|---|---|
| aatatcaacc | tgtttcctcc | tcctccttct cctcctcctc cgtgacctcc tcctcctctt | 60 |
| tctcctgaga | aacttcgccc | cagcggtgcg gagcgccgct gcgcagccgg ggagggacgc | 120 |
| aggcaggcg | cgggcagcgg | gaggcggcag cccggtgcgg tccccgcggc tctcggcgga | 180 |
| gccccgcgcc | cgccgcgcca | tggcccgaag accccggcac agcatatata gcagtgacga | 240 |
| ggatgatgag | gactttgaga | tgtgtgacca tgactatgat gggctgcttc ccaagtctgg | 300 |
| aaagcgtcac | ttggggaaaa | caaggtggac ccgggaagag gatgaaaaac tgaagaagct | 360 |
| ggtggaacaa | aatggaacag | atgactgaa agttattgcc aattatctcc cgaatcgaac | 420 |
| agatgtgcag | tgccagcacc | gatggcagaa agtactaaac cctgagctca tcaagggtcc | 480 |
| ttggaccaaa | gaagaagatc | agagagtgat agagcttgta cagaaatacg gtccgaaacg | 540 |
| ttggtctgtt | attgccaagc | acttaaaggg gagaattgga aaacaatgta gggagaggtg | 600 |
| gcataaccac | ttgaatccag | aagttaagaa aacctcctgg acagaagagg aagacagaat | 660 |
| tatttaccag | gcacacaaga | gactggggaa cagatgggca gaaatcgcaa agctactgcc | 720 |
| tggacgaact | gataatgcta | tcaagaacca ctggaattct acaatgcgtc ggaaggtcga | 780 |

```
acaggaaggt tatctgcagg agtcttcaaa agccagccag ccagcagtgg ccacaagctt    840
ccagaagaac agtcatttga tgggttttgc tcaggctccg cctacagctc aactccctgc    900
cactggccag cccactgtta caacgacta ttcctattac cacatttctg aagcacaaaa     960
tgtctccagt catgttccat accctgtagc gttacatgta aatatagtca atgtccctca   1020
gccagctgcc gcagccattc agagacacta taatgatgaa gaccctgaga aggaaaagcg   1080
aataaaggaa ttagaattgc tcctaatgtc aaccgagaat gagctaaaag acagcaggt   1140 gctaccaaca cagaaccaca catgcagcta ccccgggtgg cacagcacca ccattgccga   1200
ccacaccaga cctcatggag acagtgcacc tgtttcctgt ttgggagaac accactccac   1260
tccatctctg ccagcggatc ctggctccct acctgaagaa agcgcctcgc cagcaaggtg   1320
catgatcgtc caccagggca ccattctgga taatgttaag aacctcttag aatttgcaga   1380
aacactccaa tttatagatt ctttcttaaa cacttccagt aaccatgaaa actcagactt   1440
ggaaatgcct tctttaactt ccaccccct cattggtcac aaattgactg ttacaacacc     1500
atttcataga gaccagactg tgaaaactca aaaggaaaat actgttttta gaaccccagc   1560
tatcaaaagg tcaatcttag aaagctctcc aagaactcct acaccattca acatgcact    1620 tgcagctcaa gaaattaaat acggtccct gaagatgcta cctcagacac cctctcatct    1680
agtagaagat ctgcaggatg tgatcaaaca ggaatctgat gaatctggaa ttgttgctga   1740 gttcaagaa aatggaccac ccttactgaa gaaaatcaaa caagagaata ttcttacaag   1800
ctccgtttta atggcaccag catcagaaga tgaagacaat gttctcaaag catttacagt   1860
acctaaaaac aggtccctgg cgagcccctt gcagccttgt agcagtacct gggaacctgc   1920
atcctgtgga agatggagg agcagatgac atcttccagt caagctcgta aatacgtgaa    1980
tgcattctca gcccggacgc tggtcatgtg agacattcc agaaaagcat tatggttttc    2040
agaacacttc aagttgactt gggatatatc attcctcaac atgaaacttt tcatgaatgg   2100
gagaagaacc tattttgtt gtggtacaac agttgagagc agcaccaagt gcatttagtt    2160
gaatgaagtc ttcttggatt tcacccaact aaaaggattt ttaaaaataa ataacagtct   2220
tacctaaatt attaggtaat gaattgtagc cagttgttaa tatcttaatg cagattttt    2280 taaaaaaaac ataaaatgat ttatctgtat tttaaaggat ccaacagatc agtattttt    2340 cctgtgatgg gttttttgaa atttgacaca ttaaaggta ctccagtatt tcacttttct    2400
cgatcactaa acatatgcat atatttttaa aaatcagtaa aagcattact ctaagtgtag   2460
acttaatacc atgtgacatt taatccagat tgtaaatgct catttatggt taatgacatt   2520
gaaggtacat ttattgtacc aaaccatttt atgagttttc tgttagcttg ctttaaaaat   2580
tattactgta agaaatagtt ttataaaaaa ttatatttt attcagtaat ttaattttgt    2640
aaatgccaaa tgaaaacgt ttttttgctgc tatggtctta gcctgtagac atgctgctag    2700
tatcagaggg gcagtagagc ttggacagaa agaaaagaaa cttggtgtta ggtaattgac   2760
tatgcactag tatttcagac tttttaattt tatatatata tacattttt ttccttctgc    2820 aatacatttg aaaacttgtt tgggagactc tgcatttttt attgtggttt tttgttatt    2880 gttggtttat acaagcatgc gttgcacttc ttttttggga gatgtgtgtt gttgatgttc   2940
tatgttttgt tttgagtgta gcctgactgt tttataattt gggagttctg catttgatcc   3000
gcatcccctg tggtttctaa gtgtatggtc tcagaactgt tgcatggatc ctgtgttgc    3060 aactggggag acagaaactg tggttgatag ccagtcactg ccttaagaac atttgatgca   3120
agatggccag cactgaactt ttgagatatg acggtgtact tactgccttg tagcaaaata   3180
```
aagatgtgcc cttattttac ctac                                          3204

<210> SEQ ID NO 12
<211> LENGTH: 3210
<212> TYPE: DNA
<213> ORGANISM: Homo sapiens

<400> SEQUENCE: 12
aatatcaacc tgtttcctcc tcctccttct cctcctcctc cgtgacctcc tcctcctctt      60
tctcctgaga aacttcgccc cagcggtgcg gagcgccgct gcgcagccgg ggagggacgc     120
aggcaggcgg cgggcagcgg gaggcggcag cccggtgcgg tccccgcggc tctcggcgga     180
gccccgcgcc cgccgcgcca tggcccgaag accccggcac agcatatata gcagtgacga     240
ggatgatgag gactttgaga tgtgtgacca tgactatgat gggctgcttc ccaagtctgg     300
aaagcgtcac ttggggaaaa caaggtggac ccgggaagag gatgaaaaac tgaagaagct     360
ggtggaacag aatggaacag atgactggaa agttattgcc aattatctcc gaatcgaac      420 agatgtgcag tgccagcacc gatggcagaa agtactaaac cctgagctca tcaagggtcc     480
ttggaccaaa gaagaagatc agagagtgat agagcttgta cagaaatacg gtccgaaacg     540
ttggtctgtt attgccaagc acttaaaggg gagaattgga aaacaatgta gggagaggtg     600
gcataaccac ttgaatccag aagttaagaa aacctcctgg acagaagagg aagacagaat     660
tatttaccag gcacacaaga gactggggaa cagatgggca gaaatcgcaa agctactgcc     720
tggacgaact gataatgcta tcaagaacca ctggaattct acaatgcgtc ggaaggtcga     780
acaggaaggt tatctgcagg agtcttcaaa agccagccag ccagcagtgg ccacaagctt     840
ccagaagaac agtcatttga tgggttttgc tcaggctccg cctacagctc aactccctgc     900
cactggccag cccactgtta caacgactat tcctattac cacatttctg aagcacaaaa      960
tgtctccagt catgttccat accctgtagc gttacatgta aatatagtca atgtccctca    1020
gccagctgcc gcagccattc agacacagaa ccacacatgc agctaccccg gtggcacag     1080 caccaccatt gccgaccaca ccagacctca tggagacagt gcacctgttt cctgtttggg    1140
agaacaccac tccactccat ctctgccagc ggatcctggc tccctacctg aagaaagcgc    1200
ctcgccagca aggtgcatga tcgtccacca gggcaccatt ctggataatg ttaagaacct    1260
cttagaattt gcagaaacac tccaatttat agattctttc ttaaacactt ccagtaacca    1320
tgaaaactca gacttggaaa tgccttcttt aacttccacc ccctcattg gtcacaaatt     1380 gactgttaca acaccatttc atagagacca gactgtgaaa actcaaaagg aaaatactgt    1440
ttttagaacc ccagctatca aaggtcaat cttagaaagc tctccaagaa ctcctacacc     1500
attcaaacat gcacttgcag ctcaagaaat taaatacggt cccctgaaga tgctacctca    1560
gacaccctct catctagtag aagatctgca ggatgtgatc aaacaggaat ctgatgaatc    1620
tggaattgtt gctgagtttc aagaaaatgg accaccctta ctgaagaaaa tcaaacaaga    1680
ggtggaatct ccaactgata atcaggaaa cttcttctgc tcacaccact gggaagggga    1740
cagtctgaat acccaactgt tcacgcagac ctcgcctgtg gcagatgcac cgaatattct    1800
tacaagctcc gttttaatgg caccagcatc agaagatgaa gacaatgttc tcaaagcatt    1860
tacagtacct aaaaacaggt ccctggcgag ccccttgcag ccttgtagca gtacctggga    1920
acctgcatcc tgtggaaaga tggaggagca gatgacatct tccagtcaag ctcgtaaata    1980
cgtgaatgca ttctcagccc ggacgctggt catgtgagac atttccagaa aagcattatg    2040

-continued

```
gttttcagaa cacttcaagt tgacttggga tatatcattc ctcaacatga aacttttcat    2100
gaatgggaga agaacctatt tttgttgtgg tacaacagtt gagagcagca ccaagtgcat    2160
ttagttgaat gaagtcttct tggatttcac ccaactaaaa ggattttaa  aaataaataa    2220 cagtcttacc taaattatta ggtaatgaat tgtagccagt tgttaatatc ttaatgcaga    2280
tttttttaaa aaaacataa  aatgatttat ctgtatttta aaggatccaa cagatcagta    2340 tttttcctg  tgatgggttt tttgaaattt gacacattaa aaggtactcc agtatttcac    2400
ttttctcgat cactaaacat atgcatatat ttttaaaaat cagtaaaagc attactctaa    2460
gtgtagactt aataccatgt gacatttaat ccagattgta aatgctcatt tatggttaat    2520
gacattgaag gtacatttat tgtaccaaac cattttatga gttttctgtt agcttgcttt    2580
aaaaattatt actgtaagaa atagtttat  aaaaaattat attttattc  agtaatttaa    2640 ttttgtaaat gccaaatgaa aaacgttttt tgctgctatg gtcttagcct gtagacatgc    2700
tgctagtatc agaggggcag tagagcttgg acagaaagaa aagaaacttg gtgttaggta    2760
attgactatg cactagtatt tcagactttt taattttata tatatataca ttttttttcc    2820
ttctgcaata catttgaaaa cttgtttggg agactctgca ttttttattg tggtttttt     2880 gttattgttg gtttatacaa gcatgcgttg cacttctttt ttgggagatg tgtgttgttg    2940
atgttctatg ttttgttttg agtgtagcct gactgtttta taatttggga gttctgcatt    3000
tgatccgcat cccctgtggt ttctaagtgt atggtctcag aactgttgca tggatcctgt    3060
gtttgcaact ggggagacag aaactgtggt tgatagccag tcactgcctt aagaacattt    3120
gatgcaagat ggccagcact gaactttga  gatatgacgg tgtacttact gccttgtagc    3180
aaaataaaga tgtgccctta ttttacctac                                    3210

<210> SEQ ID NO 13
<211> LENGTH: 761
<212> TYPE: PRT
<213> ORGANISM: Homo sapiens

<400> SEQUENCE: 13

Met Ala Arg Arg Pro Arg His Ser Ile Tyr Ser Ser Asp Glu Asp Asp
1               5                   10                  15

Glu Asp Phe Glu Met Cys Asp His Asp Tyr Asp Gly Leu Leu Pro Lys
            20                  25                  30

Ser Gly Lys Arg His Leu Gly Lys Thr Arg Trp Thr Arg Glu Glu Asp
        35                  40                  45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
        115                 120                 125

Gln Cys Arg Glu Arg Trp His Asn His Leu Asn Pro Glu Val Lys Lys
    130                 135                 140

Thr Ser Trp Thr Glu Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
```

```
                165                 170                 175
Thr Asp Asn Ala Ile Lys Asn His Trp Asn Ser Thr Met Arg Arg Lys
            180                 185                 190

Val Gln Gln Glu Gly Tyr Leu Gln Glu Ser Ser Lys Ala Ser Gln Pro
        195                 200                 205

Ala Val Ala Thr Ser Phe Gln Lys Asn Ser His Leu Met Gly Phe Ala
210                 215                 220

Gln Ala Pro Pro Thr Ala Gln Leu Pro Ala Thr Gly Gln Pro Thr Val
225                 230                 235                 240

Asn Asn Asp Tyr Ser Tyr Tyr His Ile Ser Glu Ala Gln Asn Val Ser
                245                 250                 255

Ser His Val Pro Tyr Pro Val Ala Leu His Val Asn Ile Val Asn Val
            260                 265                 270

Pro Gln Pro Ala Ala Ala Ile Gln Arg His Tyr Asn Asp Glu Asp
        275                 280                 285

Pro Glu Lys Glu Lys Arg Ile Lys Glu Leu Glu Leu Leu Met Ser
    290                 295                 300

Thr Glu Asn Glu Leu Lys Gly Gln Gln Val Leu Pro Thr Gln Asn His
305                 310                 315                 320

Thr Cys Ser Tyr Pro Gly Trp His Ser Thr Thr Ile Ala Asp His Thr
                325                 330                 335

Arg Pro His Gly Asp Ser Ala Pro Val Ser Cys Leu Gly Glu His His
            340                 345                 350

Ser Thr Pro Ser Leu Pro Ala Asp Pro Gly Ser Leu Pro Glu Glu Ser
        355                 360                 365

Ala Ser Pro Ala Arg Cys Met Ile Val His Gln Gly Thr Ile Leu Asp
370                 375                 380

Asn Val Lys Asn Leu Leu Glu Phe Ala Glu Thr Leu Gln Phe Ile Asp
385                 390                 395                 400

Ser Asp Ser Ser Ser Trp Cys Asp Leu Ser Ser Phe Glu Phe Glu
                405                 410                 415

Glu Ala Asp Phe Ser Pro Ser Gln His His Thr Gly Lys Ala Leu Gln
            420                 425                 430

Leu Gln Gln Arg Glu Gly Asn Gly Thr Lys Pro Ala Gly Glu Pro Ser
        435                 440                 445

Pro Arg Val Asn Lys Arg Met Leu Ser Glu Ser Ser Leu Asp Pro Pro
    450                 455                 460

Lys Val Leu Pro Pro Ala Arg His Ser Thr Ile Pro Leu Val Ile Leu
465                 470                 475                 480

Arg Lys Lys Arg Gly Gln Ala Ser Pro Leu Ala Thr Gly Asp Cys Ser
                485                 490                 495

Ser Phe Ile Phe Ala Asp Val Ser Ser Thr Pro Lys Arg Ser Pro
            500                 505                 510

Val Lys Ser Leu Pro Phe Ser Pro Ser Gln Phe Leu Asn Thr Ser Ser
        515                 520                 525

Asn His Glu Asn Ser Asp Leu Glu Met Pro Ser Leu Thr Ser Thr Pro
    530                 535                 540

Leu Ile Gly His Lys Leu Thr Val Thr Thr Pro Phe His Arg Asp Gln
545                 550                 555                 560

Thr Val Lys Thr Gln Lys Glu Asn Thr Val Phe Arg Thr Pro Ala Ile
                565                 570                 575

Lys Arg Ser Ile Leu Glu Ser Ser Pro Arg Thr Pro Thr Pro Phe Lys
            580                 585                 590
```

His Ala Leu Ala Ala Gln Glu Ile Lys Tyr Gly Pro Leu Lys Met Leu
            595                 600                 605

Pro Gln Thr Pro Ser His Leu Val Glu Asp Leu Gln Asp Val Ile Lys
        610                 615                 620

Gln Glu Ser Asp Glu Ser Gly Ile Val Ala Glu Phe Gln Glu Asn Gly
625                 630                 635                 640

Pro Pro Leu Leu Lys Lys Ile Lys Gln Glu Val Glu Ser Pro Thr Asp
                645                 650                 655

Lys Ser Gly Asn Phe Phe Cys Ser His His Trp Gly Asp Ser Leu
            660                 665                 670

Asn Thr Gln Leu Phe Thr Gln Thr Ser Pro Val Ala Asp Ala Pro Asn
            675                 680                 685

Ile Leu Thr Ser Ser Val Leu Met Ala Pro Ala Ser Glu Asp Glu Asp
            690                 695                 700

Asn Val Leu Lys Ala Phe Thr Val Pro Lys Asn Arg Ser Leu Ala Ser
705                 710                 715                 720

Pro Leu Gln Pro Cys Ser Ser Thr Trp Glu Pro Ala Ser Cys Gly Lys
                725                 730                 735

Met Glu Glu Gln Met Thr Ser Ser Gln Ala Arg Lys Tyr Val Asn
            740                 745                 750

Ala Phe Ser Ala Arg Thr Leu Val Met
            755                 760

<210> SEQ ID NO 14
<211> LENGTH: 640
<212> TYPE: PRT
<213> ORGANISM: Homo sapiens

<400> SEQUENCE: 14

Met Ala Arg Arg Pro Arg His Ser Ile Tyr Ser Ser Asp Glu Asp
1               5                   10                  15

Glu Asp Phe Glu Met Cys Asp His Asp Tyr Asp Gly Leu Leu Pro Lys
            20                  25                  30

Ser Gly Lys Arg His Leu Gly Lys Thr Arg Trp Thr Arg Glu Glu Asp
        35                  40                  45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
        115                 120                 125

Gln Cys Arg Glu Arg Trp His Asn His Leu Asn Pro Glu Val Lys Lys
    130                 135                 140

Thr Ser Trp Thr Glu Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Glu Ser Ser Lys Ala Ser Gln Pro

-continued

```
               195                 200                 205
Ala Val Ala Thr Ser Phe Gln Lys Asn Ser His Leu Met Gly Phe Ala
210                 215                 220

Gln Ala Pro Pro Thr Ala Gln Leu Pro Ala Thr Gly Gln Pro Thr Val
225                 230                 235                 240

Asn Asn Asp Tyr Ser Tyr Tyr His Ile Ser Glu Ala Gln Asn Val Ser
                    245                 250                 255

Ser His Val Pro Tyr Pro Val Ala Leu His Val Asn Ile Val Asn Val
                260                 265                 270

Pro Gln Pro Ala Ala Ala Ile Gln Arg His Tyr Asn Asp Glu Asp
            275                 280                 285

Pro Glu Lys Glu Lys Arg Ile Lys Glu Leu Glu Leu Leu Met Ser
290                 295                 300

Thr Glu Asn Glu Leu Lys Gly Gln Gln Val Leu Pro Thr Gln Asn His
305                 310                 315                 320

Thr Cys Ser Tyr Pro Gly Trp His Ser Thr Thr Ile Ala Asp His Thr
                    325                 330                 335

Arg Pro His Gly Asp Ser Ala Pro Val Ser Cys Leu Gly Glu His His
                340                 345                 350

Ser Thr Pro Ser Leu Pro Ala Asp Pro Gly Ser Leu Pro Glu Glu Ser
            355                 360                 365

Ala Ser Pro Ala Arg Cys Met Ile Val His Gln Gly Thr Ile Leu Asp
370                 375                 380

Asn Val Lys Asn Leu Leu Glu Phe Ala Glu Thr Leu Gln Phe Ile Asp
385                 390                 395                 400

Ser Phe Leu Asn Thr Ser Ser Asn His Glu Asn Ser Asp Leu Glu Met
                    405                 410                 415

Pro Ser Leu Thr Ser Thr Pro Leu Ile Gly His Lys Leu Thr Val Thr
                420                 425                 430

Thr Pro Phe His Arg Asp Gln Thr Val Lys Thr Gln Lys Glu Asn Thr
            435                 440                 445

Val Phe Arg Thr Pro Ala Ile Lys Arg Ser Ile Leu Glu Ser Ser Pro
450                 455                 460

Arg Thr Pro Thr Pro Phe Lys His Ala Leu Ala Ala Gln Glu Ile Lys
465                 470                 475                 480

Tyr Gly Pro Leu Lys Met Leu Pro Gln Thr Pro Ser His Leu Val Glu
                    485                 490                 495

Asp Leu Gln Asp Val Ile Lys Gln Glu Ser Asp Glu Ser Gly Ile Val
                500                 505                 510

Ala Glu Phe Gln Glu Asn Gly Pro Pro Leu Leu Lys Lys Ile Lys Gln
            515                 520                 525

Glu Val Glu Ser Pro Thr Asp Lys Ser Gly Asn Phe Phe Cys Ser His
530                 535                 540

His Trp Glu Gly Asp Ser Leu Asn Thr Gln Leu Phe Thr Gln Thr Ser
545                 550                 555                 560

Pro Val Ala Asp Ala Pro Asn Ile Leu Thr Ser Ser Val Leu Met Ala
                    565                 570                 575

Pro Ala Ser Glu Asp Glu Asp Asn Val Leu Lys Ala Phe Thr Val Pro
                580                 585                 590

Lys Asn Arg Ser Leu Ala Ser Pro Leu Gln Pro Cys Ser Ser Thr Trp
            595                 600                 605

Glu Pro Ala Ser Cys Gly Lys Met Glu Glu Gln Met Thr Ser Ser Ser
610                 615                 620
```

Gln Ala Arg Lys Tyr Val Asn Ala Phe Ser Arg Thr Leu Val Met
625                 630                 635                 640

<210> SEQ ID NO 15
<211> LENGTH: 637
<212> TYPE: PRT
<213> ORGANISM: Homo sapiens

<400> SEQUENCE: 15

Met Ala Arg Arg Pro Arg His Ser Ile Tyr Ser Ser Asp Glu Asp Asp
1               5                   10                  15

Glu Asp Phe Glu Met Cys Asp His Asp Tyr Asp Gly Leu Leu Pro Lys
            20                  25                  30

Ser Gly Lys Arg His Leu Gly Lys Thr Arg Trp Thr Arg Glu Glu Asp
        35                  40                  45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
        115                 120                 125

Gln Cys Arg Glu Arg Trp His Asn His Leu Asn Pro Glu Val Lys Lys
130                 135                 140

Thr Ser Trp Thr Glu Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Glu Ser Ser Lys Ala Ser Gln Pro
        195                 200                 205

Ala Val Ala Thr Ser Phe Gln Lys Asn Ser His Leu Met Gly Phe Ala
210                 215                 220

Gln Ala Pro Pro Thr Ala Gln Leu Pro Ala Thr Gly Gln Pro Thr Val
225                 230                 235                 240

Asn Asn Asp Tyr Ser Tyr Tyr His Ile Ser Glu Ala Gln Asn Val Ser
                245                 250                 255

Ser His Val Pro Tyr Pro Val Ala Leu His Val Asn Ile Val Asn Val
            260                 265                 270

Pro Gln Pro Ala Ala Ala Ile Gln Arg His Tyr Asn Asp Glu Asp
        275                 280                 285

Pro Glu Lys Glu Lys Arg Ile Lys Glu Leu Glu Leu Leu Leu Met Ser
290                 295                 300

Thr Glu Asn Glu Leu Lys Gly Gln Gln Thr Gln Asn His Thr Cys Ser
305                 310                 315                 320

Tyr Pro Gly Trp His Ser Thr Thr Ile Ala Asp His Thr Arg Pro His
                325                 330                 335

Gly Asp Ser Ala Pro Val Ser Cys Leu Gly Glu His His Ser Thr Pro
            340                 345                 350

Ser Leu Pro Ala Asp Pro Gly Ser Leu Pro Glu Glu Ser Ala Ser Pro

```
            355                 360                 365
Ala Arg Cys Met Ile Val His Gln Gly Thr Ile Leu Asp Asn Val Lys
370                 375                 380

Asn Leu Leu Glu Phe Ala Glu Thr Leu Gln Phe Ile Asp Ser Phe Leu
385                 390                 395                 400

Asn Thr Ser Ser Asn His Glu Asn Ser Asp Leu Glu Met Pro Ser Leu
                405                 410                 415

Thr Ser Thr Pro Leu Ile Gly His Lys Leu Thr Val Thr Thr Pro Phe
            420                 425                 430

His Arg Asp Gln Thr Val Lys Thr Gln Lys Glu Asn Thr Val Phe Arg
                435                 440                 445

Thr Pro Ala Ile Lys Arg Ser Ile Leu Glu Ser Ser Pro Arg Thr Pro
            450                 455                 460

Thr Pro Phe Lys His Ala Leu Ala Ala Gln Glu Ile Lys Tyr Gly Pro
465                 470                 475                 480

Leu Lys Met Leu Pro Gln Thr Pro Ser His Leu Val Glu Asp Leu Gln
                485                 490                 495

Asp Val Ile Lys Gln Glu Ser Asp Glu Ser Gly Ile Val Ala Glu Phe
            500                 505                 510

Gln Glu Asn Gly Pro Pro Leu Leu Lys Lys Ile Lys Gln Glu Val Glu
                515                 520                 525

Ser Pro Thr Asp Lys Ser Gly Asn Phe Phe Cys Ser His His Trp Glu
530                 535                 540

Gly Asp Ser Leu Asn Thr Gln Leu Phe Thr Gln Thr Ser Pro Val Ala
545                 550                 555                 560

Asp Ala Pro Asn Ile Leu Thr Ser Ser Val Leu Met Ala Pro Ala Ser
                565                 570                 575

Glu Asp Glu Asp Asn Val Leu Lys Ala Phe Thr Val Pro Lys Asn Arg
            580                 585                 590

Ser Leu Ala Ser Pro Leu Gln Pro Cys Ser Ser Thr Trp Glu Pro Ala
            595                 600                 605

Ser Cys Gly Lys Met Glu Glu Gln Met Thr Ser Ser Ser Gln Ala Arg
610                 615                 620

Lys Tyr Val Asn Ala Phe Ser Ala Arg Thr Leu Val Met
625                 630                 635

<210> SEQ ID NO 16
<211> LENGTH: 758
<212> TYPE: PRT
<213> ORGANISM: Homo sapiens

<400> SEQUENCE: 16

Met Ala Arg Arg Pro Arg His Ser Ile Tyr Ser Ser Asp Glu Asp Asp
1               5                   10                  15

Glu Asp Phe Glu Met Cys Asp His Asp Tyr Asp Gly Leu Leu Pro Lys
            20                  25                  30

Ser Gly Lys Arg His Leu Gly Lys Thr Arg Trp Thr Arg Glu Glu Asp
        35                  40                  45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95
```

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
        115                 120                 125

Gln Cys Arg Glu Arg Trp His Asn His Leu Asn Pro Glu Val Lys Lys
    130                 135                 140

Thr Ser Trp Thr Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Glu Ser Ser Lys Ala Ser Gln Pro
        195                 200                 205

Ala Val Ala Thr Ser Phe Gln Lys Asn Ser His Leu Met Gly Phe Ala
    210                 215                 220

Gln Ala Pro Pro Thr Ala Gln Leu Pro Ala Thr Gly Gln Pro Thr Val
225                 230                 235                 240

Asn Asn Asp Tyr Ser Tyr Tyr His Ile Ser Glu Ala Gln Asn Val Ser
                245                 250                 255

Ser His Val Pro Tyr Pro Val Ala Leu His Val Asn Ile Val Asn Val
            260                 265                 270

Pro Gln Pro Ala Ala Ala Ala Ile Gln Arg His Tyr Asn Asp Glu Asp
        275                 280                 285

Pro Glu Lys Glu Lys Arg Ile Lys Glu Leu Glu Leu Leu Leu Met Ser
    290                 295                 300

Thr Glu Asn Glu Leu Lys Gly Gln Gln Thr Gln Asn His Thr Cys Ser
305                 310                 315                 320

Tyr Pro Gly Trp His Ser Thr Thr Ile Ala Asp His Thr Arg Pro His
                325                 330                 335

Gly Asp Ser Ala Pro Val Ser Cys Leu Gly Glu His His Ser Thr Pro
            340                 345                 350

Ser Leu Pro Ala Asp Pro Gly Ser Leu Pro Glu Glu Ser Ala Ser Pro
        355                 360                 365

Ala Arg Cys Met Ile Val His Gln Gly Thr Ile Leu Asp Asn Val Lys
    370                 375                 380

Asn Leu Leu Glu Phe Ala Glu Thr Leu Gln Phe Ile Asp Ser Asp Ser
385                 390                 395                 400

Ser Ser Trp Cys Asp Leu Ser Ser Phe Glu Phe Phe Glu Glu Ala Asp
                405                 410                 415

Phe Ser Pro Ser Gln His His Thr Gly Lys Ala Leu Gln Leu Gln Gln
            420                 425                 430

Arg Glu Gly Asn Gly Thr Lys Pro Ala Gly Glu Pro Ser Pro Arg Val
        435                 440                 445

Asn Lys Arg Met Leu Ser Glu Ser Ser Leu Asp Pro Pro Lys Val Leu
    450                 455                 460

Pro Pro Ala Arg His Ser Thr Ile Pro Leu Val Ile Leu Arg Lys Lys
465                 470                 475                 480

Arg Gly Gln Ala Ser Pro Leu Ala Thr Gly Asp Cys Ser Ser Phe Ile
                485                 490                 495

Phe Ala Asp Val Ser Ser Thr Pro Lys Arg Ser Pro Val Lys Ser
            500                 505                 510

Leu Pro Phe Ser Pro Ser Gln Phe Leu Asn Thr Ser Ser Asn His Glu

```
            515                 520                 525
Asn Ser Asp Leu Glu Met Pro Ser Leu Thr Ser Thr Pro Leu Ile Gly
    530                 535                 540
His Lys Leu Thr Val Thr Thr Pro Phe His Arg Asp Gln Thr Val Lys
545                 550                 555                 560
Thr Gln Lys Glu Asn Thr Val Phe Arg Thr Pro Ala Ile Lys Arg Ser
                565                 570                 575
Ile Leu Glu Ser Ser Pro Arg Thr Pro Thr Pro Phe Lys His Ala Leu
            580                 585                 590
Ala Ala Gln Glu Ile Lys Tyr Gly Pro Leu Lys Met Leu Pro Gln Thr
                595                 600                 605
Pro Ser His Leu Val Glu Asp Leu Gln Asp Val Ile Lys Gln Glu Ser
        610                 615                 620
Asp Glu Ser Gly Ile Val Ala Glu Phe Gln Asn Gly Pro Pro Leu
625                 630                 635                 640
Leu Lys Lys Ile Lys Gln Glu Val Glu Ser Pro Thr Asp Lys Ser Gly
                645                 650                 655
Asn Phe Phe Cys Ser His His Trp Glu Gly Asp Ser Leu Asn Thr Gln
            660                 665                 670
Leu Phe Thr Gln Thr Ser Pro Val Ala Asp Ala Pro Asn Ile Leu Thr
        675                 680                 685
Ser Ser Val Leu Met Ala Pro Ala Ser Glu Asp Glu Asp Asn Val Leu
    690                 695                 700
Lys Ala Phe Thr Val Pro Lys Asn Arg Ser Leu Ala Ser Pro Leu Gln
705                 710                 715                 720
Pro Cys Ser Ser Thr Trp Glu Pro Ala Ser Cys Gly Lys Met Glu Glu
                725                 730                 735
Gln Met Thr Ser Ser Gln Ala Arg Lys Tyr Val Asn Ala Phe Ser
            740                 745                 750
Ala Arg Thr Leu Val Met
        755

<210> SEQ ID NO 17
<211> LENGTH: 555
<212> TYPE: PRT
<213> ORGANISM: Homo sapiens

<400> SEQUENCE: 17

Met Ala Arg Arg Pro Arg His Ser Ile Tyr Ser Ser Asp Glu Asp Asp
1               5                   10                  15
Glu Asp Phe Glu Met Cys Asp His Asp Tyr Asp Gly Leu Leu Pro Lys
            20                  25                  30
Ser Gly Lys Arg His Leu Gly Lys Thr Arg Trp Thr Arg Glu Glu Asp
        35                  40                  45
Glu Lys Leu Lys Lys Leu Val Glu Gln Asn Gly Thr Asp Asp Trp Lys
    50                  55                  60
Val Ile Ala Asn Tyr Leu Pro Asn Arg Thr Asp Val Gln Cys Gln His
65                  70                  75                  80
Arg Trp Gln Lys Val Leu Asn Pro Glu Leu Ile Lys Gly Pro Trp Thr
                85                  90                  95
Lys Glu Glu Asp Gln Arg Val Ile Glu Leu Val Gln Lys Tyr Gly Pro
            100                 105                 110
Lys Arg Trp Ser Val Ile Ala Lys His Leu Lys Gly Arg Ile Gly Lys
        115                 120                 125
```

```
Gln Cys Arg Glu Arg Trp His Asn His Leu Asn Pro Glu Val Lys Lys
        130                 135                 140

Thr Ser Trp Thr Glu Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Glu Ser Ser Lys Ala Ser Gln Pro
        195                 200                 205

Ala Val Ala Thr Ser Phe Gln Lys Asn Ser His Leu Met Gly Phe Ala
210                 215                 220

Gln Ala Pro Pro Thr Ala Gln Leu Pro Ala Thr Gly Gln Pro Thr Val
225                 230                 235                 240

Asn Asn Asp Tyr Ser Tyr Tyr His Ile Ser Glu Ala Gln Asn Val Ser
                245                 250                 255

Ser His Val Pro Tyr Pro Val Ala Leu His Val Asn Ile Val Asn Val
        260                 265                 270

Pro Gln Pro Ala Ala Ala Ile Gln Arg His Tyr Asn Asp Glu Asp
        275                 280                 285

Pro Glu Lys Glu Lys Arg Ile Lys Glu Leu Glu Leu Leu Met Ser
        290                 295                 300

Thr Glu Asn Glu Leu Lys Gly Gln Gln Val Leu Pro Phe Leu Asn Thr
305                 310                 315                 320

Ser Ser Asn His Glu Asn Ser Asp Leu Glu Met Pro Ser Leu Thr Ser
                325                 330                 335

Thr Pro Leu Ile Gly His Lys Leu Thr Val Thr Thr Pro Phe His Arg
            340                 345                 350

Asp Gln Thr Val Lys Thr Gln Lys Glu Asn Thr Val Phe Arg Thr Pro
        355                 360                 365

Ala Ile Lys Arg Ser Ile Leu Glu Ser Ser Pro Arg Thr Pro Thr Pro
370                 375                 380

Phe Lys His Ala Leu Ala Ala Gln Glu Ile Lys Tyr Gly Pro Leu Lys
385                 390                 395                 400

Met Leu Pro Gln Thr Pro Ser His Leu Val Glu Asp Leu Gln Asp Val
                405                 410                 415

Ile Lys Gln Glu Ser Asp Glu Ser Gly Ile Val Ala Glu Phe Gln Glu
            420                 425                 430

Asn Gly Pro Pro Leu Leu Lys Lys Ile Lys Gln Glu Val Glu Ser Pro
        435                 440                 445

Thr Asp Lys Ser Gly Asn Phe Phe Cys Ser His His Trp Glu Gly Asp
450                 455                 460

Ser Leu Asn Thr Gln Leu Phe Thr Gln Thr Ser Pro Val Ala Asp Ala
465                 470                 475                 480

Pro Asn Ile Leu Thr Ser Ser Val Leu Met Ala Pro Ala Ser Glu Asp
                485                 490                 495

Glu Asp Asn Val Leu Lys Ala Phe Thr Val Pro Lys Asn Arg Ser Leu
            500                 505                 510

Ala Ser Pro Leu Gln Pro Cys Ser Ser Thr Trp Glu Pro Ala Ser Cys
        515                 520                 525

Gly Lys Met Glu Glu Gln Met Thr Ser Ser Ser Gln Ala Arg Lys Tyr
530                 535                 540

Val Asn Ala Phe Ser Ala Arg Thr Leu Val Met
```

545 550 555

<210> SEQ ID NO 18
<211> LENGTH: 745
<212> TYPE: PRT
<213> ORGANISM: Homo sapiens

<400> SEQUENCE: 18

Met Ala Arg Arg Pro Arg His Ser Ile Tyr Ser Ser Asp Glu Asp
1               5                   10                  15

Glu Asp Phe Glu Met Cys Asp His Asp Tyr Asp Gly Leu Leu Pro Lys
                20                  25                  30

Ser Gly Lys Arg His Leu Gly Lys Thr Arg Trp Thr Arg Glu Glu Asp
            35                  40                  45

Glu Lys Leu Lys Lys Leu Val Glu Gln Asn Gly Thr Asp Asp Trp Lys
        50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
        115                 120                 125

Gln Cys Arg Glu Arg Trp His Asn His Leu Asn Pro Glu Val Lys Lys
    130                 135                 140

Thr Ser Trp Thr Glu Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Glu Ser Ser Lys Ala Ser Gln Pro
        195                 200                 205

Ala Val Ala Thr Ser Phe Gln Lys Asn Ser His Leu Met Gly Phe Ala
    210                 215                 220

Gln Ala Pro Pro Thr Ala Gln Leu Pro Ala Thr Gly Gln Pro Thr Val
225                 230                 235                 240

Asn Asn Asp Tyr Ser Tyr Tyr His Ile Ser Glu Ala Gln Asn Val Ser
                245                 250                 255

Ser His Val Pro Tyr Pro Val Ala Leu His Val Asn Ile Val Asn Val
            260                 265                 270

Pro Gln Pro Ala Ala Ala Ile Gln Arg His Tyr Asn Asp Glu Asp
        275                 280                 285

Pro Glu Lys Glu Lys Arg Ile Lys Glu Leu Glu Leu Leu Met Ser
    290                 295                 300

Thr Glu Asn Glu Leu Lys Gly Gln Gln Val Leu Pro Thr Gln Asn His
305                 310                 315                 320

Thr Cys Ser Tyr Pro Gly Trp His Ser Thr Thr Ile Ala Asp His Thr
                325                 330                 335

Arg Pro His Gly Asp Ser Ala Pro Val Ser Cys Leu Gly Glu His His
            340                 345                 350

Ser Thr Pro Ser Leu Pro Ala Asp Pro Gly Ser Leu Pro Glu Glu Ser
        355                 360                 365

-continued

| | | | | | | | | | | | | |
|---|---|---|---|---|---|---|---|---|---|---|---|---|
|Ala|Ser|Pro|Ala|Arg|Cys|Met|Ile|Val|His|Gln|Gly|Thr|Ile|Leu|Asp|
| |370| | | |375| | | |380| | | |

Ala Ser Pro Ala Arg Cys Met Ile Val His Gln Gly Thr Ile Leu Asp
        370                 375                 380

Asn Asp Ser Ser Ser Trp Cys Asp Leu Ser Ser Phe Glu Phe Glu
385                 390                 395                 400

Glu Ala Asp Phe Ser Pro Ser Gln His His Thr Gly Lys Ala Leu Gln
                405                 410                 415

Leu Gln Gln Arg Glu Gly Asn Gly Thr Lys Pro Ala Gly Glu Pro Ser
            420                 425                 430

Pro Arg Val Asn Lys Arg Met Leu Ser Glu Ser Ser Leu Asp Pro Pro
        435                 440                 445

Lys Val Leu Pro Pro Ala Arg His Ser Thr Ile Pro Leu Val Ile Leu
450                 455                 460

Arg Lys Lys Arg Gly Gln Ala Ser Pro Leu Ala Thr Gly Asp Cys Ser
465                 470                 475                 480

Ser Phe Ile Phe Ala Asp Val Ser Ser Ser Thr Pro Lys Arg Ser Pro
                485                 490                 495

Val Lys Ser Leu Pro Phe Ser Pro Ser Gln Phe Leu Asn Thr Ser Ser
            500                 505                 510

Asn His Glu Asn Ser Asp Leu Glu Met Pro Ser Leu Thr Ser Thr Pro
        515                 520                 525

Leu Ile Gly His Lys Leu Thr Val Thr Thr Pro Phe His Arg Asp Gln
    530                 535                 540

Thr Val Lys Thr Gln Lys Glu Asn Thr Val Phe Arg Thr Pro Ala Ile
545                 550                 555                 560

Lys Arg Ser Ile Leu Glu Ser Ser Pro Arg Thr Pro Thr Pro Phe Lys
                565                 570                 575

His Ala Leu Ala Ala Gln Glu Ile Lys Tyr Gly Pro Leu Lys Met Leu
            580                 585                 590

Pro Gln Thr Pro Ser His Leu Val Glu Asp Leu Gln Asp Val Ile Lys
        595                 600                 605

Gln Glu Ser Asp Glu Ser Gly Ile Val Ala Glu Phe Gln Glu Asn Gly
    610                 615                 620

Pro Pro Leu Leu Lys Lys Ile Lys Gln Glu Val Glu Ser Pro Thr Asp
625                 630                 635                 640

Lys Ser Gly Asn Phe Phe Cys Ser His His Trp Glu Gly Asp Ser Leu
                645                 650                 655

Asn Thr Gln Leu Phe Thr Gln Thr Ser Pro Val Ala Asp Ala Pro Asn
            660                 665                 670

Ile Leu Thr Ser Ser Val Leu Met Ala Pro Ala Ser Glu Asp Glu Asp
        675                 680                 685

Asn Val Leu Lys Ala Phe Thr Val Pro Lys Asn Arg Ser Leu Ala Ser
    690                 695                 700

Pro Leu Gln Pro Cys Ser Ser Thr Trp Glu Pro Ala Ser Cys Gly Lys
705                 710                 715                 720

Met Glu Glu Gln Met Thr Ser Ser Ser Gln Ala Arg Lys Tyr Val Asn
                725                 730                 735

Ala Phe Ser Ala Arg Thr Leu Val Met
            740                 745

<210> SEQ ID NO 19
<211> LENGTH: 603
<212> TYPE: PRT
<213> ORGANISM: Homo sapiens

<400> SEQUENCE: 19

```
Met Ala Arg Arg Pro Arg His Ser Ile Tyr Ser Ser Asp Glu Asp Asp
1               5                  10                 15

Glu Asp Phe Glu Met Cys Asp His Asp Tyr Asp Gly Leu Leu Pro Lys
            20                  25                 30

Ser Gly Lys Arg His Leu Gly Lys Thr Arg Trp Thr Arg Glu Glu Asp
        35                  40                 45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65              70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
                100                 105                 110

Lys Arg Trp Ser Val Ile Ala Lys His Leu Lys Gly Arg Ile Gly Lys
            115                 120                 125

Gln Cys Arg Glu Arg Trp His Asn His Leu Asn Pro Glu Val Lys Lys
    130                 135                 140

Thr Ser Trp Thr Glu Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Glu Ser Ser Lys Ala Ser Gln Pro
        195                 200                 205

Ala Val Ala Thr Ser Phe Gln Lys Asn Ser His Leu Met Gly Phe Ala
210                 215                 220

Gln Ala Pro Pro Thr Ala Gln Leu Pro Ala Thr Gly Gln Pro Thr Val
225                 230                 235                 240

Asn Asn Asp Tyr Ser Tyr Tyr His Ile Ser Glu Ala Gln Asn Val Ser
                245                 250                 255

Ser His Val Pro Tyr Pro Val Ala Leu His Val Asn Ile Val Asn Val
            260                 265                 270

Pro Gln Pro Ala Ala Ala Ile Gln Arg His Tyr Asn Asp Glu Asp
    275                 280                 285

Pro Glu Lys Glu Lys Arg Ile Lys Glu Leu Glu Leu Leu Met Ser
    290                 295                 300

Thr Glu Asn Glu Leu Lys Gly Gln Gln Val Leu Pro Thr Gln Asn His
305                 310                 315                 320

Thr Cys Ser Tyr Pro Gly Trp His Ser Thr Thr Ile Ala Asp His Thr
                325                 330                 335

Arg Pro His Gly Asp Ser Ala Pro Val Ser Cys Leu Gly Glu His His
            340                 345                 350

Ser Thr Pro Ser Leu Pro Ala Asp Pro Gly Ser Leu Pro Glu Glu Ser
        355                 360                 365

Ala Ser Pro Ala Arg Cys Met Ile Val His Gln Gly Thr Ile Leu Asp
370                 375                 380

Asn Val Lys Asn Leu Leu Glu Phe Ala Glu Thr Leu Gln Phe Ile Asp
385                 390                 395                 400

Ser Phe Leu Asn Thr Ser Ser Asn His Glu Asn Ser Asp Leu Glu Met
                405                 410                 415
```

```
Pro Ser Leu Thr Ser Thr Pro Leu Ile Gly His Lys Leu Thr Val Thr
            420                 425                 430

Thr Pro Phe His Arg Asp Gln Thr Val Lys Thr Gln Lys Glu Asn Thr
        435                 440                 445

Val Phe Arg Thr Pro Ala Ile Lys Arg Ser Ile Leu Glu Ser Ser Pro
    450                 455                 460

Arg Thr Pro Thr Pro Phe Lys His Ala Leu Ala Ala Gln Glu Ile Lys
465                 470                 475                 480

Tyr Gly Pro Leu Lys Met Leu Pro Gln Thr Pro Ser His Leu Val Glu
                485                 490                 495

Asp Leu Gln Asp Val Ile Lys Gln Glu Ser Asp Glu Ser Gly Ile Val
            500                 505                 510

Ala Glu Phe Gln Glu Asn Gly Pro Pro Leu Leu Lys Lys Ile Lys Gln
        515                 520                 525

Glu Asn Ile Leu Thr Ser Ser Val Leu Met Ala Pro Ala Ser Glu Asp
    530                 535                 540

Glu Asp Asn Val Leu Lys Ala Phe Thr Val Pro Lys Asn Arg Ser Leu
545                 550                 555                 560

Ala Ser Pro Leu Gln Pro Cys Ser Ser Thr Trp Glu Pro Ala Ser Cys
                565                 570                 575

Gly Lys Met Glu Glu Gln Met Thr Ser Ser Gln Ala Arg Lys Tyr
            580                 585                 590

Val Asn Ala Phe Ser Ala Arg Thr Leu Val Met
            595                 600

<210> SEQ ID NO 20
<211> LENGTH: 605
<212> TYPE: PRT
<213> ORGANISM: Homo sapiens

<400> SEQUENCE: 20

Met Ala Arg Arg Pro Arg His Ser Ile Tyr Ser Ser Asp Glu Asp Asp
1               5                   10                  15

Glu Asp Phe Glu Met Cys Asp His Asp Tyr Asp Gly Leu Leu Pro Lys
            20                  25                  30

Ser Gly Lys Arg His Leu Gly Lys Thr Arg Trp Thr Arg Glu Glu Asp
        35                  40                  45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
        115                 120                 125

Gln Cys Arg Glu Arg Trp His Asn His Leu Asn Pro Glu Val Lys Lys
    130                 135                 140

Thr Ser Trp Thr Glu Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190
```

-continued

Val Glu Gln Glu Gly Tyr Leu Gln Glu Ser Ser Lys Ala Ser Gln Pro
            195                 200                 205

Ala Val Ala Thr Ser Phe Gln Lys Asn Ser His Leu Met Gly Phe Ala
210                 215                 220

Gln Ala Pro Pro Thr Ala Gln Leu Pro Ala Thr Gly Gln Pro Thr Val
225                 230                 235                 240

Asn Asn Asp Tyr Ser Tyr Tyr His Ile Ser Glu Ala Gln Asn Val Ser
            245                 250                 255

Ser His Val Pro Tyr Pro Val Ala Leu His Val Asn Ile Val Asn Val
            260                 265                 270

Pro Gln Pro Ala Ala Ala Ile Gln Thr Gln Asn His Thr Cys Ser
            275                 280                 285

Tyr Pro Gly Trp His Ser Thr Thr Ile Ala Asp His Thr Arg Pro His
            290                 295                 300

Gly Asp Ser Ala Pro Val Ser Cys Leu Gly Glu His Ser Thr Pro
305                 310                 315                 320

Ser Leu Pro Ala Asp Pro Gly Ser Leu Pro Glu Ser Ala Ser Pro
            325                 330                 335

Ala Arg Cys Met Ile Val His Gln Gly Thr Ile Leu Asp Asn Val Lys
            340                 345                 350

Asn Leu Leu Glu Phe Ala Glu Thr Leu Gln Phe Ile Asp Ser Phe Leu
            355                 360                 365

Asn Thr Ser Ser Asn His Glu Asn Ser Asp Leu Glu Met Pro Ser Leu
            370                 375                 380

Thr Ser Thr Pro Leu Ile Gly His Lys Leu Thr Val Thr Thr Pro Phe
385                 390                 395                 400

His Arg Asp Gln Thr Val Lys Thr Gln Lys Glu Asn Thr Val Phe Arg
            405                 410                 415

Thr Pro Ala Ile Lys Arg Ser Ile Leu Glu Ser Ser Pro Arg Thr Pro
            420                 425                 430

Thr Pro Phe Lys His Ala Leu Ala Ala Gln Glu Ile Lys Tyr Gly Pro
            435                 440                 445

Leu Lys Met Leu Pro Gln Thr Pro Ser His Leu Val Glu Asp Leu Gln
            450                 455                 460

Asp Val Ile Lys Gln Glu Ser Asp Glu Ser Gly Ile Val Ala Glu Phe
465                 470                 475                 480

Gln Glu Asn Gly Pro Pro Leu Leu Lys Lys Ile Lys Gln Glu Val Glu
            485                 490                 495

Ser Pro Thr Asp Lys Ser Gly Asn Phe Phe Cys Ser His His Trp Glu
            500                 505                 510

Gly Asp Ser Leu Asn Thr Gln Leu Phe Thr Gln Thr Ser Pro Val Ala
            515                 520                 525

Asp Ala Pro Asn Ile Leu Thr Ser Ser Val Leu Met Ala Pro Ala Ser
            530                 535                 540

Glu Asp Glu Asp Asn Val Leu Lys Ala Phe Thr Val Pro Lys Asn Arg
545                 550                 555                 560

Ser Leu Ala Ser Pro Leu Gln Pro Cys Ser Ser Thr Trp Glu Pro Ala
            565                 570                 575

Ser Cys Gly Lys Met Glu Glu Gln Met Thr Ser Ser Ser Gln Ala Arg
            580                 585                 590

Lys Tyr Val Asn Ala Phe Ser Ala Arg Thr Leu Val Met
            595                 600                 605

<210> SEQ ID NO 21
<211> LENGTH: 1910
<212> TYPE: DNA
<213> ORGANISM: Artificial Sequence
<220> FEATURE:
<223> OTHER INFORMATION: synthetic

<400> SEQUENCE: 21

```
atggctagac gacctcgaca ctccatctac tcctccgatg aggatgatga ggacatcgag      60
atgtgtgacc acgattacga cggcctgctg ccaaaatctg gaaaacggca cctgggcaaa     120
acacgctgga ctcgggagga ggacgaaaaa ctcaaaaaac tcgtcgaaca gaatggcacc     180
gatgactgga aagtgatcgc caactacctg ccaaatcgaa ccgacgtcca gtgtcagcac     240
cggtggcaga aagtcctgaa tcctgaactc attaagggcc cttggacaaa agaggaggat     300
cagcgagtca ttgaactggt ccagaaatac ggccctaaac ggtggtctgt gattgctaaa     360
cacctgaagg gacggattgg gaaacagtgt agggaacgat ggcataacca tctgaaccct     420
gaggtgaaaa aaacttcttg gactgaggag gaggatcgga tcatctacca ggcccacaaa     480
cgactgggga accgctgggc tgagattgcc aaactgctgc ccgggagaac cgataatgct     540
atcaaaaacc attggaactc cactatgagg cggaaagtcg aacaggaggg atacctccag     600
gaaccttcta aagcatccca gacacctgtg gctacaagct ttcagaaaaa caaccatctc     660
atgggctttg gacatgctag tccccctagt cagctgtcac ccagtggaca gtctagtgtg     720
aactctgaat accctactac ccacattgct gaggctcaga catttcctc tcacgtgcct     780
taccctgtcg ctctccacgt caacattgtg aacgtgcccc agcctgccgc tgctgctatc     840
cagagacact acaacgatga ggaccctgag aaagagaaac gaatcaagga gctggaactg     900
ctgctcatgt ctaccgagaa tgagctgaag ggacagcagg ctctgcctac tcagaatcac     960
acctgctcct accctggctg gcattcaacc tcaatcgtcg accagacacg acctcatggg    1020
gatagtgccc ctgtgtcatg cctgggcgaa catcatgcta caccttccct gcctgccgac    1080
cccggatctc tgcctgagga atctgcttct cctgcccgct gtatgatcgt ccatcagggc    1140
acaattctcg ataacgtgaa aaacctgctc gaattcgccg aaacactcca gtttatcgat    1200
tccttcctga acacctcttc caaccacgaa tcttccggac tggatgcccc aactctccca    1260
tccacaccac tcattggcca caaactcacc ccttgtcggg atcagaccgt gaaacccag    1320
aaagaaaact ccattttccg gacacctgct atcaaacgga gcattctgga gagtagtcct    1380
agaacccca ccccttcaa acatgctctg gccgctcagg aaatcaaata cgggcccctg    1440
aaaatgctgc ctcagacccc ttctcatgct gtggaggacc tccaggacgt gatcaaacag    1500
gaatccgacg aatctggcat tgtcgctgag tttcaggagt ctggccctcc tctgctgaaa    1560
aaaatcaaac aggaggtgga gtctcctacc gaaaaatccg gcaacttctt ctgctccaat    1620
cattgggccg agaactcact gagcacccag ctgtttagtc aggcatctcc tgtggccgac    1680
gctcccaata ttctcacttc ctccgtgctc atgacccccg tgagtgagga tgaggataac    1740
gtgctgaagg cctttactgt gcctaaaaac cgccctctgg tgggaccact ccagccttgt    1800
tccggagctt gggaacctgc ctcttgtgga aaaaccgagg accagatgac tgctagtgga    1860
cccgctagaa aatacgtgaa cgccttctcc gctcgaactc tcgtgatggc                1910
```

T CELLS MODIFIED TO OVEREXPRESS C-MYB

CROSS-REFERENCE TO RELATED APPLICATION

This patent application is the U.S. national stage of International Patent Application Number PCT/US2016/048435, filed Aug. 24, 2016, which claims the benefit of U.S. Provisional Patent Application No. 62/209,497, filed Aug. 25, 2015, each of which is incorporated by reference in its entirety herein.

STATEMENT REGARDING FEDERALLY SPONSORED RESEARCH AND DEVELOPMENT

This invention was made with Government support under project number ZIABC011480 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 106,246 Byte ASCII (Text) file named "737889 ST25.txt," dated Feb. 5, 2018.

BACKGROUND OF THE INVENTION

Adoptive cell therapy can be an effective treatment for diseases (e.g., cancer) in some patients. However, obstacles to the overall success of adoptive cell therapy still exist. For example, the in vivo persistence, survival, and anti-tumor activity of T cells can, in some cases, decrease following adoptive transfer. Alternatively or additionally, in some cases, the increased differentiation of T cells can pose obstacles to the treatment of diseases.

In spite of considerable research into methods of producing cells for adoptive cell therapy and treatments for cancer and viral diseases, there still exists a need for improved methods for producing cells for adoptive cell therapy and treating and/or preventing cancer and viral diseases.

BRIEF SUMMARY OF THE INVENTION

An embodiment of the invention provides an isolated or purified T cell comprising an antigen-specific receptor, wherein the antigen-specific receptor is a T cell receptor (TCR) or a chimeric antigen receptor (CAR), wherein the T cell has been modified to express a transcription factor at a level that is higher than the level of the transcription factor expressed by a T cell that has not been modified to express the transcription factor, wherein the transcription factor is V-Myb Avian Myeloblastosis Viral Oncogene Homolog (c-Myb), a functional variant of c-Myb, or a functional fragment of c-Myb.

Another embodiment of the invention provides a method of inhibiting the differentiation of T cells, the method comprising introducing a nucleic acid encoding a transcription factor into isolated or purified T cells under conditions sufficient to obtain an increased expression of the transcription factor as compared to T cells that lack the introduced nucleic acid, wherein the transcription factor is c-Myb, a functional variant of c-Myb, or a functional fragment of c-Myb, and wherein the increased expression of the transcription factor inhibits differentiation of the T cells.

Further embodiments of the invention provide related populations of T cells, pharmaceutical compositions, and methods of treating a disease.

DETAILED DESCRIPTION OF THE INVENTION

Figure 1:
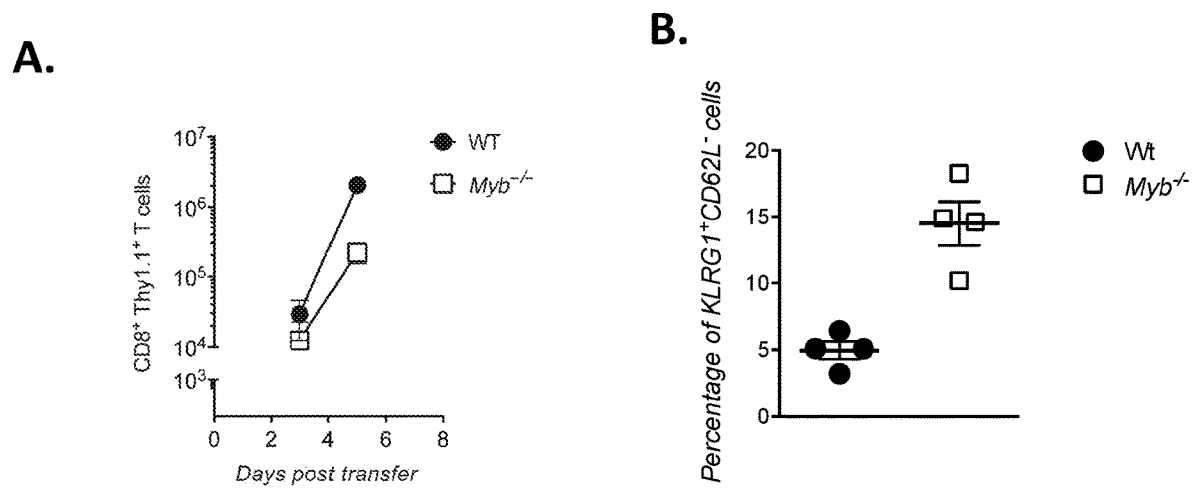
FIG. 1A is a graph showing the quantity of Thy1.1$^+$ pmel-1 CD8$^+$ T cells measured at three and five days after adoptive transfer of wild-type (WT) CD8$^+$ T (circles) or pmel-1 Myb$^{-/-}$ CD8$^+$ T (squares) cells into WT mice infected with gp-100 vaccinia virus (VV).
FIG. 1B is a graph showing the percentage of KLRG1$^{30}$ CD62L$^-$ cells obtained from the spleen on day five after adoptive transfer of WT CD8$^+$ T (circles) or pmel-1 Myb$^{-/-}$ CD8$^+$ T (squares) cells into WT mice infected with gp-100 vaccinia virus (VV). There were four mice in each treatment group.

V-Myb Avian Myeloblastosis Viral Oncogene Homolog (c-Myb) is a transcription factor that is a member of the MYB family of transcription factor genes. The c-Myb protein contains three domains: an N-terminal DNA-binding domain, a central transcriptional activation domain, and a C-terminal transcriptional repression domain.

It has been discovered that c-Myb is involved in T cell differentiation. In particular, it has been discovered that T cells lacking c-Myb are more differentiated as compared to their wild-type counterparts, whereas T cells that are modified to overexpress c-Myb are less differentiated than their wild-type counterparts.

An embodiment of the invention provides an isolated or purified T cell comprising an antigen-specific receptor. The T cell has been modified to express a transcription factor at a level that is higher than the level of the transcription factor expressed by a T cell that has not been modified to express the transcription factor, wherein the transcription factor is c-Myb, a functional variant of c-Myb, or a functional fragment of c-Myb. Hereinafter, c-Myb, functional variants of c-Myb, and functional fragments of c-Myb are referred to collectively as "c-Myb," unless specified otherwise.

The inventive T cells have been modified to overexpress c-Myb. In this regard, the modified T cell expresses c-Myb at a level that is higher than the level of c-Myb expressed by a T cell that has not been modified with respect to c-Myb expression (e.g., wild-type T cells). For example, if the T cell has been modified to comprise a vector encoding c-Myb, as described in more detail below, the modified T cell including the vector expresses c-Myb at a level that is higher than the level of c-Myb expressed by a control T cell that does not contain the vector.

The inventive T cells may provide many advantages, for example, an increase of any one or more of in vivo proliferation, survival, persistence, anti-tumor activity, and anti-viral activity as compared to T cells that have not been modified to overexpress c-Myb (e.g., T cells that lack the vector). The inventive T cells may be less differentiated as compared to T cells that have not been modified to overexpress c-Myb T cells that lack the vector). The numbers of less differentiated T cells are believed to expand to greater numbers in vitro as compared to more differentiated T cells. Therefore, the inventive T cells may be suitable for adoptive cell therapy.

The T cell may be isolated or purified. The term "isolated," as used herein, means having been removed from its natural environment. The term "purified," as used herein, means having been increased in purity, wherein "purity" is a relative term, and not to be necessarily construed as absolute purity. A "purified" T cell refers to a T cell which has been separated from other natural components, such as tissues, cells, proteins, nucleic acids, etc.

The T cell can be any T cell, such as a cultured T e.g., a primary T cell, or a T cell from a cultured T cell line, e.g., Jurkat, SupT1 etc., or a T cell obtained from a mammal. If obtained from a mammal, the T cell can be obtained from numerous sources, including but not limited to blood, bone marrow, lymph node, thymus, spleen, or other tissues or fluids. Cells can also be enriched for or purified. Preferably, the T cell is a human T cell. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD4$^+$ T cells, CD8$^+$ T cells (e.g., cytotoxic T cells), peripheral blood mononuclear cells (PBMCs), peripheral blood leukocytes (PBLs), tumor infiltrating cells (TILs), memory T cells, naïve T cells, and the like. Preferably, the cell is a $CD8^+$ T cell.

The inventive compositions can comprise a single T cell or a population thereof. The population of T cells can be a heterogeneous population comprising the T cell that has been modified to overexpress c-Myb (e.g., a T cell comprising the vector), in addition to at least one other cell, e.g., a T cell, which has not been modified to overexpress c-Myb (e.g., T cell lacking the vector), or a cell other than a T cell, e.g., a B cell, a macrophage, a neutrophil, an erythrocyte, a melanocyte, a hepatocyte, an endothelial cell, an epithelial cell, a muscle cell, a brain cell, etc. Alternatively, the population of cells can be a substantially homogeneous population, in which the population mainly comprises T cells that have been modified to overexpress c-Myb. The population also can be a clonal population of T cells, in which all T cells of the population are clones of a single T cell that has been modified to overexpress c-Myb, such that all T cells of the population overexpress c-Myb and have genetically identical TCRs.

A T cell of the invention can be present in a population of cells or a composition in an amount of about 10% or more, e.g., about 30% or more, about 50% or more, about 60% or more, about 70% or more, about 75% or more, about 80% or more, about 85% or more, or about 90% or more, based on the total number of cells in the population or composition. Alternatively, or in addition, the T cell of the invention can be present in a population of cells or a composition in an amount of about 95% or less, e.g., about 90% or less, about 85% or less, about 80% or less, about 75% or less, about 70% or less, about 60% or less, about 40% or less, or about 30% or less based on the total number of cells in the population or composition. Thus, the T cell of the invention can be present in a population of cells or a composition in an amount bounded by any two of the above endpoints. For example, the T cell of the invention can be present in a population of cells or a composition in an amount of about 30 to about 60%, about 50 to about 90%, about 60 to about 80%, about 80 to about 90%, or about 75 to about 85%.

In an embodiment of the invention, the T cell comprises an antigen-specific receptor. The phrases "antigen-specific" and "antigenic specificity," as used herein, mean that the receptor can specifically bind to and immunologically recognize an antigen, or an epitope thereof, such that binding of the receptor to antigen, or the epitope thereof, elicits an immune response. In an embodiment of the invention, the antigen-specific receptor is a T cell receptor (TCR). The antigen-specific TCR generally comprises two polypeptides (i.e., polypeptide chains), such as an α-chain of a TCR, a β-chain of a TCR, a γ-chain of a TCR, a δ-chain of a. TCR, or a combination thereof. Such polypeptide chains of TCR.s are known in the art. The antigen-specific receptor can comprise any amino acid sequence, provided that the receptor can specifically bind to and immunologically recognize an antigen, such as a disease-associated antigen or epitope thereof.

The antigen-specific receptor can be an endogenous TCR, i.e., the antigen-specific TCR that is endogenous or native to (naturally-occurring on) the T cell. In such a case, the T cell comprising the endogenous TCR can be a T cell that was isolated from a mammal which is known to express the particular disease-specific antigen. In certain embodiments, the T cell is a primary T cell isolated from a host afflicted with a cancer. In some embodiments, the T cell is a tumor infiltrating lymphocyte (TIL) or a peripheral blood lymphocyte (PBL) isolated from a human cancer patient.

In some embodiments, the mammal from which a T cell is isolated is immunized with an antigen of, or specific for, a disease. Desirably, the mammal is immunized prior to obtaining the T cell from the mammal. In this way, the isolated T cells can include T cells induced to have specificity for the disease to be treated, or can include a higher proportion of cells specific for the disease.

Alternatively, a T cell comprising an endogenous antigen-specific TCR can be a T cell within a mixed population of cells isolated from a mammal, and the mixed population can be exposed to the antigen which is recognized by the endogenous TCR while being cultured in vitro, in this manner, the T cell which comprises the TCR that recognizes the disease-specific antigen, expands or proliferates in vitro, thereby increasing the number of T cells having the endogenous antigen-specific receptor.

The antigen-specific TCR can be an exogenous TCR, i.e., an antigen-specific TCR that is not native to (not naturally-occurring on) the T cell. A recombinant TCR is a TCR which has been generated through recombinant expression of one or more exogenous TCR α-, β-, γ-, and/or δ-chain encoding genes, A recombinant TCR can comprise polypeptide chains derived entirely from a single mammalian species, or the antigen-specific TCR can be a chimeric or hybrid TCR comprised of amino acid sequences derived from TCRs from two different mammalian species. For example, the antigen-specific TCR can comprise a variable region derived from a murine TCR, and a constant region of a human TCR such that the TCR is "humanized." Methods of making recombinant TCRs are known in the art. See, for example, U.S. Pat. Nos. 7,820,174; 8,785,601; 8,216,565; and U.S. Patent Application Publication No. 2013/0274203.

A T cell of the invention comprising an endogenous antigen-specific TCR can also be transformed, e.g., transduced or transfected, with one or more nucleic acids encoding an exogenous (e.g., recombinant) TCR or other recombinant chimeric receptor. Such exogenous chimeric receptors, e.g., chimeric TCRs, can confer specificity for additional antigens to the transformed T cell beyond the antigens for which the endogenous TCR is naturally specific. This can, but need not, result in the production of T cell having dual antigen specificities.

In an embodiment of the invention, the antigen-specific receptor is a "chimeric antigen receptor" (CAR). Typically, a CAR comprises the antigen binding domain of an antibody, e.g., a single-chain variable fragment (scFv), fused to the transmembrane and intracellular domains of a TCR. Thus, the antigenic specificity of a TCR of the invention can be encoded by a scFv which specifically binds to the antigen, or an epitope thereof. Methods of making such chimeric TCRs are known in the art. See, for example, U.S. Pat. No. 8,465,743 and U.S. Patent Application Publication Nos. 2014/0037628 and 2014/0274909.

Any suitable nucleic acid encoding a CAR, TCR, or TCR-like protein or polypeptide can be used. In these embodiments, transformation with a nucleic acid encoding c-Myb, as discussed below, can occur before, after, or simultaneously with, antigen-specific receptor transformation. The antigen-specific receptor encoded by the transformed nucleic acids can be of any suitable form including for example, a single-chain TCR or a fusion with other proteins or polypeptides (e.g., without limitation co-stimulatory molecules).

The antigen which is recognized by the antigen-specific receptor can be any antigen which is characteristic of a disease. For example, the antigen may be, but is not limited to, a cancer antigen (also termed a tumor antigen or a tumor associated antigen) or a viral antigen. Viral antigens are known in the art and include, for example, any viral protein, e.g., env, gag, pol, gp120, thymidine kinase, and the like.

The term "cancer antigen," as used herein, refers to any molecule (e.g., protein, polypeptide, peptide, lipid, carbohydrate, etc.) solely or predominantly expressed or overexpressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host. Cancer antigens are known in the art and include, for instance, mesothelin, CD19, CD22, CD276 (B7H3), gp100, MART-1, Epidermal Growth Factor Receptor Variant III (EGFRVIII), TRP-1, TRP-2, tyrosinase, NY-ESO-1 (also known as CAG-3), MAGE-1, MAGE-3, etc.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

The disease which is associated with or is characterized by the antigen recognized by the antigen-specific receptor can be any disease. For instance, the disease can be a cancer or a viral disease, as discussed herein.

The cancer may be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In certain preferred embodiments, the antigen-specific receptor has specificity for an antigen derived from melanoma.

For purposes herein, "viral disease" means a disease that can be transmitted from person to person or from organism to organism, and is caused by a virus. In an embodiment of the invention, the viral disease is caused by a virus selected from the group consisting of herpes viruses, pox viruses, hepadnaviruses, papilloma viruses, adenoviruses, coronoviruses, orthomyxoviruses, paramyxoviruses, flaviviruses, and caliciviruses. For example, the viral disease may be caused by a virus selected from the group consisting of respiratory syncytial virus (RSV), influenza virus, herpes simplex virus, Epstein-Barr virus, varicella virus, cytomegalovirus, hepatitis A virus, hepatitis B virus, hepatitis C virus, human immunodeficiency virus (HIV), human T-lymphotropic virus, calicivirus, adenovirus, and Arena virus.

The viral disease may be, for example, influenza, pneumonia, herpes, hepatitis, hepatitis A, hepatitis B. hepatitis C, chronic fatigue syndrome, sudden acute respiratory syndrome (SARS), gastroenteritis, enteritis, carditis, encephalitis, bronchiolitis, respiratory papillomatosis, meningitis, HIV/AIDS, and mononucleosis.

A T cell comprising an antigen-specific receptor can be isolated or purified from a source using any suitable technique known in the art. For example, a T cell comprising an antigen-specific TCR present in a mammalian tissue, biological fluid (e.g., blood), or in vitro culture medium can be separated from impurities, e.g., other cell types, proteins, nucleic acids, etc. using flow cytometry, immunomagnetic separation, or a combination thereof.

An isolated or purified T cell may be modified to overexpress c-Myb. The T cell may be modified to overexpress c-Myb in any suitable manner. In an embodiment of the invention, the T cell may be modified to overexpress c-Myb using genome editing techniques. Genome editing techniques can modify gene expression in a target cell by inserting, replacing, or removing DNA in the genome using an artificially engineered nuclease. Examples of such nucleases may include zinc finger nucleases (ZFNs) (Gommans et al., *J. Mol. Biol.*, 354(3): 507-519 (2005)), transcription activator-like effector nucleases (TALENs) (Zhang et al., *Nature Biotechnol.*, 29: 149-153 (2011)), the CRISPR/Cas system (Cheng et al., *Cell Res.*, 23: 1163-71 (2013)), and engineered meganucleases (Riviere et al., *Gene Ther.*, 21(5): 529-32 (2014)). The nucleases create specific double-stranded breaks (DSBs) at targeted locations in the genome, and use endogenous mechanisms in the cell to repair the induced break by homologous recombination (HR) and nonhomologous end-joining (NHEJ). Such techniques may be used to achieve overexpression of c-Myb in T cells.

In another embodiment of the invention, the T cell may be modified (e.g., transduced or transfected) so as to comprise a nucleic acid encoding c-Myb. Preferably, the nucleic acid is a recombinant nucleic acid. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in viva replication.

The terms "nucleic acid" and "polynucleotide," as used herein, refer to a polymeric form of nucleotides of any length, either ribonucleotides (RNA) or deoxyribonucleotides (DNA). These terms refer to the primary structure of the molecule, and thus include double- and single-stranded DNA, double- and single-stranded RNA, and double-stranded DNA-RNA hybrids. The terms include, as equivalents, analogs of either RNA or DNA made from nucleotide analogs and modified polynucleotides such as, though not limited to, methylated and/or capped polynucleotides. Suitable nucleotide analogs are known and are described in, e.g., U.S. Patent Application Publication 2012/0101148, and references cited therein. In an embodiment of the invention, the nucleic acid is complementary DNA (cDNA).

The term "nucleotide" as used herein refers to a monomeric subunit of a polynucleotide that consists of a heterocyclic base, a sugar, and one or more phosphate groups. The naturally occurring bases (guanine (G), adenine (A), cytosine (C), thymine (T), and uracil (U)) are typically derivatives of purine or pyrimidine, though the invention includes the use of naturally and non-naturally occurring base analogs. The naturally occurring sugar is the pentose (five-carbon sugar) deoxyribose (which forms DNA) or ribose (which forms RNA), though the invention includes the use of naturally and non-naturally occurring sugar analogs. Nucleic acids are typically linked via phosphate bonds to form nucleic acids or polynucleotides, though many other linkages are known in the art (e.g., phosphorothioates, boranophosphates and the like). Methods of preparing polynucleotides are within the ordinary skill in the art (Green and Sambrook, *Molecular Cloning: A Laboratoty Manual*, (4th Ed.) Cold Spring Harbor Laboratory Press, New York (2012)).

The nucleic acid may comprise any suitable c-Myb nucleotide sequence, which may encode any suitable c-Myb amino acid sequence from any mammal. In an embodiment of the invention, the c-Myb sequence is a mouse c-Myb sequence. Two mouse c-Myb transcriptional variants include mRNA Genbank Accession Nos.: NM_001198914.1 (SEQ NO: 1) and NM_010848.3 (SEQ ID NO: 2), with corresponding protein sequence Genbank Accession Nos. NP_001185843.1 (SEQ ID NO: 3) and NP_034978.3 (SEQ ID NO: 4), respectively. Mouse genomic c-Myb sequences include Genbank Accession Nos: NC_000076.6, CH466562.2, K03547.1, and AC_00032.1. Mouse c-Myb mRNA sequences also include Genbank Accession Nos: AA170760.1AK036518.1, AK038118.1 AK084390.1, and AK088020.1. Mouse c-Myb amino acid sequences also include Genbank Accession Nos: EDL03418.1, EDL03419.1AAA39786.1, AAA39787.1AAA39783.1, AAA39782.1, AAA37505.1, CAA27724.1, CAA34425.1, and CAA34426.1. Other mouse sequences, as well as other c-Myb species, can be employed in accordance with the invention.

In a preferred embodiment of the invention, the c-Myb sequence is a human c-Myb sequence. Eight human c-Myb transcriptional variants and their corresponding amino acid sequences are set forth in Table A.

TABLE A

| Isoform Number | mRNA Genbank Accession No. | Amino acid sequence Genbank Accession No. |
|---|---|---|
| 1 | NM_001130173.1 (SEQ ID NO: 5) | NP_001123645.1 (SEQ ID NO: 13) |
| 2 | NM_005375.2 (SEQ ID NO: 6) | NP_005366.2 (SEQ ID NO: 14) |
| 3 | NM_001130172.1 (SEQ ID NO: 7) | NP_001123644.1 (SEQ ID NO: 15) |
| 4 | NM_001161656.1 (SEQ ID NO: 8) | NP_001155128.1 (SEQ ID NO: 16) |
| 5 | NM_001161657.1 (SEQ ID NO: 9) | NP_001155129.1 (SEQ ID NO: 17) |
| 6 | NM_001161658.1 (SEQ ID NO: 10) | NP_001155130.1 (SEQ ID NO: 18) |
| 7 | NM_001161659.1 (SEQ ID NO: 11) | NP_001155131.1 (SEQ ID NO: 19) |
| 8 | NM_001161660.1 (SEQ ID NO: 12) | NP_001155132.1 (SEQ ID NO: 20) |

Human genomic c-Myb sequences include Genbank Accession Nos: NG_012330.1, NC_900006.12, and NC_018917.2. Human c-Myb mRNA sequences also include Genbank Accession Nos: AJ606317.1, AJ606318.1, AJ606319.1, AJ606320.1, AJ606321.1AJ606322.1, AJ606323.1, AJ606324.1, AJ616235.1, and AJ616791.1. Human c-Myb amino acid sequences also include Genbank Accession Nos: EAW47968.1, CAS01767.1, ADL14499.1, CBX51725.1, AAA72118.1, AAB49034.1, AAB49035.1, AAC96326.1, CAE55168,1, CAE55169.1, CAE55170.1, CAE55171.1, CAE55172.1, CAE55173.1, CAE55174.1, CAE55175.1, CAE82649.1 and CAF04477.1. Other human sequences, as well as other c-Myb species can be employed in accordance with the invention.

In an embodiment of the invention, the nucleic acid comprises a codon-optimized nucleotide sequence encoding c-Myb. Without being bound to any particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. In this regard, the nucleic acid encoding c-Myb may comprise the codon-optimized nucleotide sequence of SEQ ID NO: 21, which encodes mouse c-Myb having the amino acid sequence of SEQ ID NO: 4.

In other embodiments, the nucleic acid comprises, consists essentially of, or consists of a nucleic acid sequence which is at least about 75%, e.g., at least about 80%, at least about 85%, at least about 90%, at least about 91%, at least about 92%, at least about 93%, at least about 94%, at least about 95%, at least about 96%, at least about 97%, at least about 98%, or at least about 99% identical to any of the nucleotide sequences described herein, e.g., any one of SEQ ID NOs: 1-2, 5-12, and 21. In an embodiment of the invention, the nucleic acid comprises, consists essentially of, or consists of the nucleotide sequence of any one of SEQ ID NOs: 1-2, 5-12, and 21.

In certain preferred embodiments, the nucleic acid encoding c-Myb is carried in a recombinant expression vector. Accordingly, an embodiment of the invention provides an isolated or purified T cell comprising a vector comprising (i) a nucleic acid encoding c-Myb and (ii) a heterologous nucleic acid sequence. The phrase "heterologous nucleic acid sequence," as used herein, means a nucleic acid sequence that does not naturally occur in the species that expresses the c-Myb encoded by the vector. For example, if the c-Myb encoded by the vector is mouse c-Myb, the heterologous nucleic acid sequence in the vector may be any sequence that does not naturally occur in a mouse. In an embodiment in which the c-Myb encoded by the vector is human c-Myb, the heterologous nucleic acid sequence in the vector may be any sequence that does not naturally occur in a human. The heterologous nucleic acid sequence may be a nucleic acid sequence from any species other than the species that expresses the c-Myb encoded by the vector.

The recombinant expression vector can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. The vector may contain regulatory nucleic acid sequences which provide for c-Myb expression.

The recombinant expression vector can be any suitable recombinant expression vector that contains a heterologous nucleic acid sequence as described above. Suitable vectors include those designed for propagation and expansion or for expression or both, such as plasmids and viruses. For example, the vector can be selected from the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZap11 (Stratagene), λEMBL4, and λNM1149, also can be used. Examples of plant expression vectors useful in the context of the invention include pBI01, pBI01.2, pBI101.3, pBI121 and pBIN19 (Clontech). Examples of animal expression vectors useful in the context of the invention include pEUK-C1, pMAM, and pMAMneo (Clontech).

In some embodiments, the recombinant expression vector is a viral vector. Suitable viral vectors include, without limitation, retroviral vectors, alphaviral, vaccinial, adenoviral, adenoassociated viral, herpes viral, and fowl pox viral vectors, and preferably have a native or engineered capacity to transform T cells.

The recombinant expression vectors can be prepared using standard recombinant DNA techniques described in, for example, Green and Sambrook, supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector can comprise regulatory sequences, such as transcription and translation initiation and termination codons, which are specific to the type of host (e.g., bacterium, fungus, plant, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the recombinant expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleic acid encoding c-Myb. Preferably, the promoter is functional in T cells. The selection of a promoter, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vector can be designed for either transient expression, for stable expression, or for both. Also, the recombinant expression vectors can be made for constitutive expression or for inducible expression.

The vectors useful in the context of the invention can be "naked" nucleic acid vectors (i.e., vectors having little or no proteins, sugars, and/or lipids encapsulating them), or vectors complexed with other molecules. Other molecules that can be suitably combined with the vectors include without limitation viral coats, cationic lipids, liposomes, polyamines, gold particles, and targeting moieties such as ligands, receptors, or antibodies that target cellular molecules.

The nucleic acid may encode a polypeptide or protein comprising any of the c-Myb amino acid sequences described herein. In an embodiment of the invention, the nucleic acid encodes a c-Myb polypeptide or protein comprising, consisting, or consisting essentially of an amino acid sequence selected from the group consisting of SEQ ID NOs: 3-4 and 13-20.

In an embodiment of the invention, the nucleic acid encodes a functional fragment of any of the c-Myb proteins or polypeptides described herein. The functional fragment of the c-Myb protein or polypeptide can comprise any contiguous part of the c-Myb protein or polypeptide that retains a relevant biological activity of the c-Myb protein or polypeptide, e.g., any one or more of inhibiting the differentiation of T cells, binding to DNA, activating transcription, and repressing transcription. Any given fragment of a c-Myb protein or polypeptide can be tested for such biological activity using methods known in the art. For example, the functional fragment can comprise, consist essentially of, or consist of any one or two of the N-terminal DNA-binding domain, the central transcriptional activation domain, or the C-terminal transcriptional repression domain of any of the c-Myb proteins or polypeptides described herein. In reference to the parent c-Myb protein or polypeptide, the functional fragment preferably comprises, for instance, about 10% or more, 25% or more, 30% or more, 50% or more, 60% or more, 80% or more, 90% or more, or even 95% or more of the parent c-Myb protein or polypeptide.

In an embodiment of the invention, the nucleic acid encodes a functional variant of any of the c-Myb proteins or polypeptides described herein. The term "functional variant," as used herein, refers to a c-Myb protein or polypeptide having substantial or significant sequence identity or similarity to a parent c-Myb protein or polypeptide, which functional variant retains the biological activity of the c-Myb protein or polypeptide of which it is a variant. Functional variants encompass, for example, those variants of the c-Myb protein or polypeptide described herein (the parent c-Myb protein or polypeptide) that retain the ability to provide any one or more of inhibition of T cell differentiation, binding to DNA, activation of transcription, and repression of transcription to a similar extent, the same extent, or to a higher extent, as the parent c-Myb protein or polypeptide. In reference to the parent c-Myb protein or polypeptide, the functional variant can, for instance, be at least about 75%, e.g., at least about 80%, at least about 85%, at least about 90%, at least about 91%, at least about 92%, at least about 93%, at least about 94%, at least about 95%, at least about 96%, at least about 97%, at least about 98%, or at least about 99% identical in amino acid sequence to any of the c-Myb proteins or polypeptides described herein, e.g., any one of SEQ ID NOs: 3-4 and 13-20.

The functional variant can, for example, comprise the amino acid sequence of the parent c-Myb protein or polypeptide with at least one conservative amino acid substitution. Conservative amino acid substitutions are known in the art, and include amino acid substitutions in whiCh one amino acid having certain physical andlor chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent c-Myb protein or polypeptide with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent c-Myb protein or polypeptide.

The c-Myb protein or polypeptide can consist essentially of the specified amino acid sequence or sequences described herein, such that other components of the functional variant, e.g., other amino acids, do not materially change the biological activity of the functional variant. In this regard, the c-Myb protein or polypeptide can, for example, consist essentially of the amino acid sequence of any of SEQ ID NOs: 3-4 and 13-20.

Preferably, a T cell comprising an antigen-specific receptor is isolated or purified as described herein, and then contacted with a nucleic acid encoding c-Myb ex vivo or in vitro using methods described herein or any other method known in the art. Examples of such methods include, but are not limited to, the use of a lipid, protein, particle, or other molecule capable of facilitating cell transformation with the nucleic acid. However, a T cell comprising an antigen-specific receptor also can be contacted with a nucleic acid encoding c-Myb in vivo, such as by way of a gene gun, for example.

T cells which have not been modified to overexpress c-Myb (including, e.g., T cells that lack the vector encoding c-Myb) may express a basil level of c-Myb mRNA, polypeptide, or protein. However, the isolated or purified T cell of the invention overexpresses c-Myb mRNA, polypeptide, or protein as compared to a control T cell that has not been modified to overexpress c-Myb. For example, without limiting the invention, a T cell or a population thereof overexpressing c-Myb can contain an amount of c-Myb (mRNA, protein, or polypeptide) that is 1.5-fold higher or more, e.g., 2-fold higher or more, 3-fold higher or more, 5-fold higher or more, 10-fold higher or more, 20-fold higher or more, or 50-fold higher or more, than the amount of c-Myb present in a control T cell or a population thereof that has not been modified to overexpress c-Myb. Thus, the c-Myb can be present in a T cell or population thereof in an amount bounded by any two of the above endpoints. For example, the T cell or a population thereof overexpressing c-Myb can contain an amount of c-Myb (mRNA, protein, or polypeptide) that is about 1.5-fold to about 20-fold higher, about 2-fold to about 5-fold higher, about 3-fold to about 50-fold higher, about 10-fold or higher, or about 20-fold to about 50-fold higher, than the amount of c-Myb present in a control T cell or a population thereof that has not been modified to overexpress c-Myb. Any suitable method known in the art can be utilized to determine the amount of c-Myb mRNA, protein, or polypeptide present in a T cell or a population thereof, such as quantitative reverse transcription polymerase chain reaction (RT-PCR) or stem-loop quantitative RT-PCR.

The isolated or purified T cell of the invention may have a less differentiated phenotype as compared to a T cell that has not been modified to overexpress c-Myb. In an embodiment of the invention, the isolated or purified T cell invention may have a naïve T cell ($T_N$), T memory stem cell ($T_{SCM}$), or central memory T cell ($T_{CM}$) phenotype. Alternatively or additionally, the inventive T cell lacks an effector memory T cell ($T_{EM}$) phenotype. For example, CCR7 and CD62L are expressed by $T_N$, $T_{SCM}$, and $T_{CM}$ cells, but are not expressed by $T_{EM}$ cells. The transcription factors LEF1, FOXP1, and KLF7 are expressed by $T_N$, $T_{SCM}$, and $T_{CM}$ cells, but are not expressed by $T_{EM}$ cells. CD45RO and KLRG1 are not expressed by $T_N$ or $T_{SCM}$ cells, but are expressed by $T_{EM}$ cells, Gattinoni et al., Nat. Rev. Cancer, 12: 671-84 (2012). In an embodiment of the invention, the isolated or purified T cell of the invention may be any one or more of $CD62L^+$, $KLRG1^-$, $LEF1^+$, $FOXP1^+$, and $KLF7^+$, $CCR7^+$, $CD57^-$, and $CD45RO^-$. Preferably, the T cell is one or both of $CD62L$ and $KLRG1^-$. In an especially preferred embodiment, the T cell is both $CD62L^+$ and $KLRG1^-$. Alternatively or additionally, $T_N$, $T_{SCM}$, and $T_{CM}$ cells may be characterized by longer telomeres as compared to those of $T_{EM}$ cells.

The invention also provides a method of treating or preventing a disease in a mammal. The method comprises administering to the mammal any of the T cells described herein, or a population thereof, or a composition comprising any of the T cells described herein, in an amount effective to treat or prevent the disease in the mammal. In an embodiment of the invention, the disease is cancer or a viral disease. The cancer and viral disease may be any of the cancers and viral diseases described herein with respect to other aspects of the invention.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer or a viral disease in a patient. Furthermore, the treatment or prevention provided by the inventive method can include treatment or prevention of one or more conditions or symptoms of the cancer or viral disease being treated or prevented. For example, treatment or prevention can include promoting the regression of a tumor. Also, for purposes herein, "prevention" can encompass delaying the onset of the cancer or viral disease, or a symptom or condition thereof.

The term "mammal" as used herein refers to any mammal, including, but not limited to, mice, hamsters, rats, rabbits, cats, dogs, cows, pigs, horses, monkeys, apes, and humans. Preferably, the mammal is a human.

In the treatment or prevention of a disease in a mammal, the T cells that have been modified to overexpress c-Myb can be transferred into the same mammal from which T cells were obtained. In other words, the T cell used in the inventive method of treating or preventing can be an autologous T cell, i.e., can be obtained from the mammal in which the disease is treated or prevented. Alternatively, the T cell can be allogenically transferred into another mammal. Preferably, the T cell is autologous to the mammal in the inventive method of treating or preventing a disease in the mammal.

In the instance that the T cells are autologous to the mammal, the mammal can be immunologically naïve, immunized, diseased, or in another condition prior to isolation of the T cells from the mammal. In some instances, it is preferable for the method to comprise immunizing the mammal with an antigen of the disease prior to isolating the T cell from the mammal, modifying the obtained T cell to overexpress c-Myb, and the administering of the T cell, or a population or composition thereof. As discussed herein, immunization of the mammal with the antigen of disease will allow the population of T cells having an endogenous TCR reactive with the disease-specific antigen to increase in numbers, which will increase the likelihood that the T cell obtained for being modified to overexpress c-Myb will have a desired antigen-specific TCR.

In accordance with the invention, a mammal with a disease can be therapeutically immunized with an antigen from, or associated with, that disease, including immunization via a vaccine. While not desiring to be bound by any particular theory, the vaccine or immunogen is provided to enhance the mammal's immune response to the disease antigen present in or on the infectious agent or diseased tissue. Such a therapeutic immunization includes, but is not limited to, the use of recombinant or natural disease proteins, peptides, or analogs thereof, or modified disease peptides, or analogs thereof that can be used as a vaccine therapeutically as part of adoptive immunotherapy. The vaccine or immunogen, can be a cell, cell lysate (e.g., from cells transfected with a recombinant expression vector), a recombinant expression vector, or antigenic protein or polypeptide. Alternatively, the vaccine, or immunogen, can be a partially or substantially purified recombinant disease protein, polypeptide, peptide or analog thereof, or modified proteins, polypeptides, peptides or analogs thereof. The protein, polypeptide, or peptide may be conjugated with lipoprotein or administered in liposomal form or with adjuvant. Preferably, the vaccine comprises one or more of (i) the disease-antigen for which the antigen-specific receptor of the T cell of the invention is specific, (ii) an epitope of the antigen, and (iii) a vector encoding the antigen or the epitope.

The inventive method of treating or preventing a disease in a mammal can comprise additional steps. For instance, a variety of procedures, as discussed below, can be performed on the T cells prior to, substantially simultaneously with, or after their isolation from a mammal. Similarly, a variety of procedures can be performed on the T cells prior to, substantially simultaneously with, or after modifying the T cells to over-express c-Myb.

In an embodiment of the invention, the T cells are expanded in vitro after modifying the T cells to over-express c-Myb, but prior to the administration to a mammal. Expansion of the numbers of T cells can be accomplished by any of a number of methods as are known in the art as described in, for example, U.S. Pat. Nos. 8,034,334; 8,383,099; and U.S. Patent Application Publication No, 2012/0244133. For example, expansion of the numbers of T cells may be carried out by culturing the T cells with OKT3 antibody, IL-2, and feeder PBMC (e.g., irradiated allogeneic PBMC). In another embodiment of the invention, the T cells are not expanded in vitro after modifying the T cells to over-express c-Myb and prior to the administration to a mammal.

An embodiment of the invention provides a pharmaceutical composition comprising the inventive T cell or a population thereof and a pharmaceutically acceptable carrier. The pharmaceutically acceptable carriers described herein, for example, vehicles, adjuvants, excipients, and diluents, are well-known and readily available to those skilled in the art. Preferably, the pharmaceutically acceptable carrier is chemically inert to the active agent(s), e.g., the T cell, and does not elicit any detrimental side effects or toxicity under the conditions of use.

The composition can be formulated for administration by any suitable route, such as, for example, an administration route selected from the group consisting of intravenous, intratumoral, intraarterial, intramuscular, intraperitoneal, intrathecal, epidural, and subcutaneous administration routes. Preferably, the composition is formulated for a parenteral route of administration. An exemplary pharmaceutically acceptable carrier for cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumin.

For purposes of the invention, the amount or dose of the inventive population of cells or pharmaceutical composition administered (e.g., numbers of cells when the inventive population of cells is administered) should be sufficient to effect, e.g., a therapeutic or prophylactic response, in the patient over a reasonable time frame. For example, the dose of the inventive population of cells or pharmaceutical composition should be sufficient to treat or prevent cancer or a viral disease in a period of from about 2 hours or longer, e.g., 12 to 24 or more hours, from the time of administration. In certain embodiments, the time period could be even longer. The dose will be determined by the efficacy of the particular inventive population of cells or pharmaceutical composition administered and the condition of the patient, as well as the body weight of the patient to be treated.

Many assays for determining an administered dose are known in the art. For purposes of the invention, an assay, which comprises comparing the extent to which target cells are lysed upon administration of a given dose of such T cells to a mammal among a set of mammals of which is each given a different dose of the cells, could be used to determine a starting dose to be administered to a patient. The extent to which target cells are lysed upon administration of a certain dose can be assayed by methods known in the art.

The dose of the inventive population of cells or pharmaceutical composition also will be determined by the existence, nature and extent of any adverse side effects that might accompany the administration of a particular inventive population of cells or pharmaceutical composition. Typically, the attending physician will decide the dosage of the population of cells or pharmaceutical composition with which to treat each individual patient, taking into consideration a variety of factors, such as age, body weight, general health, diet, sex, inventive population of cells or pharmaceutical composition to be administered, route of administration, and the severity of the condition being treated.

Any suitable number of T cells of the invention can be administered to a mammal. While a single T cell of the invention theoretically is capable of expanding, and providing a therapeutic benefit, it is preferable to administer about $10^2$ or more, e.g., about $10^3$ or more, about $10^4$ or more, about $10^5$ or more, about $10^8$ or more, T cells of the invention. Alternatively, or additionally about $10^{12}$ or less, e.g., about $10^{11}$ or less, about $10^9$ or less, about $10^7$ or less, or about $10^5$ or less, T cells of the invention can be administered to a mammal. The number of T cells of the invention can be administered to a mammal in an amount bounded by any two of the above endpoints, e.g., about $10^2$ to about $10^5$, about $10^3$ to about $10^7$, about $10^3$ to about $10^9$, or about $10^5$ to about $10^{10}$.

As explained above, the isolated or purified T cell of the invention that is modified to over-express c-Myb may be less differentiated as compared to a control T cell that has not been modified to overexpress c-Myb. Accordingly, an embodiment of the invention provides a method of inhibiting the differentiation of T cells.

The method may comprise isolating or purifying a T cell from a source. The method may comprise introducing any of the nucleic acids encoding c-Myb described herein with respect to other aspects of the invention into the isolated or purified T cells under conditions sufficient to obtain an increased expression of c-Myb as compared to T cells that lack the introduced nucleic acid. The T cells may be isolated from a source, the nucleic acid may be introduced into the T cells, and the c-Myb expression may be increased as described herein with respect to other aspects of the invention.

The increased expression of c-Myb may inhibit differentiation of the T cells. In this regard, the T cells produced by the method may have a less differentiated phenotype as compared to a T cell that does not contain the introduced nucleic acid encoding c-Myb. In an embodiment of the invention, the T cell produced by the inventive method may have a $T_N$, $T_{SCM}$, or $T_{CM}$ phenotype. Alternatively or additionally, the T cell produced by the inventive method may lack a $T_{EM}$ phenotype. In an embodiment of the invention, the method may further comprise one or both of (i) increasing the expression of CD62L by the T cells and (ii) decreasing the expression of KLRG1 by the T cells. Preferably, the method comprises both (i) and (ii).

The following examples further illustrate the invention but, of course, should not be construed as in any way limiting its scope.

EXAMPLES

The following materials and methods were employed in the experiments described in Examples 1-9.

Mice.

Myb fl/fl (C57BL/6) mice were a generous gift from Tim Bender, Va. C57BL/6 mice, Ly5.1 (B6.SJL-PtprcaPepcb/BoyJ) mice and pme1-1 (B6.Cg-Thy1a/Cy Tg(TcraTerb) 8Rest/J) mice were from the Jackson Laboratory (Bar Harbor, Me.); Cre-ERT2 (B6-Gt(ROSA)26Sortm9(cre/Esr1)Arte) mice were from Taconic (Hudson, N.Y.). The pme1-1 mice were crossed with myb fl/fl mice and Cre-ERT2 mice to generate pme1-1 Cre-ERT2 myb fl/fl mice. All mouse experiments were done with the approval of the National Cancer institute Animal Use and Care Committee.

Antibodies, Flow Cytometry and Cell Sorting.

Anti-Ly5.1, anti-Thy-1.1 (OX-7), anti-CD62L (MEL-14), anti-CD8α (53-6.7), anti-KLRG-1 (2F1) antibodies were from BD Biosciences (Franklin Lakes, N.J.). A LSRII flow cytometer (BD Biosciences) was used for flow cytometry acquisition. Samples were analyzed with FLOWJO software (TreeStar, Ashland, Oreg.). Naive CD8+ T cells were sorted with a FACSARIA cell sorter (BD Biosciences).

Retroviral Vector Construction and Virus Production.

A sequence composed of a codon-optimized myb cDNA (SEQ ID NO: 21) and a sequence encoding Thy-1.1 joined by a sequence encoding the picornavirus 2A ribosomal skip peptide21 was cloned into a MSGV-1 vector. The sequence encoded a mouse c-Myb protein having the amino acid sequence of SEQ ID NO: 4. PLATINUM ECO cell lines (Cell Biolabs, San Diego, Calif.) were used for gamma-retroviral production by transfection with DNA plasmids through the use of LIPOFECTAMINE 2000 reagent (Invitrogen, Waltham, Mass.). Virus was collected 36 hours (h) after transfection.

In Vitro Activation and Transduction of CD8+ T Cells.

CD8+ T cells were separated from non-CD8+ T cells using a MACS negative selection kit (Miltenyi Biotech, Bergisch Gladbach, Germany). CD8+ T cells were activated on plates coated with anti-CD3ε antibody (2 µg/ml; 145-2C11; BD Biosciences) and soluble anti-CD28 antibody (1 µg/ml; 37.51; BD Biosciences) in culture medium containing interleukin (IL)-2 (10 ng/ml; Chiron, Emeryville, Calif.). Virus was 'spin-inoculated' at 2,000 g for 2 h at 32° C. onto plates coated with RETRONECTIN reagent (Takara, Shiga, Japan). CD8+ T cells activated for 24 h were spun onto plates after aspiration of viral supernatants.

Adoptive Cell Transfer and Infection

Adoptive transfer of cells ($50 \times 10^3$ to $100 \times 10^3$ cells) and infection with recombinant vaccinia virus or adenovorus virus expressing human gp100 (rFPhgp100; Therion Biologics, Cambridge, Mass.) were carried out.

Counting of Adoptively Transferred Cells.

Mice were sacrificed after infection. Samples were enriched for CD8+ T cells, (MACS negative selection kit) and cells were counted by trypan blue exclusion. The frequency of transferred T cells was determined by measuring the expression of CD8 and Thy-1.1 Ly5.2 or CFSE (carboxyfluorescein succinimidyl ester) by flow cytometry. The absolute number of pme1-1 cells was calculated by multiplying the total cell count by the percentage of CD8+ Thy-1.1+ or CD8+Ly5.2+.

Example 1

This example demonstrates that deficiency of c-Myb impairs accumulation of the numbers of T cells.

The pme1-1 mouse model is a useful tool for modeling the treatment of malignant melanoma using adoptive cell therapy (Overwijk et al., *J. Exp. Med.*, 198(4): 569-80 (2003)). Adoptive transfer of T cells expressing the anti-gp100 TCR from pme1-1 mice can effectively mediate the regression of tumors when administered in combination with a lymphodepleting pretreatment regimen, cytokine administration, and vaccination (Zeng et al., *J. Exp. Med*, 201: 139-148 (2005); Gattinoni et al., *J. Exp. Med.*, 202: 907-912 (2005); Klebanoff et al., *Proc. Natl. Acad. Sci. USA*, 101: 1969-1974 (2004)).

CD8+ T cells were isolated from pme1-1 wild-type (WT) mice and Myb knockout mice (Myb$^{-/-}$). The isolated T cells were transduced with a retroviral vector encoding the Thy1.1 antigen in order to facilitate assessment of the T cells by flow cytometry upon transfer into host mice. The transduced CD8+ T cells ($1 \times 10^5$) were adoptively transferred into WT mice infected with gp100 vaccinia virus (VV). The expression of Thy1.1 by the pme1-1 CD8+ T cells was assessed by flow cytometry 0-5 days after infection. The percentage of Thy1.1+ T cells (after gating on CD8+ cells) on Day 3 or Day 5 after infection is shown in Table 1. The quantification of Thy1.1+ pme1-1 CD8+ T cells 3 and 5 days after infection is shown in FIG. 1A.

TABLE 1

|   | Day 3 | Day 5 |
|---|---|---|
| WT | 0.0997 | 2.12 |
| Myb$^{-/-}$ | 0.0205 | 0.365 |

As shown in Table 1 and FIG. 1A, deficiency of c-Myb impairs accumulation of the numbers of T cells.

Example 2

This example demonstrates that deficiency of c-Myb promotes differentiation.

Pmel-1 WT CD8$^+$ T cells or pmel-1 Myb$^{-/-}$ CD8$^+$ T cells were transduced and adoptively transferred into infected WT mice as described in Example 1. The expression of KLRG1 and CD62L by Thy1.1$^+$ pmel-1 CD8$^+$ T cells that were isolated from spleen was measured by flow cytometry on day 5 after adoptive transfer.

The percentages of cells expressing the indicated phenotypes are shown in Table 2. The percentage of KLRG1$^+$ CD26L$^-$ cells obtained from four mice is shown in FIG. 1B.

TABLE 2

|   | WT | Myb$^{-/-}$ |
|---|---|---|
| KLRG1$^+$/CD62L$^+$ | 4.64 | 8.94 |
| KLRG1$^-$/CD62L$^+$ | 48 | 34.1 |
| KLRG1$^+$/CD62L$^-$ | 5.09 | 18.3 |
| KLRG1$^-$/CD62L$^-$ | 42.3 | 38.7 |

As shown in Table 2 and FIG. 1B, deficiency of c-Myb promotes T cell differentiation.

Example 3

This example demonstrates that overexpression of c-Myb enhances T cell proliferation.

CD8$^+$ T cells were isolated from pmel-1 WT mice. The isolated T cells were transduced with a retroviral vector encoding (i) Thy1.1 only ("Thy1.1") or (ii) Thy1.1 and c-Myb (SEQ ID NO: 4) ("Thy1.1 Myb").

Thy1.1 CD8$^+$ T cells (5×10$^4$) or Thy1.1 Myb CD8$^+$ T cells (5×10$^4$) were adoptively co-transferred into WT mice infected with gp100-VV. The expression of Thy1.1 and Ly5.1 by splenic T cells was measured by flow cytometry (after gating on CD8$^+$ T cells) 3-30 days after infection and 5 days after heterologous infection with gp100 adenovirus (on day 30 of gp100-VV infection). The percentages of Thy1.1$^+$ Ly5.1$^-$ or Thy1.1$^+$ Ly5.1$^+$ cells are shown in Table 3 and the abundance of Thy1.1$^+$ T cells 0-30 days (FIG. 2A) and 5 days (FIG. 2B) after heterologous infection with gp100 adenovirus is shown in FIGS. 2A-2B.

TABLE 3

|   | Thy1.1$^+$ Ly5.1$^-$ | Thy1.1$^+$ Ly5.1$^+$ |
|---|---|---|
| Day 0 | 49.5 | 49.3 |
| Day 3 after infection | 0.0185 | 0.179 |
| Day 5 after infection | 0.332 | 1.23 |
| Day 10 after infection | 0.429 | 0.717 |
| Day 30 after infection | 0.0973 | 0.0836 |
| Day 5 after heterologous infection with gp100 adenovirus | 1.56 | 7.25 |

Figure 2:
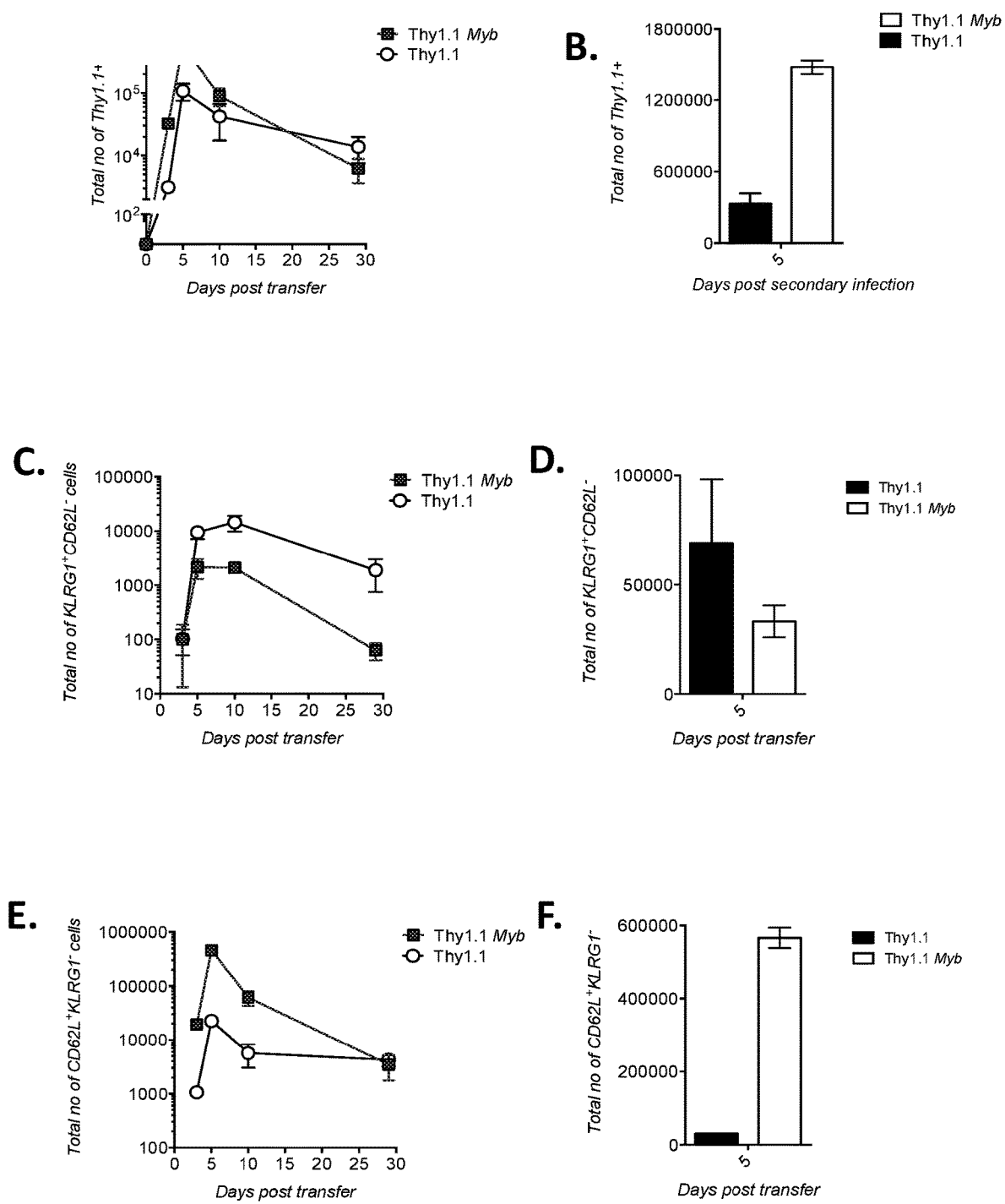
FIG. 2A is a graph showing the total number of Thy1.1$^+$ pmel-1 CD8$^+$ T cells in the spleen after adoptive transfer of Thy1.1 CD8$^+$ (circles) or Thy1.1 Myb CD8$^+$ T cells (squares) into WT mice infected with gp100-VV, assessed at 0-30 days after transfer. Data represent mean and error bars are S.E.M.
FIG. 2B is a graph showing the total number of Thy1.1$^+$ pmel-1 CD8$^+$ T cells in the spleen after adoptive transfer of Thy1.1 CD8$^+$ (shaded bars) or Thy1.1 Myb CD8$^+$ T cells (unshaded bars) into WT mice infected with gp100-VV, assessed at 5 days after heterologous reinfection (on day 30 of gp100-VV infection) with gp100 adenovirus. Data represent mean and error bars are S.E.M.
FIGS. 2C and 2E are graphs showing the total number of KLRG1$^+$CD62L$^-$ cells (FIG. 2C) or KLRG1$^-$CD62L$^+$ cells (FIG. 2E) from spleen 3-30 days post transfer of Thy1.1 CD8$^+$ (circles) or Thy1.1 Myb CD8$^+$ T cells (squares) into WT mice infected with gp100-VV (after gating on Thy1.1$^+$ Ly5.1$^-$CD8$^+$ cells or Thy1.1$^+$ Ly5.1$^+$ CD8$^+$ T cells).
FIGS. 2D and 2F are graphs showing the total number of KLRG1$^+$CD62L$^-$ cells (FIG. 2D) or KLRG1$^-$CD62L$^+$ cells (FIG. 2F) from spleen 5 days post transfer after heterologous reinfection (on day 30 of gp100-VV infection) with gp100 adenovirus (after gating on Thy1.1$^+$ Ly5.1$^-$CD8$^+$ cells or Thy1.1$^+$ Ly5.1$^+$CD8$^+$ T cells).
Figure 3:
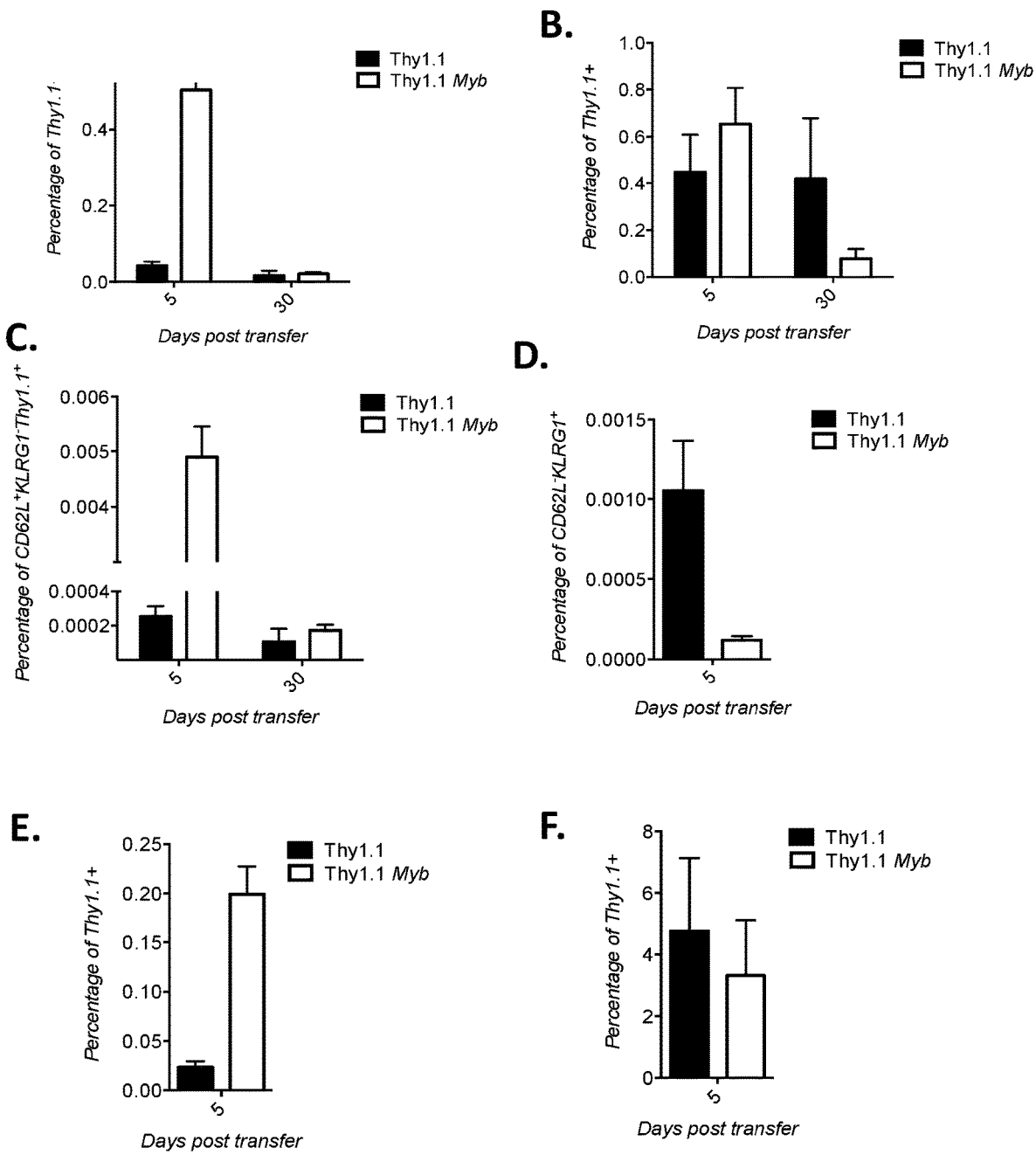
FIGS. 3A and 3B are graphs showing the percentage of Thy1.1$^+$ cells from the lymph nodes (A) and lungs (B) after adoptive transfer of Thy1.1 CD8$^+$ (shaded bars) or Thy1.1 Myb CD8$^+$ T cells (unshaded bars) into WT mice infected with gp100-VV 5-30 days post-transfer.
FIGS. 3C and 3D are graphs showing the percentage of KLRG1− CD62L$^+$Thy1.1$^+$ cells (C) or KLRG1$^+$CD62L$^-$ (D) cells from lymph node and lungs 5-30 days (C) or 5 days (D) post transfer of Thy1.1 CD8$^+$ (shaded bars) or Thy1.1 Myb CD8$^+$ T cells (unshaded bars) into WT mice infected with gp100-VV.
FIGS. 3E and 3F are graphs showing the percentage of Thy1.1$^+$ cells from lymph nodes (E) and lungs (F) 5 days post transfer after heterologous reinfection with gp100 adenovirus (on day 30 of gp100-VV infection) after gating on Thy1.1$^+$ Ly5.1$^-$CD8$^+$ cells or Thy1.1$^+$ Ly5.1$^+$ CD8$^+$ T cells.
Figure 4:
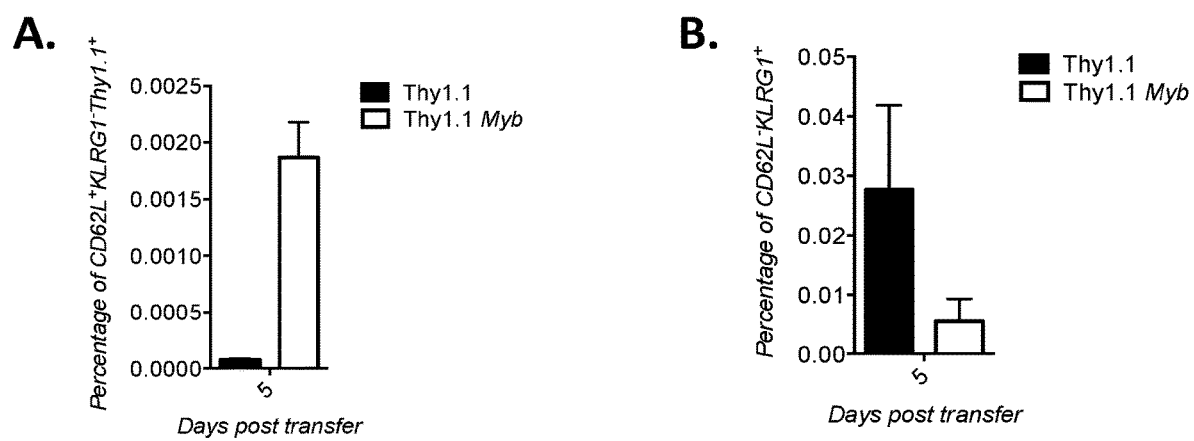
FIGS. 4A and 4B are graphs showing the percentage of KLRG1− CD62L$^+$Thy1.1$^+$ cells (A) or KLRG1$^+$CD62L$^-$ (B) cells from lymph node and lungs 5 days post transfer after heterologous reinfection with gp100 adenovirus (on day 30 of gp100-VV infection) after gating on Thy1.1$^+$ Ly5.1$^-$CD8$^+$ cells or Thy1.1$^+$ Ly5.1$^+$ CD8$^+$ T cells.

As shown in Table 3 and FIGS. 2A and 2B, the overexpression of c-Myb enhances T cell proliferation.

Example 4

This example demonstrates that overexpression of c-Myb produces cells having a central memory phenotype.

Thy1.1 and Thy1.1 Myb CD8+ T cells were adoptively co-transferred into infected WT mice as described in Example 3. KLRG1 and CD62L expression by Thy1.1$^+$ Ly5.1$^-$ and Thy1.1$^+$ Ly5.1$^+$ CD8$^+$ T cells from spleen was measured by flow cytometry. The percentages of cells having the indicated phenotype after gating on Thy1.1$^+$ Ly5.1$^-$ CD8$^+$ cells or Thy1.1$^+$ Ly5.1$^+$ CD8$^+$ T cells is shown in Table 4.

TABLE 4

|   | Day 5 | | Day 30 | | Day 5 recall | |
|---|---|---|---|---|---|---|
|   | Thy1.1 | Thy1.1 Myb | Thy1.1 | Thy1.1 Myb | Thy1.1 | Thy1.1 Myb |
| KLRG1$^+$/CD62L$^+$ | 2.3 | 0.265 | 0 | 2.34 | 1.65 | 0.478 |
| KLRG1$^-$/CD62L$^+$ | 22.5 | 80.2 | 28.9 | 52.3 | 10.2 | 39.3 |
| KLRG1$^+$/CD62L$^-$ | 9.84 | 0.309 | 11.4 | 0.781 | 25.8 | 3.11 |
| KLRG1$^-$/CD62L$^-$ | 65.6 | 19.2 | 59.7 | 44.5 | 62.3 | 57.2 |

The total number of KLRG1$^+$CD62L$^-$ cells (FIGS. 2C and 2D) and KLRG1$^-$ CD62L$^+$ cells (FIGS. 2E and 2F) from spleen 3-5 days post transfer and 5 days after heterologous infection with gp100 adenovirus (after gating on Thy1.1$^+$ Ly5.1$^-$CD8$^+$ cells or Thy1.1$^+$ Ly5.1$^+$ CD8$^+$ T cells) is shown in FIGS. 2C-2F.

The percentage of Thy1.1$^+$ cells from the lymph nodes and lungs after adoptive transfer of Thy1.1 CD8$^+$ or Thy1.1 Myb CD8$^+$ T cells into WT mice infected with gp100-VV 5-30 days post-transfer is shown in FIGS. 3A-3B and 3E-F.

The percentage of KLRG1–CD62L$^+$Thy1.1$^+$ cells and KLRG1$^+$CD62L$^-$cells from lymph node and lungs 5-30 days or 5 days post transfer of Thy1.1 CD8$^+$ or Thy1.1 Myb CD8$^+$ T cells into WT mice infected with gp100-VV is shown in FIGS. 3C-3D and 4A-4B.

As shown in Table 4, FIGS. 2C-2F, FIGS. 3A-3F, and 4A-4B, overexpression of c-Myb produces T cells having a central memory phenotype.

Example 5

This example demonstrates that c-Myb deficiency promotes proliferation and apoptosis.

Thy1.1$^+$ pmel-1$^+$ WT or Thy1.1$^+$ pmel-1$^+$ c-Myb$^{-/-}$ CD8$^+$ T cells (1×10$^5$ cells) were transferred into WT mice infected with gp-100VV. Three days after infection, the frequency of bromodeoxyuridine (BrdU)-positive cells was measured by flow cytometry. The results are shown in Table 5 and FIG. 5A. The numbers in Table 5 indicate the frequencies of BrdU-positive cells after gating on Thy1.1+ CD8+ T cells.

TABLE 5

| WT | c-Myb$^{-/-}$ |
|---|---|
| 33 | 45 |

After cell transfer and 3 days after infection as described in this Example, the frequencies of Annexin V +/−, Propidium iodide +/− and Annexin V and Propidium iodide double positive WT and c-Myb$^{-/-}$ CD8$^+$ T cells were also measured by flow cytometry after gating on Thy1.1$^+$ CD8$^+$ T cells. The results are shown in Table 6.

TABLE 6

|  | WT | Myb$^{-/-}$ |
|---|---|---|
| Annexin V$^+$Propidium iodide$^+$ | 0.698 | 4.16 |
| Annexin V$^-$Propidium iodide$^-$ | 93.2 | 79.9 |
| Annexin V$^+$Propidium iodide$^-$ | 4.47 | 13 |
| Annexin V$^-$Propidium iodide$^+$ | 1.68 | 2.89 |

Figure 5A:
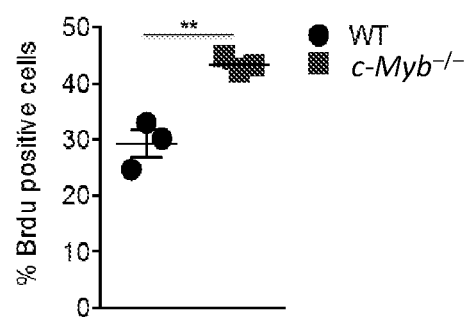
FIG. 5A is a graph showing the percentage of BrdU-positive, Thy1.1$^+$ pmel-1$^+$ WT (circles) and BrdU-positive, Thy1.1$^+$ pmel-1$^+$ c-Myb$^{-/-}$ CD8$^+$ T cells (squares) after transfer into gp-100VV-infected mice. Data were obtained from 3 or 4 mice per group. Data show mean and error bars are standard errors of mean. **P<0.01.
Figure 5B:
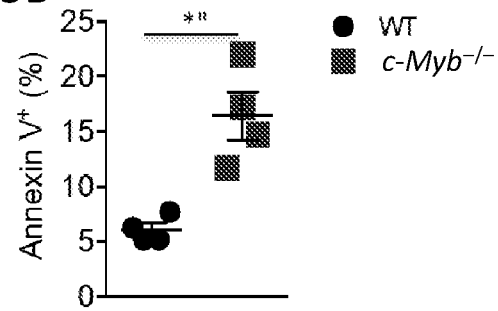
FIG. 5B is a graph showing the percentage of Annexin V-positive, Thy1.1$^+$ pmel-1$^+$ WT (circles) and Annexin V-positive, Thy1.1$^+$ pmel-1$^+$ c-Myb$^{-/-}$ CD8$^+$ T cells (squares) after transfer into gp-100VV-infected mice. Data were obtained from 3 or 4 mice per group. Data show mean and error bars are standard errors of mean. *P<0.05.

As shown in Tables 5-6 and FIGS. 5A-5B, c-Myb deficiency promotes proliferation and apoptosis.

Example 6

This example demonstrates that c-Myb deficiency downregulates Tcf7 expression and upregulates Zeb2 expression.

Thy1.1$^+$ pmel-1$^+$ WT or Thy1.1$^+$ pmel-1$^+$ c-Myb$^{-/-}$ CD8$^+$ T cells (3×10$^5$ cells) were injected into WT mice infected with gp-100VV. RNA sequencing data were obtained from CD62L$^-$KLRG1$^-$ Thy1.1$^+$ WT and CD62L$^-$KLRG1$^-$ Thy1.1$^+$ Pmel c-Myb$^{-/-}$ CD8$^+$ T cells on day 5 post transfer. The results showed that c-Myb deficiency downregulates Tcf7 expression and upregulates Zeb2 expression.

Example 7

This example demonstrates that c-Myb binds to the Tcf7 and Zeb2 promoters activating Tcf7 expression and repressing Zeb2 expression.

Figure 6A:
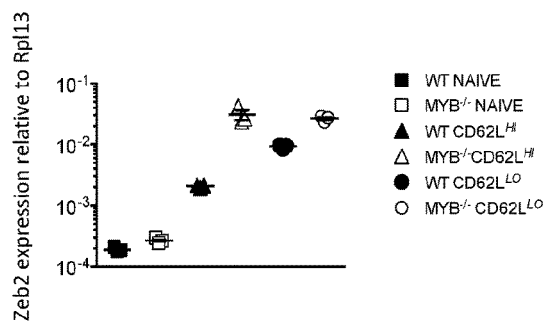
FIG. 6A is a graph showing the expression of Zeb2 relative to the expression of Rp113 in WT or c-Myb$^{-/-}$ naïve, CD62L$^+$ and CD62L$^-$populations of pmel-1 CD8$^+$ T cells before (0) or 5 days after adoptive transfer into recipient wild-type mice infected with gp100-VV. WT naïve (■), c-Myb$^{-/-}$ naïve (□), WT CD62L$^{HI}$ (▲), c-Myb$^{-/-}$ CD62L$^{HI}$ (Δ), WT CD62L$^{LO}$ (●), c-Myb$^{-/-}$ CD62L$^{LO}$ (○).
Figure 6B:
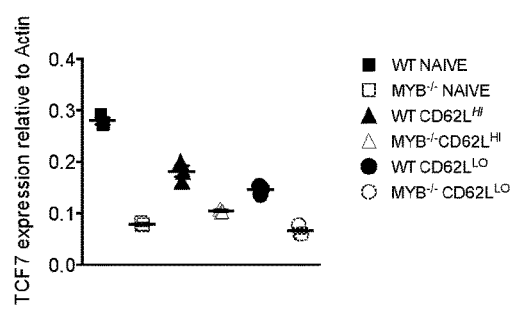
FIG. 6B is a graph showing the expression of Tcf7 relative to the expression of beta-actin in WT or c-Myb$^{-/-}$ naïve, CD62L$^+$ and CD62L$^-$ populations of pmel-1 CD8$^+$ T cells before (0) or 5 days after adoptive transfer into recipient wild-type mice infected with gp100-VV. WT naïve (■), c-Myb$^{-/-}$ naïve (□), WT CD62L$^{HI}$ (▲), c-Myb$^{-/-}$ CD62L$^{HI}$ (Δ), WT CD62L$^{LO}$ (●), c-Myb$^{-/-}$ CD62L$^{LO}$ (○).

Thy1.1$^+$ pmel-1$^+$ WT or Thy1.1$^+$ pmel-1$^+$ c-Myb$^{-/-}$ CD8$^+$ T cells were transferred into WT mice infected with gp-100VV. A quantitative RT-PCR analysis was carried out before or 5 days after adoptive transfer to measure the expression of Zeb2 and Tcf7 mRNA in WT or c-Myb$^{-/-}$ naïve, CD62L$^+$ and CD62L$^-$ populations of pmel-1 CD8$^+$ T cells. The results are shown in FIGS. 6A-6B.

Figure 6C:
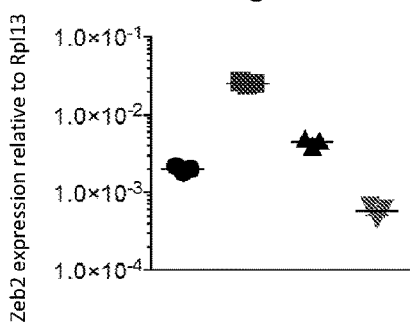
FIG. 6C is a graph showing the expression of Zeb2 relative to the expression of Rp113 by CD62L$^-$ populations of Thy1.1 (▲) or Thy1.1 c-Myb overexpressing (▼) pmel-1 CD8$^+$ T cells 5 days after adoptive transfer into recipient wild-type mice infected with gp100-VV. WT (circles) and MYB$^{-/-}$ (squares) T cells served as controls.
Figure 6D:
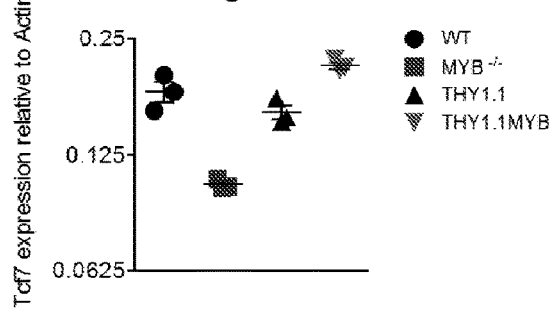
FIG. 6D is a graph showing the expression of Tcf7 relative to the expression of beta-actin by CD62L$^-$ populations of Thy1.1 (▲) or Thy1.1 c-Myb overexpressing (▼) pmel-1 CD8$^+$ T cells 5 d after adoptive transfer into recipient wild-type mice infected with gp100-VV. WT (circles) and MYB$^{-/-}$ (squares) T cells served as controls.

A quantitative RT-PCR analysis of the expression of Zeb2 and Tcf7 mRNA by CD62L$^-$ populations of Thy1.1$^+$ or Thy1.1 c-Myb overexpressing CD8$^+$ T cells 5 days after adoptive transfer into recipient wild-type mice infected with gp100-VV. The results are shown in FIGS. 6C-6D.

Figure 6E:
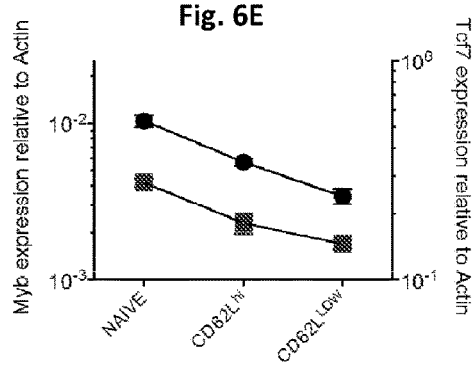
FIG. 6E is a graph showing the expression pattern of c-Myb (circles) and Tcf7 (squares) in naïve, CD62L$^+$ and CD62L$^-$ populations 5 days after adoptive transfer into recipient wild-type mice infected with gp100-VV. Results are presented relative to Actb (encoding β-actin).
Figure 6F:
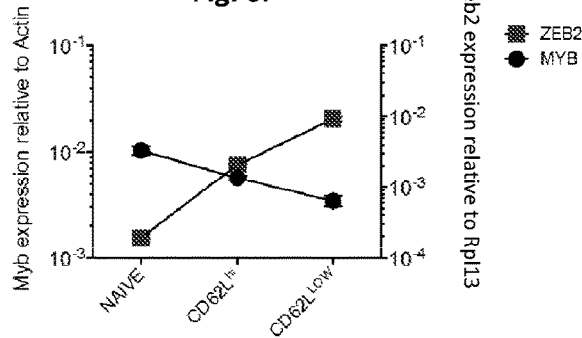
FIG. 6F is a graph showing the expression pattern of c-Myb (circles) and Zeb2 (squares) in naïve, CD62L$^+$ and CD62L$^-$ populations 5 days after adoptive transfer into recipient wild-type mice infected with gp100-VV. Results are presented relative to Actb (encoding β-actin) err Rp113 mRNA.

The expression pattern of c-Myb, Tcf7 and Zeb2 in naïve, CD62L$^+$ and CD62L$^-$ populations was measured on Day 5 after adoptive transfer into recipient wild-type mice infected with gp100-VV. The results are shown in FIGS. 6E-6F.

Figure 6G:
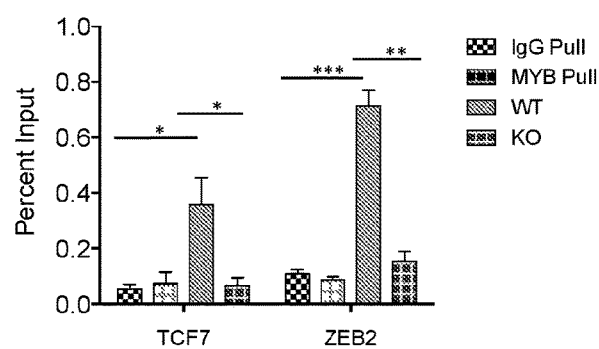
FIG. 6G is a graph showing the results or a quantitative PCR analysis of the promoter regions of Tcf7 and Zeb2 in chromatin immunoprecipitation with anti-IgG or anti-c-Myb. Error bars represent standard errors of mean. *P<0.001, P<0.1, *P<0.05.

A quantitative RT-PCR analysis of the promoter regions of Tcf7 and Zeb2 in chromatin immunoprecipitation with anti-IgG or anti-c-Myb was carried out. The results are shown in FIG. 6G.

As shown in FIGS. 6A-6G, c-Myb binds to the Tcf7 and Zeb2 promoters activating Tcf7 expression and repressing Zeb2 expression.

Example 8

This example demonstrates that Tcf7 protein expression is downregulated in c-Myb deficient CD8+ T cells and that enforced c-Myb expression enhances Tcf7 promoter activity in the reporter assay.

Thy1.1$^+$ pmel-1$^+$WT or Thy1.1$^+$ pmel-1$^+$ c-Myb$^{-/-}$ CD8$^+$ T cells were transferred into WT mice infected with gp-100VV. The expression of Tcf7 in WT and c-Myb$^{-/-}$ CD62L$^+$, CD62L$^-$ and KLRG1$^+$ populations of pmel-1 CD8$^+$ T cells from lungs was measured by flow cytometry 5 days after adoptive transfer. The percentages of cells expressing one or both of KLRG1 and CD62L are shown in. Table 7.

TABLE 7

|  | WT | Myb$^{-/-}$ |
|---|---|---|
| KLRG1$^+$CD62L$^+$ | 8.44 | 8 |
| KLRG1$^-$CD62L$^-$ | 27.6 | 24.7 |
| KLRG1$^+$CD62L$^-$ | 53.4 | 61 |
| KLRG1$^-$CD62L$^+$ | 10.6 | 6.33 |

The expression level of Tcf7 protein was measured by flow cytometry and compared between KLRG1+CD62L−, KLRG1−CD62L− and KLRG1−CD62L subpopulations of WT and c-Myb$^{-/-}$ cells. The results showed that TCF-7 protein expression is higher in WT as compared to c-Myb$^{-/-}$ cells.

Figure 7:
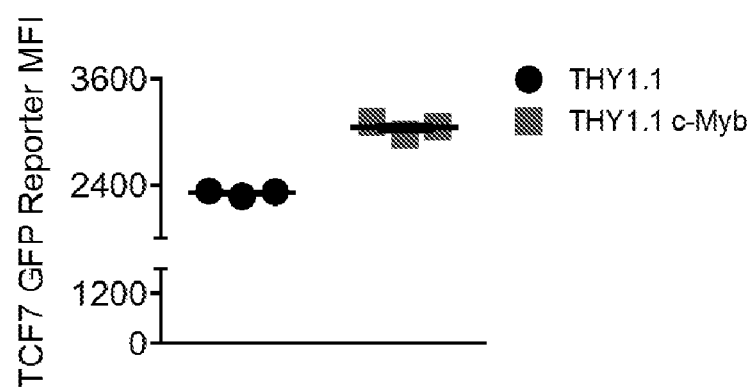
FIG. 7 is a graph showing the mean fluorescence index (MFI) of GFP expression measured in Thy1.1 or Thy1.1 c-Myb CD8$^+$ T cells from Tcf7 GFP reporter mice (p45 mice) on day 3 after in vitro activation of naïve cells and on day 2 after retroviral transduction of either Thy1.1 (circles) or Thy1.1 c-Myb (squares).

GFP expression by Thy1.1 or Thy1.1 c-Myb CD8$^+$ T cells from Tcf7 GFP reporter mice (p45 mice) on day 3 after in vitro activation of naïve cells and day 2 after retroviral transduction of either Thy1.1 or Thy1.1 c-Myb was measured by flow cytometry. The results are shown in FIG. 7.

Taken together, these data show that Tcf7 protein expression is downregulated in c-Myb deficient CD8+ T cells and enforced c-Myb expression enhances Tcf7 promoter activity in the reporter assay.

Example 9

This example demonstrates that enforced Tcf7 expression rescues the phenotype of c-Myb deficient cells.

Figure 8:
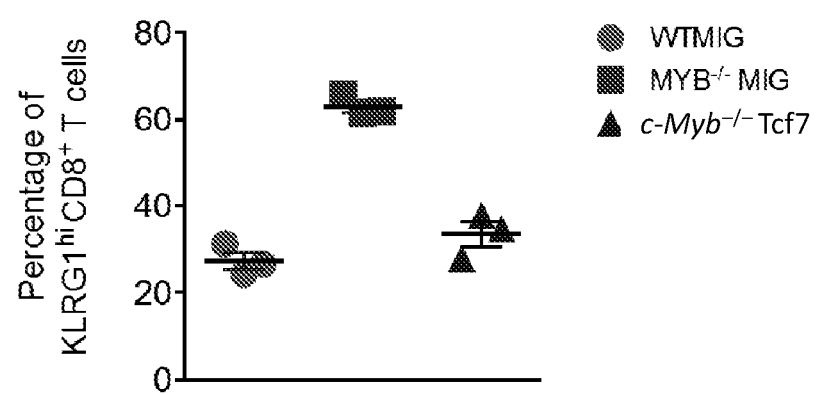
FIG. 8 is a graph showing the percentage of KLRG1$^{hi}$ CD8 T cells five days after adoptive transfer of WT (circles) or c-Myb−/− CD8+ T cells transduced either with an empty vector control MIG (squares) or Tcf7 MIG (triangles) into recipient mice.

WT and c-Myb$^{-/-}$ CD8$^+$ T cells were transduced either with an empty vector MIG (control) or Tcf7 MIG 5 and transferred into recipient wild-type mice infected with gp100-VV. Five days after transfer, KLRG1 and CD62L expression by WT and c-Myb$^{-/-}$ CD8$^+$ T cells was measured by flow cytometry. The percentages of cells expressing one or both of KLRG1 and CD62L are shown in Table 8. The percentage of KLRG1$^{hi}$ CD8 T cells is shown in FIG. 8.

TABLE 8

|  | WT MIG | c-Myb$^{-/-}$ MIG | c-Myb$^{-/-}$ Tcf7 MIG |
|---|---|---|---|
| KLRG1$^+$CD62L$^+$ | 0.799 | 0.97 | 1 |
| KLRG1$^-$CD62L$^-$ | 64 | 31.5 | 55.9 |
| KLRG1$^+$CD62L$^-$ | 24.3 | 65.7 | 37.9 |
| KLRG1$^-$CD62L$^+$ | 10.9 | 1.8 | 5.25 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified T cell comprising an antigen-specific receptor, wherein the antigen-specific receptor is a T cell receptor (TCR) or a chimeric antigen receptor (CAR), wherein the T cell has been modified to express a transcription factor at a level that is higher than the level of the transcription factor expressed by a T cell that has not been modified to express the transcription factor, wherein the transcription factor is V-Myb Avian Myeloblastosis Viral Oncogene Homolog (c-Myb) comprising an amino acid sequence selected from the group consisting of SEQ ID NOs: 3-4 and 13-20, wherein the increased expression of c-Myb inhibits differentiation of the isolated or purified T cell, and wherein the isolated or purified T cell is one or more of CD8$^+$, CD62L$^+$ and KLRG1$^-$.

2. The isolated or purified T cell according to claim 1, comprising a vector comprising (i) a nucleic acid encoding the transcription factor, and (ii) a heterologous nucleic acid sequence,
wherein the level of the transcription factor expressed by the T cell is increased as compared to the level of the transcription factor expressed by a T cell that lacks the vector.

3. The isolated or purified T cell of claim 2, wherein the vector is a viral vector.

4. The isolated or purified T cell of claim 2, wherein the nucleic acid encodes a c-Myb amino acid sequence having the amino acid sequence of SEQ ID NO: 14.

5. The isolated or purified T cell of claim 2, wherein the nucleic acid has at least 90% identity to a nucleotide sequence selected from the group consisting of SEQ ID NOs: 1-2, 5-12, and 21.

6. The isolated or purified T cell according to claim 1, wherein the receptor has antigenic specificity for a cancer antigen.

7. The isolated or purified T cell according to claim 1, wherein the receptor has antigenic specificity for a viral antigen.

8. The isolated or purified T cell according to claim 1, wherein the T cell is CD62L$^+$.

9. The isolated or purified T cell according to claim 1, wherein the T cell is KLRG1$^-$.

10. The isolated or purified T cell of claim 1, wherein the c-Myb is human c-Myb.

11. The isolated or purified T cell of claim 1, wherein the T cell is CD8$^+$.

12. The isolated or purified T cell of claim 1, wherein the receptor is a recombinant TCR.

13. The isolated or purified T cell of claim 1, wherein the receptor is a chimeric antigen receptor (CAR).

14. The isolated or purified T cell of claim 1, wherein the receptor is an endogenous TCR.

15. A population of T cells comprising at least two T cells of claim 1.

16. A pharmaceutical composition comprising the population of T cells of claim 15 and a pharmaceutically acceptable carrier.

17. A method of inhibiting the differentiation of T cells, the method comprising introducing a nucleic acid encoding a transcription factor into isolated or purified T cells under conditions sufficient to obtain an increased expression of the transcription factor as compared to T cells that lack the introduced nucleic acid,
wherein the transcription factor is c-Myb comprising a sequence selected from the group consisting of SEQ ID NOs: 3-4 and 13-20, wherein the T cells are one or more of CD8+, CD62L+ and KLRG1−, and wherein the increased expression of the transcription factor inhibits differentiation of the T cells.

18. The method according to claim 17, comprising increasing CD62L expression by the T cells.

19. The method according to claim 17, comprising decreasing KLRG1 expression by the T cells.

20. A method of treating or preventing a disease in a mammal, the method comprising administering to the mammal the population of T cells of claim 15 in an amount effective to treat or prevent the disease in the mammal, wherein the disease is a cancer or a viral disease, wherein the T cells comprise a cancer or viral antigen-specific receptor, and wherein the antigen-specific receptor is a T cell receptor (TCR) or a chimeric antigen receptor (CAR).

21. The method of claim 20, wherein the T cells of the population are autologous to the mammal.

22. An isolated or purified T cell comprising an antigen-specific receptor, wherein the antigen-specific receptor is a T cell receptor (TCR), wherein the T cell has been modified to express a transcription factor at a level that is higher than the level of the transcription factor expressed by a T cell that has not been modified to express the transcription factor,
wherein the transcription factor is V-Myb Avian Myeloblastosis Viral Oncogene Homolog (c-Myb) comprising an amino acid sequence selected from the group consisting of SEQ ID NOs: 3-4 and 13-20, wherein the increased expression of c-Myb inhibits differentiation of the isolated or purified T cell, and wherein the receptor is a recombinant TCR.

23. An isolated or purified T cell comprising an antigen-specific receptor, wherein the antigen-specific receptor is a chimeric antigen receptor (CAR), wherein the T cell has been modified to express a transcription factor at a level that is higher than the level of the transcription factor expressed by a T cell that has not been modified to express the transcription factor, and wherein the transcription factor is V-Myb Avian Myeloblastosis Viral Oncogene Homolog (c-Myb) comprising an amino acid sequence selected from the group consisting of SEQ ID NOs: 3-4 and 13-20, wherein the increased expression of c-Myb inhibits differentiation of the isolated or purified T cell.

* * * * *